(12) United States Patent
Tripathi et al.

(10) Patent No.: US 10,556,007 B2
(45) Date of Patent: Feb. 11, 2020

(54) ANTIBODY WHICH BINDS LRG1 AND METHODS OF USE

(71) Applicant: UCL Business PLC, London (GB)

(72) Inventors: Vineeta Tripathi, Surrey (GB); Rose Sheridan, London (GB); John Greenwood, London (GB); Stephen Moss, London (GB)

(73) Assignee: UCL Business LTD, London (GB)

( * ) Notice: Subject to any disclaimer, the term of this patent is extended or adjusted under 35 U.S.C. 154(b) by 48 days.

(21) Appl. No.: 15/553,965

(22) PCT Filed: Feb. 22, 2016

(86) PCT No.: PCT/GB2016/050439
§ 371 (c)(1),
(2) Date: Aug. 25, 2017

(87) PCT Pub. No.: WO2016/135462
PCT Pub. Date: Sep. 1, 2016

(65) Prior Publication Data
US 2018/0028609 A1 Feb. 1, 2018

(30) Foreign Application Priority Data
Feb. 27, 2015 (GB) .................................. 1503438.2

(51) Int. Cl.
| A61K 39/395 | (2006.01) |
| C07K 16/18 | (2006.01) |
| A61K 45/06 | (2006.01) |
| A61K 39/00 | (2006.01) |

(52) U.S. Cl.
CPC .......... *A61K 39/3955* (2013.01); *A61K 45/06* (2013.01); *C07K 16/18* (2013.01); *A61K 2039/505* (2013.01); *A61K 2039/545* (2013.01); *C07K 2317/33* (2013.01); *C07K 2317/34* (2013.01); *C07K 2317/565* (2013.01)

(58) Field of Classification Search
None
See application file for complete search history.

(56) References Cited

U.S. PATENT DOCUMENTS

| 2005/0064516 A1 | 3/2005 | Kantor et al. |
| 2007/0184503 A1 | 8/2007 | Jemmerson |
| 2009/0163434 A1 | 6/2009 | Bader |
| 2009/0163435 A1 | 6/2009 | Bader |
| 2009/0175827 A1 | 7/2009 | Byrom |
| 2009/0192111 A1 | 7/2009 | Bader |
| 2009/0227533 A1 | 9/2009 | Bader |

FOREIGN PATENT DOCUMENTS

| WO | WO-1996/06641 | 3/1996 |
| WO | WO-2000/01410 | 1/2000 |
| WO | WO-2007/040912 | 4/2007 |
| WO | WO-2008/092214 | 8/2008 |
| WO | WO-2009/061807 | 5/2009 |
| WO | WO-2011/015602 | 2/2011 |
| WO | WO-2011/027129 | 3/2011 |
| WO | WO-2011/112609 | 9/2011 |
| WO | WO-2013/132267 | 9/2013 |
| WO | WO-2013/177386 | 11/2013 |

OTHER PUBLICATIONS

Andersen et al., "Leucine-rich alpha-2-glycoprotein-1 is upregulated in sera and tumors of ovarian cancer patients," J Ovarian Res (2010) 3:21, 14 pages.
Baniak et al., "Gastric biomarkers: a global review," World Journal of Surgical Oncology (2016) 14:212.
Chang et al., "Characterization of two genes encoding leucin-rich repeat-containing proteins in grass carp *Ctenopharyngodon idellus*," Immunogenetics (2005) 56:710-721.
Cheung et al., "The HCV serum proteome: a search for fibrosis protein markers," J Viral Hepatitis (2009) 16:418-429.
Clemons et al., "The National Eye Institute Visual Function Questionnaire in the Macular Telangiectasia (MacTel) Project," Investigative Ophthalmology & Visual Science (2008) 49(10):4340-4346.
Cummings et al., "Serum leucine-rich alpha-2-glycoprotein-1 binds cytochrome c and inhibits antibody detection of this apoptotic marker in enzyme-linked immunosorbent assay," Apoptosis (2006) 11:1121-1129.
Ferrero et al., "Increased expression of one isoform of leucine-rich alpha-2-glycoprotein in peritoneal fluid of women with uterine leiomyomas," Arch Gynecol Obstet (2009) 279(3):365-371.
Goumans et al., "Controlling the angiogenic switch: a balance between two distinct TGF-b receptor signaling pathways," Trends Cardio Med (2003) 13(7):301-307.
Govorukhina et al., "Influence of clotting time on the protein composition of serum samples based on LC-MS data," J Chromotagraphy B (2009) 877:1281-1291.
Haupt et al., "Isolation and characterization of an unknown, leucine-rich 3,1-S-alpha2-glycoprotein from human serum," Physiol Chem (1977) 358(6):639-646.
Heo et al., "Identification of putative serum glycoprotein biomarkers for human lung adenocarcinoma by multilectin affinity chromatography and LC-MS/MS," Proteomics (2007) 7(23):4292-4302.
International Preliminary Report on Patentability and Written Opinion for PCT/GB2010/001681, dated Mar. 6, 2012, 10 pages.
International Search Report for PCT/GB2010/001681, dated Dec. 16, 2010, 5 pages.
International Search Report for PCT/GB2013/050580, dated May 17, 2013, 4 pages.
International Search Report for PCT/GB2016/050439, dated Jun. 23, 2016, 12 pages.
Johnson et al., "A second locus for hereditary hemorrhagic telangiectasia maps to chromosome 12," Genome Res (1995) 5(1):21-28.

(Continued)

*Primary Examiner* — Christine J Saoud
(74) *Attorney, Agent, or Firm* — Morrison and Foerster, LLP

(57) ABSTRACT

The invention provides an antibody or fragment thereof that specifically binds to human Lrg1.

15 Claims, 23 Drawing Sheets
Specification includes a Sequence Listing.

(56) References Cited

OTHER PUBLICATIONS

Kakisaka et al., "Plasma proteomics of pancreatic cancer patients by multi-dimensional liquid chromatography and two-dimensional difference gel electrophoresis (2D-DIGE): up-regulation of leucine-rich alpha-2-glycoprotein in pancreatic cancer," J Chromatogr B (2007) 852(1-2):257-267.
Kentsis et al., "Discovery of Validation of Urine Markers of Acute Pediatric Appenddicitis Using High-Accuracy Mass Spectrometry," Annals of Emergency Medicine (2009) 1-13.
Khositseth et al., "IgA nephropathy associated with Hodgkin's disease in children: a case report, literature review and urinary proteome analysis," Pediatr Nephrol (2007) 22:541-546.
Kitaguchi et al., "Characterization of the Gene Encoding Mouse Platelet Glycoprotein Ibβ," Thrombosis Research (1997) 87(2):235-244.
Ladd et al., "Increased plasma levels of the APC-interacting protein MAPRE1, LRG1, and IGFBP2 preceding a diagnosis of colorectal cancer in women," Cancer Prev Res (Phila) (2012) 5(4):655-664.
Li et al., "Expression of TGF-betas and TGF-beta type II receptor in cerebrospinal fluid of patients with idiopathic normal pressure hydrocephalus," Neurosci Lett (2007) 413(2):141-144.
Li et al., "Analysis of potential diagnostic biomarkers in cerebrospinal fluid of idiopathic normal pressure hydrocephalus by proteomics," Acta Neurochir (2006) 148:859-864.
Lynch et al., "MiRNA-335 suppresses neuroblastoma cell invasiveness by direct targeting of multiple genes from the non-canonical TGF-β signalling pathway," Carcinogenesis (2012) 33(5):976-985.
Marchuk et al., "Vascular morphogenesis: tales of two syndromes," Human Molecular Genetics (2003) 12(1):R97-112.
McAllister et al., "Endoglin, a TGF-beta binding protein of endothelial cells, is the gene for hereditary haemorrhagic telangiectasia type 1," Nat Genet (1994) 8(4):345-351.
Norkina et al., "Inflammation of the cystic fibrosis mouse small intestine," Am J Physiol Gastrointest Liver Physiol (2004) 286:G1032-G1041.
Saito et al., "Gene Expression Profiling of Mucosal Addressin Cell Adhesion Molecule-1+ High Endothelial Venule Cells (HEV) and Identification of a Leucine-Rich HEV Glycoprotein as a HEV Marker," J Immunol (2002) 168:1050-1059.
Schwick et al., "Purified Human Plasma Proteins of Unknown Function," Japan J Med Sci Biol (1981) 34:299-327.
Shen, "Cancer biomarkers and targeted therapies," Shen Cell & Bioscience (2013) 3:6.
Shirai et al., "Up-regulation of the expression of leucine-rich α2-glycoprotein in hepatocytes by the mediators of acute-phase response," Biochem Biophys Res Commun (2009) 382:776-779.
Shoki et al., "Systematic review of blood biomarkers in cystic fibrosis pulmonary exacerbations," CHEST (2013) 144(2):1659-1670.
Song et al., "The role of TGF[beta]1 and LRG1 in cardiac remodelling and heart failure," Biophysical Reviews, Springer, DE (2015) 7(1):91-104.
Spirin et al., "Basement membrane and growth factor gene expression in normal and diabetic human retinas," Curr Eye Res (1999) 18(6):490-499.
Sun et al., "Differentially expressed genes in TGF-beta 1 sensitive and resistant human hematoma cells," Cancer Lett (1995) 89(1):73-79.
Sviridov et al., "Proteinuria without albuminuria: Urinary protein excretion by a subset of patients with burn injuries," Clinica Chimica Acta (2009) 403:42-46.
Takahashi et al., "Periodicity of leucine and tandem repetition of a 24-amino acid segment in the primary structure of leucine-rich alpha 2-glycoprotein of human serum," Proc Natl Acad Sci USA (1985) 82(7):1906-1910.
Takahashi et al., "Purification of glycopeptides of human plasma proteins by high-performance liquid chromatography," J Chromatography (1984) 317:11-26.
Ten Dijke et al., "Extracellular control of TGFβ signalling in vascular development and disease," Nature Reviews (2007) 8:857-869.
Uen et al., "Comparative proteomics, network analysis and post-translational modification identification reveal differential profiles of plasma Con A-bound glycoprotein biomarkers in gastric cancer," Journal of Proteomics (2013) 83:197-213.
Wang et al., "LRG1 promotes angiogenesis by modulating endothelial TGF-[beta] signaling," Nature (2013) 499(7458):306-311.
Wang et al., "LRG1 promotes angiogenesis by modulating endothelial TGF-[beta] signaling," Nature (2013) 499(7458):306-311 Corrections and Amendments.
Weivoda et al., "ELISA for human serum leucine-rich alpha-2-glycoprotein-1 employing cytochrome c as the capturing ligand," J Immun Methods (2008) 336:22-29.
Zeng et al., "Utilizing 2-DE and MALDI-TOF MS/MS to screen differentially expressed serum proteins of silicosis," Zhonghua Lao Dong Wei Sheng Zhi Ye Bing Za Zhi (2007) 25(3):136-141.
Zhang et al., "Potential diagnostic biomarkers in serum of idiopathic pulmonary arterial hypertension," Respir Med (2009) 103:1801-1806.
Altschul et al., "A protein alignment scoring system sensitive at all evolutionary distances," J Mol Evol (1993) 36(3):290-300.
Altschul et al., "Basic local alignment search tool," J Mol Biol (1990) 215(3):403-410.
Bauminger et al., "The use of carbodiimides in the preparation of immunizing conjugates," Methods in Enzymology (1980) 70:151-159.
Caceci et al., "Fitting Curves to Data: The simplex algorithm is the answer," Byte (1984) 9:340-362.
Carmeliet et al., "Principles and mechanisms of vessel normalization for cancer and other angiogenic diseases," Nat Rev Drug Discov (2011) 10(6):417-427.
Devereuz et al., "A comprehensive set of sequence analysis programs for the VAX," Nucleic Acids Res (1984) 12(1 Pt 1):387-395.
Haupt et al., "Isolation and characterization of an unknown, leucine-rich 3.1-S-alpha2-glycoprotein from human serum (author's transl)," Hoppe Seylers Z Physiol Chem (1977) 358(6):639 Abstract only.
Henikoff et al., "Amino acid substitution matrices from protein blocks," Proc Natl Acad Sci U.S.A (1992) 89(22):10915-10919.
Karlin et al., "Applications and statistics for multiple high-scoring segments in molecular sequences," Proc Natl Acad Sci U.S.A (1993) 90(12):5873-5877.
Maes et al., "Tumor vessel normalization by chloroquine independent of autophagy," Cancer Cell (2014) 26(2):190-206.
Martin et al., "Irreversible coupling of immunoglobulin fragments to preformed vesicles. An improved method for liposome targeting," J Biol Chem (1982) 257(1):286-288.
Mueller et al., "Humanized porcine VCAM-specific monoclonal antibodies with chimeric IgG2/G4 constant regions block human leukocyte binding to porcine endothelial cells," Molecular Immunology (1997) 34(6):441-452.
Thompson et al., "The CLUSTAL_X Windows Interface: Flexible Strategies for Multiple Sequence Alignment Aided by Quality Analysis Tools," Nucleic Acids Research (1997) 25(24):4876-4882.
Wong et al., "A double-filter method for nitrocellulose-filter binding: application to protein-nucleic acid interactions," Proc Natl Acad Sci U.S.A (1993) 90(12):5428-5432.

Scale bar = 100μm

A

B

C

A

B

IgG
n=4

15C4
n=5

Figure 21A
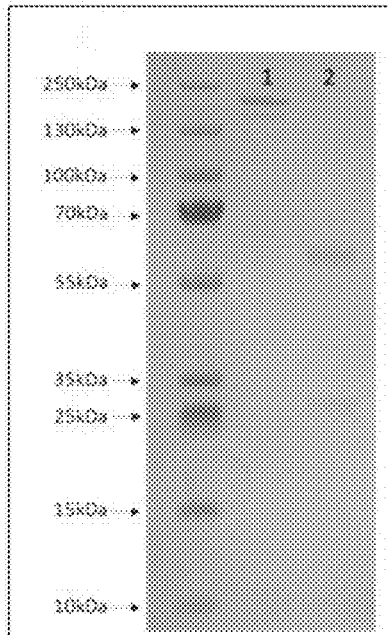
Figure 21B
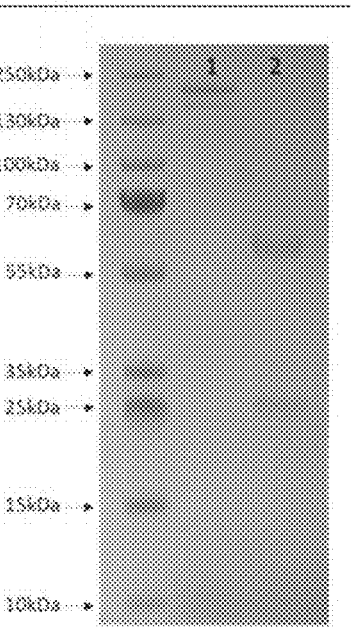
Figure 21C
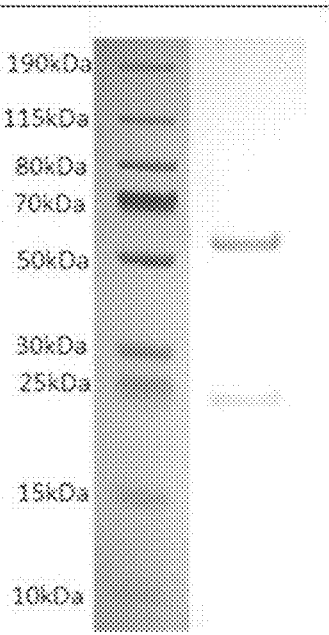
Figure 21D
| | Chimeric antibody | Humanised antibody | Humanised A33 | KLH |
|---|---|---|---|---|
| Donor 1 | | | | p |
| Donor 2 | p | | | p |
| Donor 3 | p | | p* | p |
| Donor 4 | | | | p |
| Donor 5 | | | | p |
| Donor 6 | p | | p | p |
| Donor 7 | | | | p |
| Donor 8 | | | p* | p |
| Donor 9 | | | | |
| Donor 10 | | | | p |
| Donor 11 | | | | p |
| Donor 12 | | | p | p |
| Donor 13 | | | | p |
| Donor 14 | | | | p |
| Donor 15 | | | | p |
| Donor 16 | | | | |
| Donor 17 | | | | |
| Donor 18 | | | | p |
| Donor 19 | | | | p |
| Donor 20 | p* | | | |
| Proliferation % | 20 | 0 | 20 | 80 |

Figure 22

| Species | Sequence | % |
|---|---|---|
| Human (SEQ ID NO: 30) | GNKLQVLGKDLLLPQ | |
| Vervet and Macaque (SEQ ID NO: 32) | GNKLQELGKDLLVPQ | 87% |
| Mouse (SEQ ID NO: 33) | GNRLQRLEDSLLAPQ | 60% |
| Rat (SEQ ID NO: 34) | GNRLQRLEAGLLAPQ | 60% |
| Guinea Pig (SEQ ID NO: 35) | GNRLQVLEEDLLSPQ | 73% |
| Chicken (SEQ ID NO: 36) | GNQLRALPPTLFAPT | 40% |
| Pig (SEQ ID NO: 37) | GNRLQVLEEGFLAPQ | 60% |
| Sheep (SEQ Id NO: 38) | GNRLRVLGEGLLAPQ | 67% |
| Cat (SEQ ID NO: 39) | GNRLSQLPVELLEPL | 47% |
| Dog (SEQ ID NO: 40) | GNRLQVLEEGLLAPQ | 67% |
| Cow (SEQ ID NO: 41) | GNRLQVLGEGLLAPQ | 73% |
| Zebrafish (SEQ ID NO: 42) | QNKIQTLDVKAFSGS | 27% |

Horse, rabbit and hamster not yet annotated

```
                        SEQUENCE LISTING

<160> NUMBER OF SEQ ID NOS: 42

<210> SEQ ID NO 1
<211> LENGTH: 118
<212> TYPE: PRT
<213> ORGANISM: Artificial Sequence
<220> FEATURE:
<223> OTHER INFORMATION: 15C4 Variable Heavy Chain

<400> SEQUENCE: 1

Gln Val Gln Leu Gln Gln Ser Gly Asp Glu Val Val Arg Pro Gly Ser
1               5                   10                  15

Ser Val Lys Ile Ser Cys Lys Ala Ser Gly Tyr Thr Phe Ser Gly Tyr
            20                  25                  30

Trp Met Asn Trp Val Lys Gln Arg Pro Gly Gln Gly Leu Gln Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Thr Leu Thr Ser Glu Asp Ser Ala Ile Tyr Phe Cys
                85                  90                  95

Ala Arg Ser Ile Thr Thr Val Val Leu Asp Tyr Trp Gly Gln Gly Thr
            100                 105                 110

Thr Leu Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: 15C4 Variable light chain

<400> SEQUENCE: 2

Asp Ile Val Leu Thr Gln Ser Pro Val Ser Leu Ala Val Ser Leu Gly
1               5                   10                  15

Gln Arg Ala Thr Ile Ser Cys Arg Ala Ser Gln Ser Val Ser Thr Ser
            20                  25                  30

Gly Tyr Ser Phe Met His Trp Tyr Gln Gln Lys Pro Gly Gln Pro Pro
        35                  40                  45

Lys Phe Leu Ile Lys Tyr Ala Ser Asn Leu Glu Ser Gly Val Pro Ala
    50                  55                  60
```

```
Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                 85                  90                  95

Glu Met Pro Leu Thr Phe Gly Ala Gly Thr Lys Leu Glu Leu Lys
            100                 105                 110

<210> SEQ ID NO 3
<211> LENGTH: 354
<212> TYPE: DNA
<213> ORGANISM: Artificial Sequence
<220> FEATURE:
<223> OTHER INFORMATION: 15C4 Variable heavy chain

<400> SEQUENCE: 3
caggttcaac tgcagcagtc tggggatgag gtggtgaggc ctgggtcctc agtgaagatt        60
tcctgtaagg cttctggcta tacattcagt ggctactgga tgaactgggt gaaacagagg       120
cctggacagg gtcttcagtg gattggacag atttatcctg agatggtga  tactaactac       180 aatggaaaat tcaagggtaa agccacactg actgcagaca atcctccag  cacagcctac       240 atgcagctca gcaccctaac atctgaggac tctgcgatct atttctgtgc aagatcgatt       300
actacggtag tccttgacta ctggggccaa ggcaccactc tcacagtctc ctca             354

<210> SEQ ID NO 4
<211> LENGTH: 333
<212> TYPE: DNA
<213> ORGANISM: Artificial Sequence
<220> FEATURE:
<223> OTHER INFORMATION: 15C4 Variable light chain

<400> SEQUENCE: 4
gacattgtgc tgacacagtc tcctgtttcc ttagctgtat ctctgggtca gagggccacc        60
atctcatgca gggccagcca aagtgtcagt acatctggct atagttttat gcactggtac       120
caacagaaac caggacagcc acccaaattc ctcatcaagt atgcatccaa cctagaatct       180
ggggtccctg ccaggttcag tggcagtggg tctgggacag acttcaccct caacatccat       240
cctgtggagg aggaggatac tgcaacatat tactgtcagc acagttggga gatgcctctc       300
acgttcggtg ctgggaccaa gctggagctg aaa                                    333

<210> SEQ ID NO 5
<211> LENGTH: 118
<212> TYPE: PRT
<213> ORGANISM: Artificial Sequence
<220> FEATURE:
<223> OTHER INFORMATION: Humanised 15C4 Variable heavy chain VH1

<400> SEQUENCE: 5

Gln Val Gln Leu Val Gln Ser Gly Asp Glu Val Lys Lys Pro Gly Ser
  1               5                  10                  15

Ser Val Lys Val Ser Cys Lys Ala Ser Gly Tyr Thr Phe Ser Gly Tyr
                 20                  25                  30

Trp Met Asn Trp Val Lys Gln Ala Pro Gly Gln Gly Leu Gln Trp Ile
             35                  40                  45

Gly Gln Ile Tyr Pro Gly Asp Gly Asp Thr Asn Tyr Asn Gly Lys Phe
         50                  55                  60

Lys Gly Arg Ala Thr Ile Thr Ala Asp Lys Ser Thr Ser Thr Ala Tyr
 65                  70                  75                  80
```

```
Met Gln Leu Ser Thr Leu Thr Ser Glu Asp Ser Ala Ile Tyr Phe Cys
            85                  90                  95

Ala Arg Ser Ile Thr Thr Val Val Leu Asp Tyr Trp Gly Gln Gly Thr
            100                 105                 110

Thr Val Thr Val Ser Ser
        115

<210> SEQ ID NO 6
<211> LENGTH: 390
<212> TYPE: DNA
<213> ORGANISM: Artificial Sequence
<220> FEATURE:
<223> OTHER INFORMATION: Humanised 15C4 Variable heavy chain VH1

<400> SEQUENCE: 6
gttgctacgc gtgtccactc ccaggttcaa ctggtgcagt ctggggatga ggtgaagaag      60
cctgggtcct cagtgaaggt gtcctgtaag gcttctggct atacattcag tggctactgg     120
atgaactggg tgaaacaggc ccctggacag ggtcttcagt ggattggaca gatttatcct     180
ggagatggtg atactaacta caatggaaaa ttcaagggtc gggccacaat cactgccgac     240
aaatccacca gcacagccta catgcagctc agcaccctaa catctgagga ctctgcgatc     300
tatttctgtg caagatcgat tactacggta gtccttgact actggggcca aggcaccacc     360
gtcacggtct cctcaggtaa gctttctggg                                       390

<210> SEQ ID NO 7
<211> LENGTH: 118
<212> TYPE: PRT
<213> ORGANISM: Artificial Sequence
<220> FEATURE:
<223> OTHER INFORMATION: Humanised 15c4 Variable heavy chain VH2

<400> SEQUENCE: 7

Gln Val Gln Leu Val Gln Ser Gly Asp Glu Val Lys Lys Pro Gly Ser
1               5                   10                  15

Ser Val Lys Val Ser Cys Lys Ala Ser Gly Tyr Thr Phe Ser Gly Tyr
            20                  25                  30

Trp Met Asn Trp Val Lys Gln Ala Pro Gly Gln Gly Leu Gln Trp Ile
        35                  40                  45

Gly Gln Ile Tyr Pro Gly Asp Gly Asp Thr Asn Tyr Asn Gly Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Thr Ser Glu Asp Thr Ala Ile Tyr Phe Cys
            85                  90                  95

Ala Arg Ser Ile Thr Thr Val Val Leu Asp Tyr Trp Gly Gln Gly Thr
            100                 105                 110

Thr Val Thr Val Ser Ser
        115

<210> SEQ ID NO 8
<211> LENGTH: 390
<212> TYPE: DNA
<213> ORGANISM: Artificial Sequence
<220> FEATURE:
<223> OTHER INFORMATION: Humanised 15C4 Variable heavy chain VH2

<400> SEQUENCE: 8
gttgctacgc gtgtccactc ccaggttcaa ctggtgcagt ctggggatga ggtgaagaag      60
```

```
cctgggtcct cagtgaaggt gtcctgtaag gcttctggct atacattcag tggctactgg    120
atgaactggg tgaaacaggc ccctggacag ggtcttcagt ggattggaca gatttatcct    180
ggagatggtg atactaacta caatggaaaa ttcaagggtc gggccacaat cactgccgac    240
aaatccacca gcacagccta catggagctc agctccctaa catctgagga caccgcgatc    300
tatttctgtg caagatcgat tactacggta gtccttgact actggggcca aggcaccacc    360
gtcacggtct cctcaggtaa gctttctggg                                      390
```

<210> SEQ ID NO 9
<211> LENGTH: 118
<212> TYPE: PRT
<213> ORGANISM: Artificial Sequence
<220> FEATURE:
<223> OTHER INFORMATION: Humanised 15C4 Variable heavy chain VH3

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Gly Tyr
            20                  25                  30

Trp Met Asn Trp Val Arg Gln Ala Pro Gly Gln Gly Leu Gln Trp Ile
        35                  40                  45

Gly Gln Ile Tyr Pro Gly Asp Gly Asp Thr Asn Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Ile Tyr Phe Cys
                85                  90                  95

Ala Arg Ser Ile Thr Thr Val Val Leu Asp Tyr Trp Gly Gln Gly Thr
            100                 105                 110

Thr Val Thr Val Ser Ser
        115
```

<210> SEQ ID NO 10
<211> LENGTH: 390
<212> TYPE: DNA
<213> ORGANISM: Artificial Sequence
<220> FEATURE:
<223> OTHER INFORMATION: Humanised 15C4 Variable heavy chain VH3

<400> SEQUENCE: 10

```
gttgctacgc gtgtccactc ccaggttcaa ctggtgcagt ctggggctga ggtgaagaag    60
cctgggtcct cagtgaaggt gtcctgtaag gcttctggct atacattcag tggctactgg    120
atgaactggg tgcggcaggc ccctggacag ggtcttcagt ggattggaca gatttatcct    180
ggagatggtg atactaacta caatggaaaa ttcaagggta gagtgacaat cactgccgac    240
aaatccacca gcacagccta catggagctc agctccctaa catctgagga caccgcgatc    300
tatttctgtg caagatcgat tactacggta gtccttgact actggggcca aggcaccacg    360
gtcaccgtct cctcaggtaa gctttctggg                                      390
```

<210> SEQ ID NO 11
<211> LENGTH: 118
<212> TYPE: PRT
<213> ORGANISM: Artificial Sequence
<220> FEATURE:
<223> OTHER INFORMATION: Humanised 15C4 Variable heavy chain VH4

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Gly Tyr
            20                  25                  30

Trp Met Asn Trp Val Arg Gln Ala Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Ile Tyr Tyr Cys
                85                  90                  95

Ala Arg Ser Ile Thr Thr Val Val Leu Asp Tyr Trp Gly Gln Gly Thr
            100                 105                 110

Thr Val Thr Val Ser Ser
        115
```

<210> SEQ ID NO 12
<211> LENGTH: 390
<212> TYPE: DNA
<213> ORGANISM: Artificial Sequence
<220> FEATURE:
<223> OTHER INFORMATION: Humanised 15C4 Variable heavy chain VH4

<400> SEQUENCE: 12

```
gttgctacgc gtgtccactc ccaggttcaa ctggtgcagt ctggggctga ggtgaagaag    60
cctgggtcct cagtgaaggt gtcctgtaag gcttctggct atacattcag tggctactgg   120
atgaactggg tgcggcaggc ccctggacag ggtcttgagt ggattggaca gatttatcct   180
ggagatggtg atactaacta caatggaaaa ttcaagggta gagtgacaat cactgccgac   240
aaatccacca gcacagccta catggagctc agctccctaa catctgagga caccgcgatc   300
tattactgtg caagatcgat tactacggta gtccttgact actggggcca aggcaccacg   360
gtcaccgtct cctcaggtaa gctttctggg                                    390
```

<210> SEQ ID NO 13
<211> LENGTH: 118
<212> TYPE: PRT
<213> ORGANISM: Artificial Sequence
<220> FEATURE:
<223> OTHER INFORMATION: Humanised 15C4 Variable heavy chain VH5

<400> SEQUENCE: 13

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Gly Tyr
            20                  25                  30

Trp Met Asn Trp Val Arg Gln Ala Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Thr Thr Val Val Leu Asp Tyr Trp Gly Gln Gly Thr
            100                 105                 110
```

Thr Val Thr Val Ser Ser
        115

<210> SEQ ID NO 14
<211> LENGTH: 390
<212> TYPE: DNA
<213> ORGANISM: Artificial Sequence
<220> FEATURE:
<223> OTHER INFORMATION: Humanised 15C4 Variable heavy chain VH5

<400> SEQUENCE: 14
gttgctacgc gtgtccactc ccaggttcaa ctggtgcagt ctggggctga ggtgaagaag     60
cctgggtcct cagtgaaggt gtcctgtaag gcttctggct atacattcag tggctactgg    120
atgaactggg tgcggcaggc ccctggacag ggtcttgagt ggattggaca gatttatcct    180
ggagatggtg atactaacta caatggaaaa ttcaagggta gagtgacaat cactgccgac    240
aaatccacca gcacagccta catggagctc agctccctac ggtctgagga caccgcggtg    300
tattactgtg caagatcgat tactacggta gtccttgact actggggcca aggcaccacg    360
gtcaccgtct cctcaggtaa gctttctggg                                     390

<210> SEQ ID NO 15
<211> LENGTH: 111
<212> TYPE: PRT
<213> ORGANISM: Artificial Sequence
<220> FEATURE:
<223> OTHER INFORMATION: Humanised 15C4 Variable light chain VK1

<400> SEQUENCE: 15

Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Gly Tyr Ser Phe Met His Trp Tyr Gln Gln Lys Pro Gly Gln Pro Pro
        35                  40                  45

Lys Phe Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Glu Glu Asp Phe Ala Thr Tyr Tyr Cys Gln His Ser Trp
                85                  90                  95

Glu Met Pro Leu Thr Phe Gly Gln Gly Thr Lys Leu Glu Ile Lys
            100                 105                 110

<210> SEQ ID NO 16
<211> LENGTH: 393
<212> TYPE: DNA
<213> ORGANISM: Artificial Sequence
<220> FEATURE:
<223> OTHER INFORMATION: Humanised 15C4 Variable light chain VK1

<400> SEQUENCE: 16
ctcccaggcg cgcgatgtga cattgtgctg acacagtctc ctgactcctt agctgtatct     60
ctgggtgaga gggccaccat ctcatgcagg gccagccaaa gtgtcagtac atctggctat    120
agttttatgc actggtacca acagaaacca ggacagccac ccaaattcct catcaagtat    180
gcatccaacc tagaatctgg ggtccctgcc aggttcagtg gcagtgggtc tgggacagac    240
ttcaccctca ccatctcttc tctgcaggag gaggatttcg caacatatta ctgtcagcac    300

```
agttgggaga tgcctctcac gttcggccag gggaccaagc tggagatcaa acgtgagtag    360
aatttaaact ttgcttcctc agttggatcc cgc                                 393
```

<210> SEQ ID NO 17
<211> LENGTH: 111
<212> TYPE: PRT
<213> ORGANISM: Artificial Sequence
<220> FEATURE:
<223> OTHER INFORMATION: Humanised 15C4 Variable light chain VK2

<400> SEQUENCE: 17

```
Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Gly Tyr Ser Phe Met His Trp Tyr Gln Gln Lys Pro Gly Gln Pro Pro
        35                  40                  45

Lys Phe Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Met Pro Leu Thr Phe Gly Gln Gly Thr Lys Leu Glu Ile Lys
            100                 105                 110
```

<210> SEQ ID NO 18
<211> LENGTH: 393
<212> TYPE: DNA
<213> ORGANISM: Artificial Sequence
<220> FEATURE:
<223> OTHER INFORMATION: Humanised 15C4 Variable light chain VK2

<400> SEQUENCE: 18

```
ctcccaggcg cgcgatgtga cattgtgctg acacagtctc ctgactcctt agctgtatct     60
ctgggtgaga gggccaccat ctcatgcagg gccagccaaa gtgtcagtac atctggctat    120
agttttatgc actggtacca acagaaacca ggacagccac ccaaattcct catcaagtat    180
gcatccaacc tagaatctgg ggtccctgcc aggttcagtg gcagtgggtc tgggacagac    240
ttcaccctca ccatctcttc tctgcagccc gaggatttcg caacatatta ctgtcagcac    300
agttgggaga tgcctctcac gttcggccag gggaccaagc tggagatcaa acgtgagtag    360
aatttaaact ttgcttcctc agttggatcc cgc                                 393
```

<210> SEQ ID NO 19
<211> LENGTH: 111
<212> TYPE: PRT
<213> ORGANISM: Artificial Sequence
<220> FEATURE:
<223> OTHER INFORMATION: Humanised 15C4 Variable light chain VK3

<400> SEQUENCE: 19

```
Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
```

```
                50                  55                  60
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Trp
                 85                  90                  95

Glu Met Pro Leu Thr Phe Gly Gln Gly Thr Lys Leu Glu Ile Lys
            100                 105                 110

<210> SEQ ID NO 20
<211> LENGTH: 393
<212> TYPE: DNA
<213> ORGANISM: Artificial Sequence
<220> FEATURE:
<223> OTHER INFORMATION: Humanised 15C4 Variable light chain VK3

<400> SEQUENCE: 20
ctcccaggcg cgcgatgtga cattgtgctg acacagtctc ctgactcctt agctgtatct    60
ctgggtgaga gggccaccat ctcatgcagg gccagccaaa gtgtcagtac atctggctat   120
agttttatgc actggtacca acagaaacca ggacagccac ccaaactgct catcaagtat   180
gcatccaacc tagaatctgg ggtccctgcc aggttcagtg gcagtgggtc tgggacagac   240 ttcacccctca ccatctcttc tctgcagccc gaggatttcg caacatatta ctgtcagcac   300
agttgggaga tgcctctcac gttcggccag gggaccaagc tggagatcaa acgtgagtag   360
aatttaaact ttgcttcctc agttggatcc cgc                                393

<210> SEQ ID NO 21
<211> LENGTH: 5
<212> TYPE: PRT
<213> ORGANISM: Artificial Sequence
<220> FEATURE:
<223> OTHER INFORMATION: Humanised 15C4 VH CDR1

<400> SEQUENCE: 21

Gly Tyr Trp Met Asn
 1               5

<210> SEQ ID NO 22
<211> LENGTH: 17
<212> TYPE: PRT
<213> ORGANISM: Artificial Sequence
<220> FEATURE:
<223> OTHER INFORMATION: Humanised 15C4 VH CDR2

<400> SEQUENCE: 22

Gln Ile Tyr Pro Gly Asp Gly Asp Thr Asn Tyr Asn Gly Lys Phe Lys
 1               5                  10                  15

Gly

<210> SEQ ID NO 23
<211> LENGTH: 9
<212> TYPE: PRT
<213> ORGANISM: Artificial Sequence
<220> FEATURE:
<223> OTHER INFORMATION: Humanised 15C4 VH CDR3

<400> SEQUENCE: 23

Ser Ile Thr Thr Val Val Leu Asp Tyr
 1               5

<210> SEQ ID NO 24
<211> LENGTH: 15
```

<212> TYPE: PRT
<213> ORGANISM: Artificial Sequence
<220> FEATURE:
<223> OTHER INFORMATION: Humanised 15C4 VL CDR1

<400> SEQUENCE: 24

Arg Ala Ser Gln Ser Val Ser Thr Ser Gly Tyr Ser Phe Met His
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Humanised 15C4 VL CDR2

<400> SEQUENCE: 25

Tyr Ala Ser Asn Leu Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Humanised 15C4 VL CDR3

<400> SEQUENCE: 26

Gln His Ser Trp Glu Met Pro Leu Thr
1               5

<210> SEQ ID NO 27
<211> LENGTH: 326
<212> TYPE: PRT
<213> ORGANISM: Artificial Sequence
<220> FEATURE:
<223> OTHER INFORMATION: Constant heavy chain

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

```
Ser Thr Tyr Arg Val Val Ser Val Leu Thr Val Leu His Gln Asp Trp
                180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 28
<211> LENGTH: 330
<212> TYPE: PRT
<213> ORGANISM: Artificial Sequence
<220> FEATURE:
<223> OTHER INFORMATION: Constant heavy chain

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 29
<211> LENGTH: 106
<212> TYPE: PRT
<213> ORGANISM: Artificial Sequence
<220> FEATURE:
<223> OTHER INFORMATION: Constant light chain

<400> SEQUENCE: 29

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 30
<211> LENGTH: 15
<212> TYPE: PRT
<213> ORGANISM: Artificial Sequence
<220> FEATURE:
<223> OTHER INFORMATION: Epitope

<400> SEQUENCE: 30

```
Gly Asn Lys Leu Gln Val Leu Gly Lys Asp Leu Leu Leu Pro Gln
1               5                   10                  15
```

<210> SEQ ID NO 31
<211> LENGTH: 347
<212> TYPE: PRT
<213> ORGANISM: Artificial Sequence
<220> FEATURE:
<223> OTHER INFORMATION: Human Lrg1

<400> SEQUENCE: 31

```
Met Ser Ser Trp Ser Arg Gln Arg Pro Lys Ser Pro Gly Gly Ile Gln
```

```
            1               5                   10                  15
        Pro His Val Ser Arg Thr Leu Phe Leu Leu Leu Leu Ala Ala Ser
                        20                  25                  30
        Ala Trp Gly Val Thr Leu Ser Pro Lys Asp Cys Gln Val Phe Arg Ser
                        35                  40                  45
        Asp His Gly Ser Ser Ile Ser Cys Gln Pro Pro Ala Glu Ile Pro Gly
                    50                  55                  60
        Tyr Leu Pro Ala Asp Thr Val His Leu Ala Val Glu Phe Phe Asn Leu
         65                 70                  75                  80
        Thr His Leu Pro Ala Asn Leu Leu Gln Gly Ala Ser Lys Leu Gln Glu
                            85                  90                  95
        Leu His Leu Ser Ser Asn Gly Leu Glu Ser Leu Ser Pro Glu Phe Leu
                        100                 105                 110
        Arg Pro Val Pro Gln Leu Arg Val Leu Asp Leu Thr Arg Asn Ala Leu
                        115                 120                 125
        Thr Gly Leu Pro Pro Gly Leu Phe Gln Ala Ser Ala Thr Leu Asp Thr
                    130                 135                 140
        Leu Val Leu Lys Glu Asn Gln Leu Glu Val Leu Glu Val Ser Trp Leu
        145                 150                 155                 160
        His Gly Leu Lys Ala Leu Gly His Leu Asp Leu Ser Gly Asn Arg Leu
                            165                 170                 175
        Arg Lys Leu Pro Pro Gly Leu Leu Ala Asn Phe Thr Leu Leu Arg Thr
                        180                 185                 190
        Leu Asp Leu Gly Glu Asn Gln Leu Glu Thr Leu Pro Pro Asp Leu Leu
                        195                 200                 205
        Arg Gly Pro Leu Gln Leu Glu Arg Leu His Leu Glu Gly Asn Lys Leu
                    210                 215                 220
        Gln Val Leu Gly Lys Asp Leu Leu Leu Pro Gln Pro Asp Leu Arg Tyr
        225                 230                 235                 240
        Leu Phe Leu Asn Gly Asn Lys Leu Ala Arg Val Ala Ala Gly Ala Phe
                            245                 250                 255
        Gln Gly Leu Arg Gln Leu Asp Met Leu Asp Leu Ser Asn Asn Ser Leu
                        260                 265                 270
        Ala Ser Val Pro Glu Gly Leu Trp Ala Ser Leu Gly Gln Pro Asn Trp
                        275                 280                 285
        Asp Met Arg Asp Gly Phe Asp Ile Ser Gly Asn Pro Trp Ile Cys Asp
                    290                 295                 300
        Gln Asn Leu Ser Asp Leu Tyr Arg Trp Leu Gln Ala Gln Lys Asp Lys
        305                 310                 315                 320
        Met Phe Ser Gln Asn Asp Thr Arg Cys Ala Gly Pro Glu Ala Val Lys
                            325                 330                 335
        Gly Gln Thr Leu Leu Ala Val Ala Lys Ser Gln
                        340                 345

<210> SEQ ID NO 32
<211> LENGTH: 15
<212> TYPE: PRT
<213> ORGANISM: Artificial Sequence
<220> FEATURE:
<223> OTHER INFORMATION: Vervet and Macaque Lrg1 epitope

<400> SEQUENCE: 32

Gly Asn Lys Leu Gln Glu Leu Gly Lys Asp Leu Ile Val Pro Gln
1               5                   10                  15
```

```
<210> SEQ ID NO 33
<211> LENGTH: 15
<212> TYPE: PRT
<213> ORGANISM: Artificial Sequence
<220> FEATURE:
<223> OTHER INFORMATION: Mouse Lrg1 epitope

<400> SEQUENCE: 33

Gly Asn Arg Leu Gln Arg Leu Glu Asp Ser Leu Leu Ala Pro Gln
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Rat Lrg1 epitope

<400> SEQUENCE: 34

Gly Asn Arg Leu Gln Arg Leu Glu Ala Gly Leu Leu Ala Pro Gln
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Guinea Pig Lrg1 epitope

<400> SEQUENCE: 35

Gly Asn Arg Leu Gln Val Leu Glu Glu Asp Leu Leu Ser Pro Gln
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Chicken Lrg1 epitope

<400> SEQUENCE: 36

Gly Asn Gln Leu Arg Ala Leu Pro Pro Thr Leu Phe Ala Pro Thr
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Pig Lrg1 epitope

<400> SEQUENCE: 37

Gly Asn Arg Leu Gln Val Leu Glu Glu Gly Phe Leu Ala Pro Gln
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Sheep Lrg1 epitope

<400> SEQUENCE: 38

Gly Asn Arg Leu Arg Val Leu Gly Glu Gly Leu Leu Ala Pro Gln
1               5                   10                  15

<210> SEQ ID NO 39
```

```
<211> LENGTH: 15
<212> TYPE: PRT
<213> ORGANISM: Artificial Sequence
<220> FEATURE:
<223> OTHER INFORMATION: Cat Lrg1 epitope

<400> SEQUENCE: 39

Gly Asn Arg Leu Ser Gln Leu Pro Val Glu Leu Leu Glu Pro Leu
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Dog Lrg1 epitope

<400> SEQUENCE: 40

Gly Asn Arg Leu Gln Val Leu Glu Glu Gly Leu Leu Ala Pro Gln
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Cow Lrg1 epitope

<400> SEQUENCE: 41

Gly Asn Arg Leu Gln Val Leu Gly Glu Gly Leu Leu Ala Pro Gln
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Zebrafish Lrg1 epitope

<400> SEQUENCE: 42

Gln Asn Lys Ile Gln Thr Leu Asp Val Lys Ala Phe Ser Gly Ser
1               5                   10                  15
```

ANTIBODY WHICH BINDS LRG1 AND METHODS OF USE

CROSS REFERENCE TO RELATED APPLICATIONS

This application is a U.S. National Phase of International Application No. PCT/GB2016/050439, filed Feb. 22, 2016, which claims the benefit of priority of GB Patent Application No. 1503438.2, filed Feb. 27, 2015, the contents of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 251502011100SeqList.txt, date recorded: May 19, 2016, size: 31,995 bytes).

FIELD OF THE INVENTION

The present invention relates to antibodies that specifically bind to Leucine-rich alpha-2-glycoprotein 1 (LRG1), and in particular to human Lrg1.

BACKGROUND TO THE INVENTION

Aberrant remodelling of the retinal vasculature is a prominent feature of sight-threatening conditions such as diabetic retinopathy, retinal vein occlusion, retinopathy of prematurity, age-related macular degeneration and macular telangiectasia. These vascular changes manifest themselves as both new capillary growth from pre-existing retinal vessels (angiogenesis) and the development of vascular malformations of existing vessels (e.g. telangiectasia). This pathogenic vascular remodelling in these diseases is a major contributing factor to loss of vision.

Similar vascular pathology and dysfunction also accompanies tumour growth, where angiogenesis permits the enlargement and growth of solid tumours, and their metastatic spread.

Leucine-rich alpha-2-glycoprotein 1 (Lrg1 gene identifiers: HGNC: 29480; Entrez Gene: 116844; Ensembl: ENSG00000171236; UniProtKB: P02750) was identified in 1977 (Haupt & Baudner, 1977) and its primary structure determined in 1985 (Takahashi et al, 1985). Lrg1 is highly evolutionarily conserved between mice and humans, polyclonal antibodies to human Lrg1 are commercially available and there are reports of concomitant increases in the level of transforming growth factor beta 1 (TGFβ1), TGFβ receptor II (TGFβRII) and Lrg1 in certain diseases (Sun et al, 1995; Li et al, 2007). Other groups have identified Lrg1 as a biomarker of certain diseases (US 2005/0064516; WO 2008/092214) and as a ligand for cytochrome c (US 2007/0184503). Lynch et al. (2012) demonstrate that microRNA-335 (miR-335) targets Lrg1 leading to decreased migration and invasion of neuroblastoma cells by reducing the phosphorylation status of myosin light chain (MLC).

The present inventors have previously shown that Leucine-rich alpha-2-glycoprotein 1 is a drugable target for the modulation of pathogenic vascular remodelling, particularly in the eye and in tumours that exhibit vasculoproliferation. Therefore, the inventors predicted that antagonising Lrg1 may be useful in the treatment of conditions in which pathogenic vascular remodelling or pathogenic angiogenesis occurs, particularly in the eye in conditions such as neovascular AMD, diabetic retinopathy and retinopathy of prematurity (WO 2011/027129). Wang et al (2013), published by the Inventors, also discloses that Lrg1 is involved in vascular remodelling, and that blocking Lrg1 within the TGFβ signalling complex has the potential to divert TGFβ away from pathogenic vascularisation.

The inventors have also previously found that Lrg1 has a direct effect on neoplastic cells as well as immune cell function, and so may be used as a target in the treatment and/or prevention of cancer by directly affecting these cells. The inventors have demonstrated that targeting Lrg1 has a direct effect on neoplastic cells, and so targeting Lrg1 can also be used to treat and/or prevent cancer by this direct effect on cancer cells, specifically by down-regulating the proliferation of neoplastic cells, rather than by an effect on tumour vascularisation. They have also found that Lrg1 modifies immune cell properties that contribute to the pro-oncogenic environment (WO2013132267).

A hallmark of many cancers is a structurally and functionally abnormal vasculature, which reduces tumour perfusion and enhances hypoxia, invasion, and metastasis (Carmeliet and Jain, 2011). Vascular normalisation in tumours is a developing field, in order to improve the delivery of cytotoxic drugs and immunotherapy to the entire tumour, not just its periphery (Carmeliet and Jain, 2011) (Maes et al., 2014). For effective delivery of cytotoxics and immunotherapy properly perfused and matured blood vessels are required. In addition, hypoxia is a driver of metastasis, promoting poor cell junctions and migration of cancer cells into the circulation. Thus increasing the oxygenation of a tumour could act to reduce the probability that the tumour becomes metastatic. Hypoxia also has adverse effects on the host immune system rendering it less susceptible to immune responses. Any tumour with improved vasculature would become more amenable to treatment and reduce hypoxia. Therefore, there is a desire to identify agents that can normalise the vasculature of tumours.

Many diseases are characterised by the presence of hypoxic tissue, including ischemic heart disease, diabetes and several diseases of the eye. There is a drive to increase the oxygenation of tissues affected by these conditions, to normalise the vasculature, in order to achieve a clinical benefit.

SUMMARY OF THE INVENTION

The present inventors have now created antibodies that bind human Lrg1 with surprising characteristics. The present inventors have produced antibodies which are suitable for use in therapy. The antibodies of the invention have therapeutically and clinically relevant properties. The antibodies of the present invention specifically bind to human Lrg1.

An initial cohort of 102 mouse antibodies (mAbs) that bind to human Lrg1 was raised. Cross-species reactivity and binding kinetics analysis narrowed the field of potential therapeutic antibodies. The three lead antibodies, 15C4, 3A11 and 4H2 underwent in vitro an in vivo analyses to determine their therapeutic efficacy. The antibody 15C4 was sequenced and humanized.

The antibodies of the invention exhibit high affinity for human Lrg1, defined as 1 nM or less. In particular, the antibody 15C4 surprisingly exhibited affinity in the picomolar range, amounting to a near irreversible binding to Lrg1.

The antibodies of the invention cause a blockade of angiogenesis in the mouse and rat models of laser-induced choroidal neovascularisation (CNV). The antibodies of the invention cause a blockade in vessel growth in the Human umbilical vein endothelial cells (HUVEC) co-culture model of angiogenesis.

The antibodies of the invention exhibit lower cross-reactivity with Lrg1 from other organisms.

The present inventors have found that knocking out expression of Lrg1 in solid tumours causes a decrease in the number of small vessels in the tumours. This decrease is associated with a decrease in tumour size, a decrease in the number of proliferating cells in the tumours and an increase in pericyte coverage on the remaining vessels. Taken together, the results indicate that knocking out Lrg1 expression acts to restrict angiogenesis but also to normalise tumour vasculature.

Furthermore, the present inventors have also found that Lrg1 antagonists reduce tumour growth and normalise the vasculature of the remaining tumour. These data suggest that antagonists of Lrg1 could be used to reduce metastatic spread. Antagonists of Lrg1 could be used to improve the delivery and efficacy of anti-cancer and cytotoxic drugs/biologics to a tumour.

Normalisation of vasculature by Lrg1 antagonists would also allow for treatment of diseases where it would be useful to increase vascularisation. Treatment with a Lrg1 antagonist would reduce chaotic and immature vessel formation. Subsequent treatment with a pro-angiogenic agent would improve functional mature vascularisation. Such treatment would be used in any disease where tissues are affected by hypoxia or diseases where there are malformed blood vessels. Such diseases include, ischemia, ischemic heart disease, diabetes, ischemic stroke, vascular dementia, transient ischemic attack, mitral valve disease, chronic atrial fibrillation, cardiomyopathies, acute limb ischemia, peripheral limb ischemia, thrombosis, blood vessel occlusion, thoracic outlet syndrome, atherosclerosis, hypoglycaemia, tachycardia, hypotension, sickle cell disease, frostbite, arteriovenous malformations, blood vessel rupture and anemia.

Therefore, the invention provides:

An antibody or fragment thereof that specifically binds to human Lrg1 and which comprises at least one CDR selected from SEQ ID NOs: 21 to 26.

In another embodiment, an antibody or fragment thereof which comprises at least one CDR selected from SEQ ID NOs: 23 and 26.

In another embodiment, an antibody or fragment thereof wherein the antibody or fragment thereof comprises the CDRs of SEQ ID NOs: 23 and 26.

In another embodiment, an antibody or fragment thereof wherein the antibody or fragment thereof comprises the CDRs of:
 (a) SEQ ID NOs: 21, 22 and 23; or
 (b) SEQ ID NOs: 24, 25 and 26.

In another embodiment, an antibody or fragment thereof wherein the antibody or fragment thereof comprises the CDRs of SEQ ID NOs: 21, 22, 23, 24, 25 and 26.

In another embodiment, an antibody or fragment thereof wherein the antibody or fragment thereof comprises:
(a) a heavy chain variable region amino acid sequence of SEQ ID NO: 1, 5, 7, 9, 11 or 13;
(b) a fragment of at least 7 amino acids of (a), wherein the antibody or fragment retains the ability to specifically bind to Lrg1; or
(c) a variant of (a) having at least 70% amino acid sequence identity to a sequence of (a), wherein the antibody or fragment retains the ability to specifically bind to Lrg1.

In another embodiment, an antibody or fragment thereof wherein the antibody comprises:
(a) a light chain variable region amino acid sequence of SEQ ID NO: 2, 15, 17 or 19;
(b) a fragment of at least 7 amino acids of (a), wherein the antibody or fragment retains the ability to specifically bind to Lrg1; or
(c) a variant of (a) having at least 70% identity amino acid identity to a sequence of (a), wherein the antibody or fragment retains the ability to specifically bind to Lrg1.

In another embodiment, an antibody or fragment thereof according to any one the preceding claims, wherein the antibody comprises:
 (a) the heavy chain variable region of SEQ ID NO: 1 and the light chain variable region of SEQ ID NO: 2; or
 (b) the heavy chain variable region of SEQ ID NO: 1 and the light chain variable region of SEQ ID NO: 15; or
 (c) the heavy chain variable region of SEQ ID NO: 1 and the light chain variable region of SEQ ID NO: 17; or
 (d) the heavy chain variable region of SEQ ID NO: 1 and the light chain variable region of SEQ ID NO: 19; or
 (e) the heavy chain variable region of SEQ ID NO: 5 and the light chain variable region of SEQ ID NO: 2; or
 (f) the heavy chain variable region of SEQ ID NO: 5 and the light chain variable region of SEQ ID NO: 15; or
 (g) the heavy chain variable region of SEQ ID NO: 5 and the light chain variable region of SEQ ID NO: 17; or
 (h) the heavy chain variable region of SEQ ID NO: 5 and the light chain variable region of SEQ ID NO: 19; or
 (i) the heavy chain variable region of SEQ ID NO: 7 and the light chain variable region of SEQ ID NO: 2; or
 (j) the heavy chain variable region of SEQ ID NO: 7 and the light chain variable region of SEQ ID NO: 15; or
 (k) the heavy chain variable region of SEQ ID NO: 7 and the light chain variable region of SEQ ID NO: 17; or
 (l) the heavy chain variable region of SEQ ID NO: 7 and the light chain variable region of SEQ ID NO: 19; or
 (m) the heavy chain variable region of SEQ ID NO: 9 and the light chain variable region of SEQ ID NO: 2; or
 (n) the heavy chain variable region of SEQ ID NO: 9 and the light chain variable region of SEQ ID NO: 15; or
 (o) the heavy chain variable region of SEQ ID NO: 9 and the light chain variable region of SEQ ID NO: 17; or
 (p) the heavy chain variable region of SEQ ID NO: 9 and the light chain variable region of SEQ ID NO: 19; or
 (q) the heavy chain variable region of SEQ ID NO: 11 and the light chain variable region of SEQ ID NO: 2; or
 (r) the heavy chain variable region of SEQ ID NO: 11 and the light chain variable region of SEQ ID NO: 15; or
 (s) the heavy chain variable region of SEQ ID NO: 11 and the light chain variable region of SEQ ID NO: 17; or
 (t) the heavy chain variable region of SEQ ID NO: 11 and the light chain variable region of SEQ ID NO: 19; or
 (u) the heavy chain variable region of SEQ ID NO: 13 and the light chain variable region of SEQ ID NO: 2; or
 (v) the heavy chain variable region of SEQ ID NO: 13 and the light chain variable region of SEQ ID NO: 15; or
 (w) the heavy chain variable region of SEQ ID NO: 13 and the light chain variable region of SEQ ID NO: 17; or
 (x) the heavy chain variable region of SEQ ID NO: 13 and the light chain variable region of SEQ ID NO: 19.

In another embodiment, an antibody or fragment thereof that specifically binds to Lrg1, comprising the CDRs of SEQ ID NOs: 1, 5, 7, 9, 11 or 13 and/or the CDRs of SEQ ID NOs: 2, 15, 17 or 19.

In another embodiment, an antibody or fragment thereof that specifically binds to amino acids GNKLQVLG-KDLLLPQ (SEQ ID NO: 30) of Lrg1, and blocks Lrg1 activity.

The antibodies of the invention can also be used in the treatment of vasculoproliferative conditions. The antibodies of the invention can also be used in the treatment of cancer. The antibodies of the invention can be administered in combination with cytotoxic compounds or anti-cancer agents.

The Invention also concerns antagonists of Lrg1 in combination with anti-angiogenic agents for use in the treatment of cancer.

The Invention also concerns antagonists of Lrg1 in combination with pro-angiogenic agents for use in methods of revascularisation of a tissue in which the vasculature is malformed.

BRIEF DESCRIPTION OF THE SEQUENCE LISTING

SEQ ID NO: 1 is the amino acid sequence of variable region of the heavy chain of the antibody 15C4.

SEQ ID NO: 2 is the amino acid sequence of variable region of the light chain of the antibody 15C4.

SEQ ID NO: 3 is the nucleotide sequence of variable region of the heavy chain of the antibody 15C4.

SEQ ID NO: 4 is the nucleotide sequence of variable region of the light chain of the antibody 15C4.

SEQ ID NO: 5 is the amino acid sequence of variable region of the heavy chain of the variant VH1—a humanized variant of the variable region of the heavy chain of the antibody 15C4.

SEQ ID NO: 6 is the nucleotide sequence of variable region of the heavy chain of the variant VH1—a humanized variant of the variable region of the heavy chain of the antibody 15C4.

SEQ ID NO: 7 is the amino acid sequence of variable region of the heavy chain of the variant VH2—a humanized variant of the variable region of the heavy chain of the antibody 15C4.

SEQ ID NO: 8 is the nucleotide sequence of variable region of the heavy chain of the variant VH2—a humanized variant of the variable region of the heavy chain of the antibody 15C4.

SEQ ID NO: 9 is the amino acid sequence of variable region of the heavy chain of the variant VH3—a humanized variant of the variable region of the heavy chain of the antibody 15C4.

SEQ ID NO: 10 is the nucleotide sequence of variable region of the heavy chain of the variant VH3—a humanized variant of the variable region of the heavy chain of the antibody 15C4.

SEQ ID NO: 11 is the amino acid sequence of variable region of the heavy chain of the variant VH4—a humanized variant of the variable region of the heavy chain of the antibody 15C4.

SEQ ID NO: 12 is the nucleotide sequence of variable region of the heavy chain of the variant VH4—a humanized variant of the variable region of the heavy chain of the antibody 15C4.

SEQ ID NO: 13 is the amino acid sequence of variable region of the heavy chain of the variant VH5—a humanized variant of the variable region of the heavy chain of the antibody 15C4.

SEQ ID NO: 14 is the nucleotide sequence of variable region of the heavy chain of the variant VH5—a humanized variant of the variable region of the heavy chain of the antibody 15C4.

SEQ ID NO: 15 is the amino acid sequence of variable region of the light chain of the variant VK1—a humanized variant of the variable region of the light chain of the antibody 15C4.

SEQ ID NO: 16 is the nucleotide sequence of variable region of the light chain of the variant VK1—a humanized variant of the variable region of the light chain of the antibody 15C4.

SEQ ID NO: 17 is the amino acid sequence of variable region of the light chain of the variant VK2—a humanized variant of the variable region of the light chain of the antibody 15C4.

SEQ ID NO: 18 is the nucleotide sequence of variable region of the light chain of the variant VK2—a humanized variant of the variable region of the light chain of the antibody 15C4.

SEQ ID NO: 19 is the amino acid sequence of variable region of the light chain of the variant VK3—a humanized variant of the variable region of the light chain of the antibody 15C4.

SEQ ID NO: 20 is the nucleotide sequence of variable region of the light chain of the variant VK3—a humanized variant of the variable region of the light chain of the antibody 15C4.

SEQ ID NO: 21, 22 and 23 are CDRs 1, 2 and 3 respectively of the heavy chain of the antibodies described above.

SEQ ID NO: 24, 25 and 26 are the CDRs 1, 2 and 3 respectively of the light chain of the antibodies described above.

SEQ ID NO: 27 is the amino acid sequence of an exemplary heavy chain constant region.

SEQ ID NO: 28 is the amino acid sequence of an exemplary heavy chain constant region.

SEQ ID NO: 29 is the amino acid sequence of an exemplary light chain constant region.

SEQ ID NO: 30 is the amino acid sequence of an epitope of human Lrg1.

SEQ ID NO: 31 is the amino acid sequence of human Lrg1.

BRIEF DESCRIPTION OF THE FIGURES

FIG. 7: Anti-human Lrg1 competition ELISA.

A dilution series of test antibodies were competed against a fixed concentration of biotinylated mouse 15C4 for binding to recombinant human Lrg1. Bound biotinylated mouse 15C4 was detected using streptavidin-peroxidase conjugate and TMB substrate.

FIG. 9: Lrg1 and angiogenesis in B16/F0 and LL/2 tumours.

FIG. 10: Loss of Lrg1 results in increased pericyte coverage.

FIG. 11 (A) Total CD31 positive objects per mm$^2$. (B) Vessel size pooled according to cross-sectional fill-area per mm$^2$. (C) Percentage of vessels pooled according to size for 15C4 and IgG treated mice. Fewer small vessels were observed in the 15C4 treated tumours, as such a significant difference in the distribution of vessel sizes was observed compared to IgG controls (Two-Way ANOVA, P<0.0001).

FIG. 14—15C4 potentiates the cytotoxic activity of cisplatin: effect on tumour size. (A) B16/F0 tumours treated with 15C4 in combination with cisplatin exhibited a significant reduction in tumor growth compared with IgG and cisplatin controls (Two-Way ANOVA, P<0.005). (B) Tumours treated with 15C4 exhibited a similar rate of growth compared with IgG and vehicle controls.

FIG. 15—15C4 potentiates the cytotoxic activity of cisplatin: increased level of apoptosis. Cisplatin and IgG or 15C4 treated tumours were immersion fixed in 4% PFA overnight at 4° C. and then immersed in 30% sucrose overnight at 4° C. Tumour tissue was then OCT embedded and frozen for sectioning (40 μm). TUNEL assay was performed using an ApopTag in situ apoptosis detection kit according to manufacturers protocol (Merk Millipore, USA) (FIGS. 15A and 15B).

FIG. 16—15C4 potentiates the cytotoxic activity of cisplatin: increased level of apoptosis.

Figure 16A:
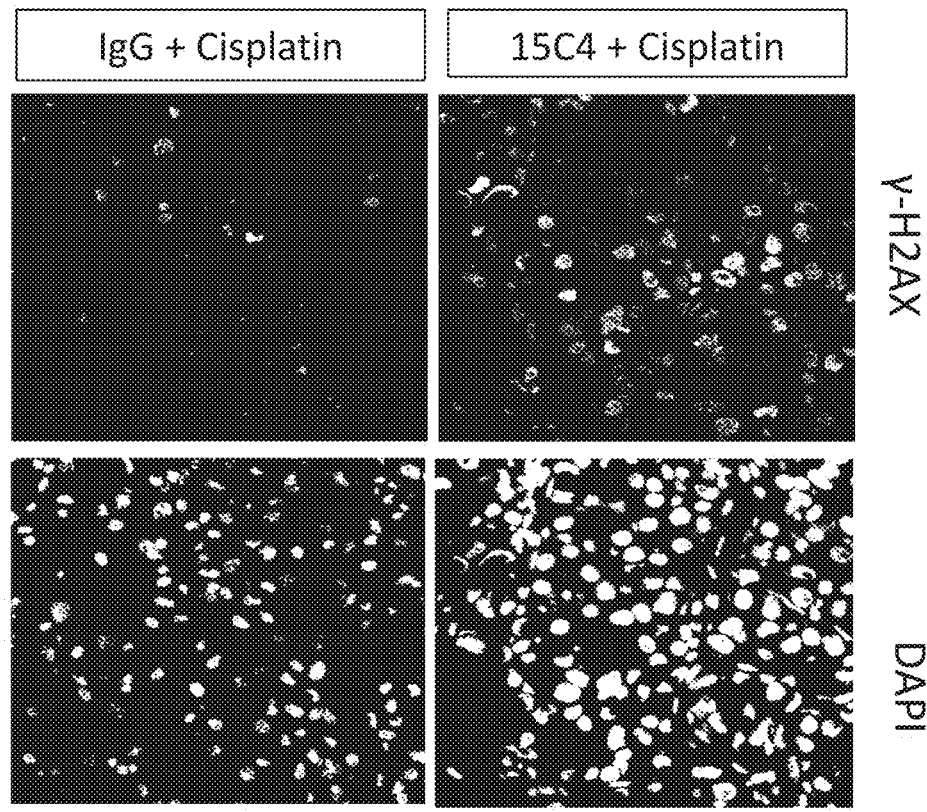
Figure 16B:
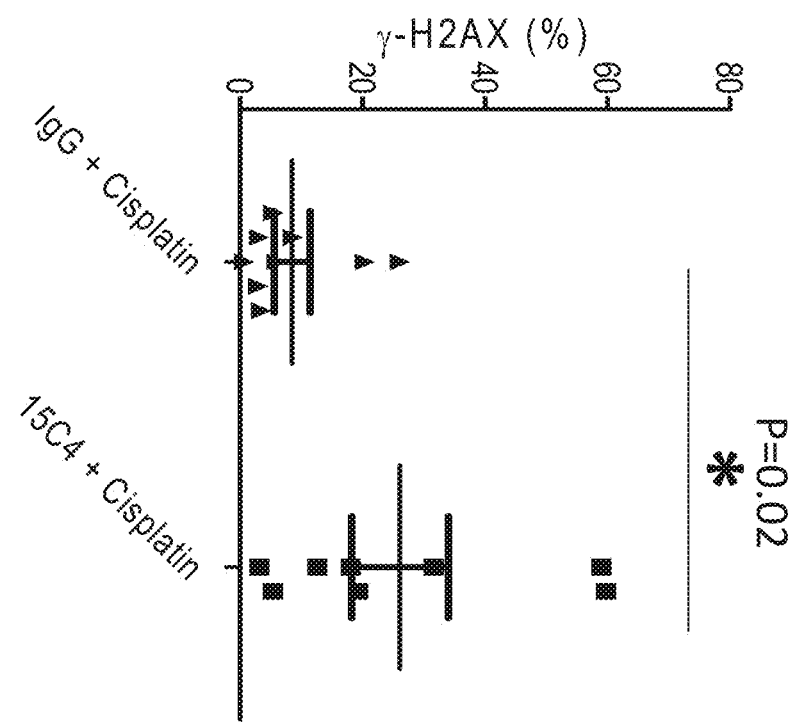

The DNA double strand break marker γ-H2AX was stained for in tumour sections, indicating cisplatin-induced DNA damage (FIG. 16A). Significantly more nuclei with γ-H2AX foci were observed in tumours treated with 15C4 in combination with cisplatin than in the IgG and cisplatin controls (FIG. 16B; one-tailed Student's T-test, P<0.05).

Figure 4:
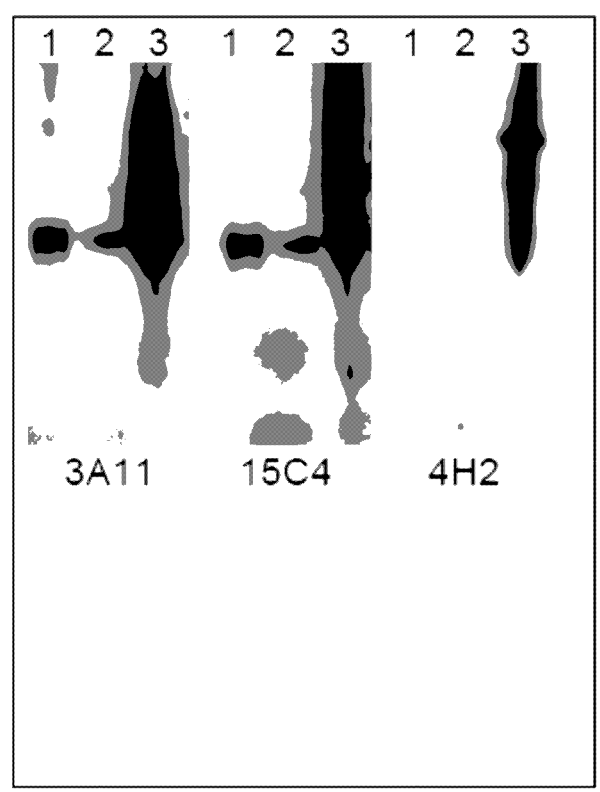
FIG. 4: Antibody specificity for target. mAbs 3A11, 15C4 and 4H2 were tested against samples of (1) conditioned medium from MDA-MB cells, (2) human vitreous and (3) whole human serum.
Figure 15A:
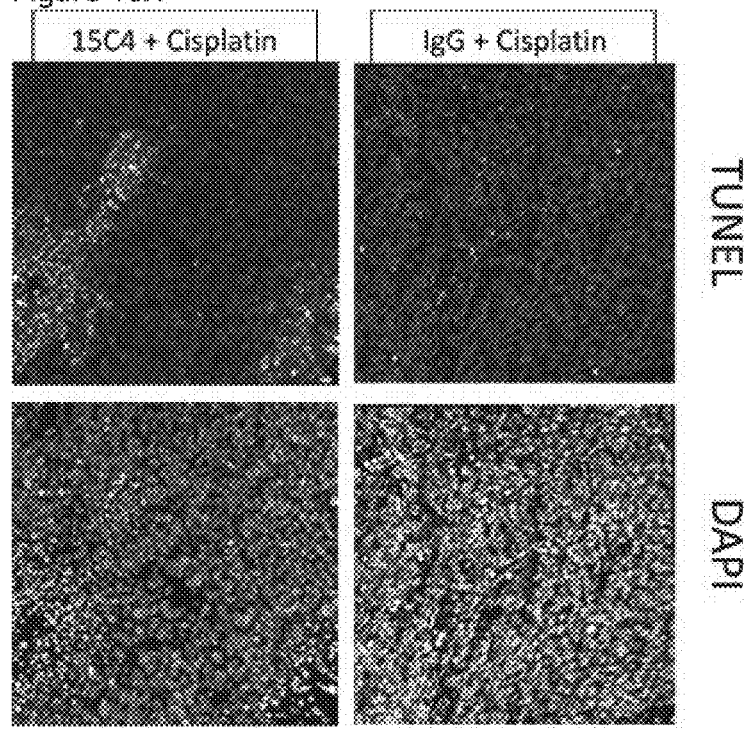
Figure 17A:
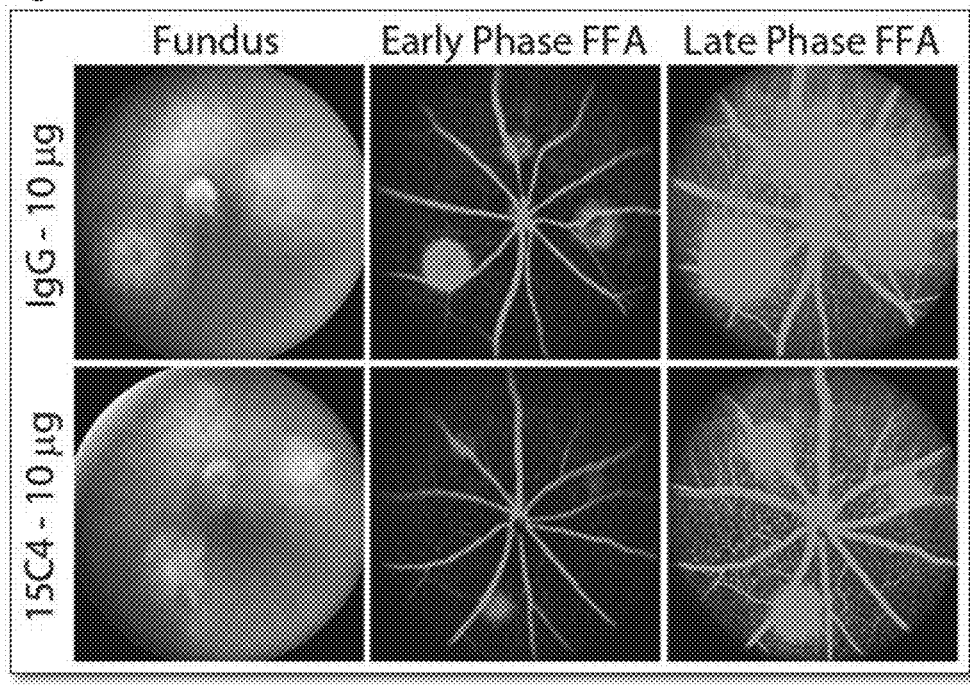
Figure 17B:
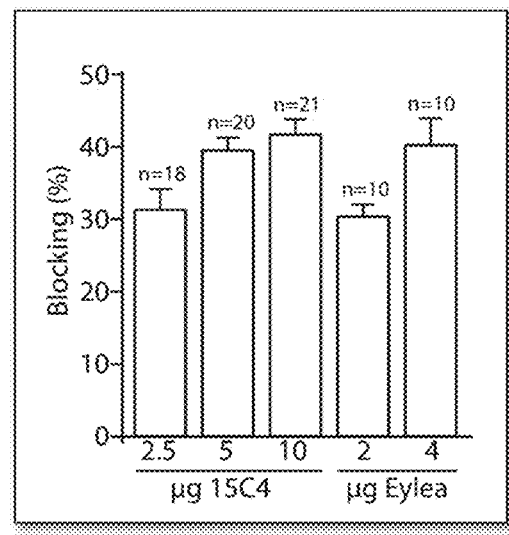
Figure 17C:
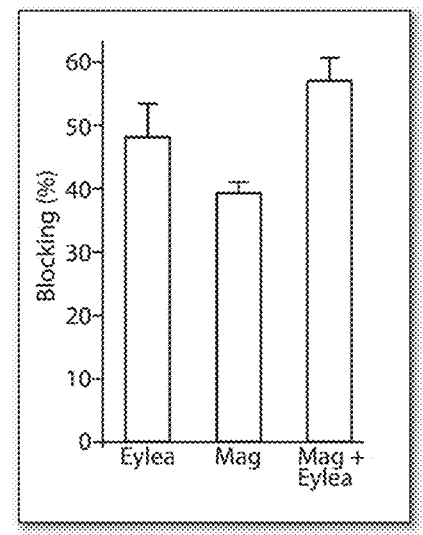

FIG. 17—15C4 inhibits lesion formation in the mouse model of laser-induced choroidal neovascularisation. FIG. 17A: The images on the left show a typical wild-type mouse retina under normal illumination (Fundus), and under fluorescence illumination, 7 days after three laser burns were administered to the retinal pigment epithelium. Fluorescence images were captured ~60 seconds after systemic dosing with fluorescein (Early Phase FFA) and again after ~7 minutes (Late Phase FFA). At the time of lasering, animals received intraocular injections of either control IgG (top panels) or 15C4 (lower panels). The Early Phase FFA images show the size of the lesions, and the Late Phase images show leakage of fluorescein into the retina. FIG. 17B: Lesion sizes were quantified for 15C4 at 2.5, 5 and 10 μg doses, and also Eylea at 2 and 4 μg, and the % blocking is a measure of average lesion size relative to that observed in the controls. FIG. 17C shows a similar analysis was undertaken using Eylea and Magacizumab (both at 2 μg) alone and in combination.

Figure 18:
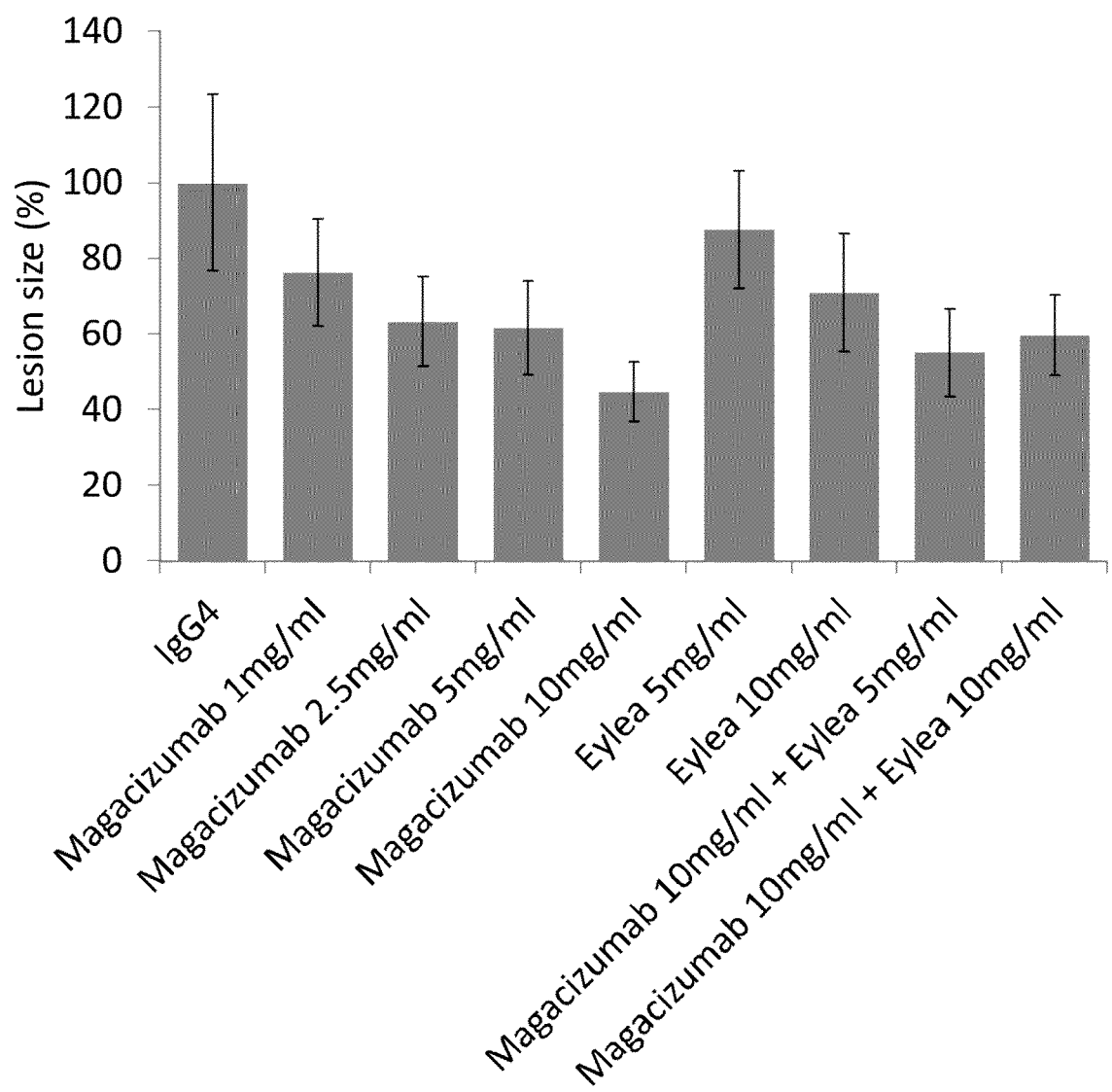

FIG. 18—Dose-dependent inhibition of lesion formation by Magacizumab in laser-induced CNV.

Wild type C57B6 mice were anaesthetized and received intravitreal injections of various doses of either Magacizumab, Eylea, or both in combination, immediately following laser photocoagulation of the retinal pigment epithelium. After 7 days (to allow the vascular lesions to form) the mice were again anaesthetized and examined by fluorescein angiography (FFA). Early phase FFA images (taken after 90 s) show the degree of vascularization at the lesion site. Measurement of the lesion area in the early phase images permits quantification in which percentage lesion size is normalized against the IgG4 control.

Figure 19A:
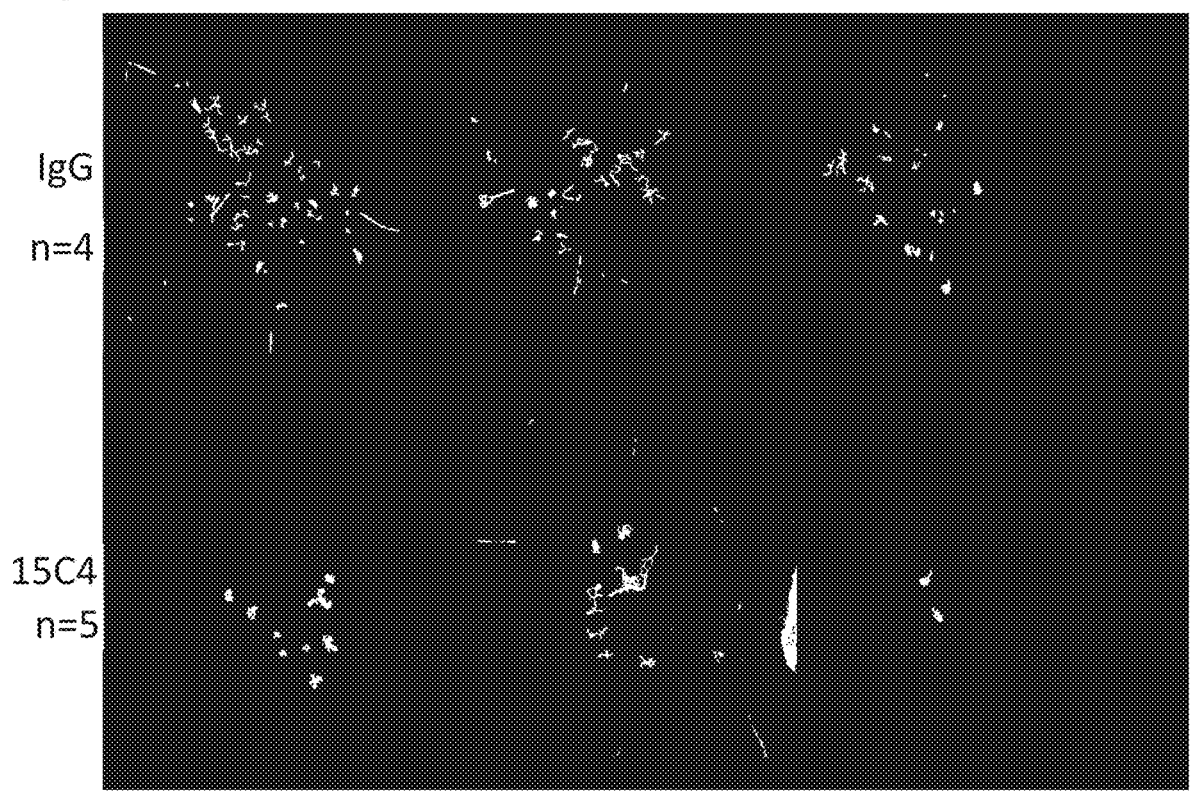
Figure 19B:
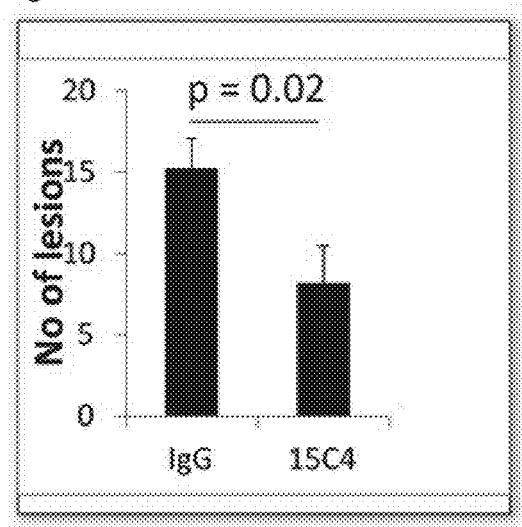

FIG. 19—15C4 reduces lesion formation in the JR5558 mouse (D14-D24) harvest D25. FIG. 19A: 15C4 or IgG at 50 mg/kg was administered IP every 3 days from D14. Eyes were harvested on D25 and RPE/Choroid stained with Collagen IV. The number of lesions was counted and data quantified for the two groups (FIG. 19B).

FIG. 20—Biochemical properties of Magacizumab

Figure 20A:
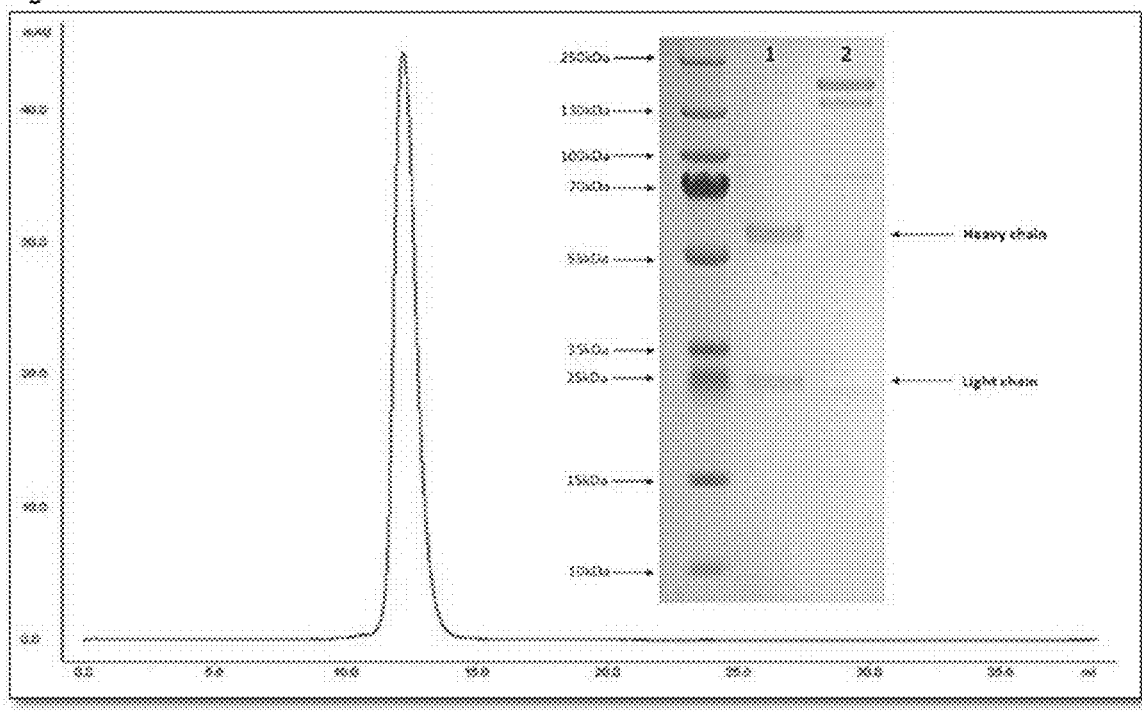
Figure 20B:
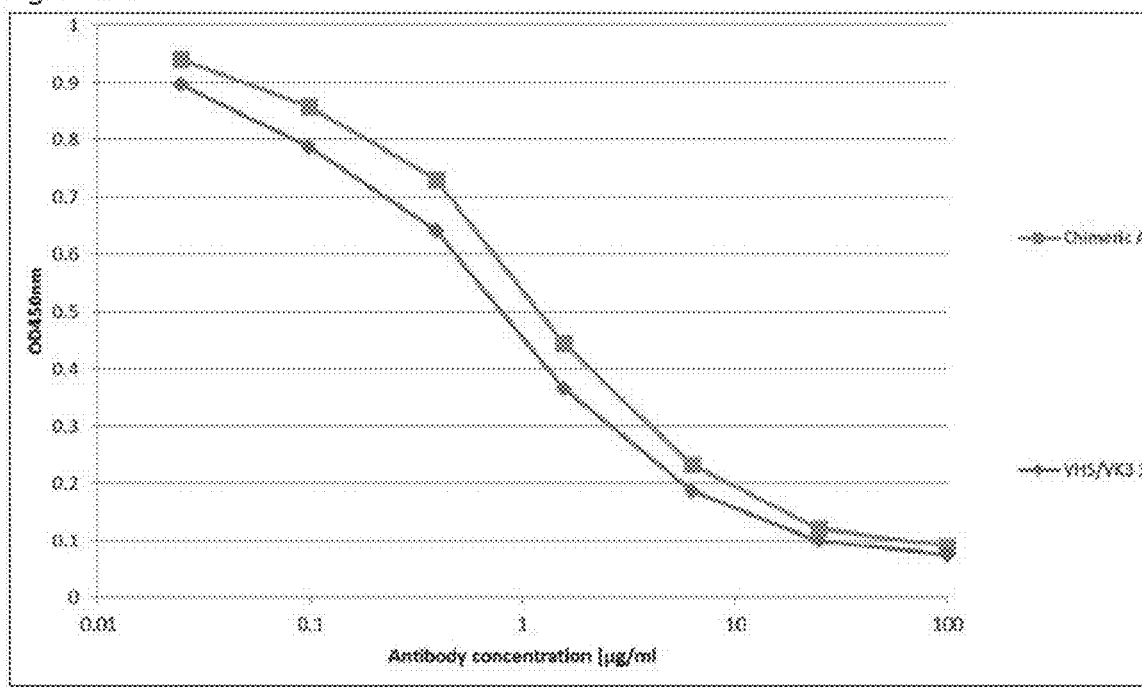

FIG. 20A—Analytical size exclusion chromatography showing single peak and no aggregates. SDS-PAGE showing reduced (lane 1) and non-reduced (lane 2) antibody. FIG. 20B—Anti-hLRG1 competition ELISA. A dilution series of each purified antibody was competed against a fixed concentration of biotinylated mouse 15C4 for binding to recombinant hLRG1. Bound biotinylated mouse 15C4 was detected using streptavidin-peroxidase and TMB substrate.

FIG. 21—De-immunisation of Magacizumab

SDS-PAGE gel of test and control antibodies. 1 µg of chimeric (FIG. 21A), fully humanised (FIG. 21B) or clinical benchmark control, humanised A33 (FIG. 21C) were run as non-reduced (for chimeric and humanised test antibodies only—lane 1) and reduced (lane 2) samples on NuPage 4-12% Bis-Tris gels (Invitrogen, Paisley, UK) at 200 V for 35 min. Gel was stained with InstantBlue (Expedeon, Cambridge, UK) and size markers (kDa) are prestained protein standard Fermentas PageRuler Plus (Thermo Scientific, Loughborough, UK).

FIG. 21D—Summary of healthy donor T cell proliferative responses. Positive T cell responses during EpiScreen™ time course days 5-8 are shown (P). Samples inducing proliferation with SI ≥2.00 that were significant (p<0.05) were considered positive (borderline responses* SI≥1.90, p<0.05 are also shown). The frequency of positive T cell responses for proliferation are shown as a percentage at the bottom of the columns.

FIG. 22—Invariant residues in the 15C4 epitope. Epitope conservation across vertebrate species. The LRG1 epitope recognised by 15C4 in human LRG1 was determined by peptide mapping using overlapping peptides. The figure shows alignment of this sequence with the orthologous regions of the LRG1 amino-acid sequence in a range of other species. Highly conserved residues are boxed, and the degree of sequence identity for each species relative to human is shown on the right. The information is relevant in the context of selection of suitable species for obligatory pre-clinical safety and toxicology studies of Magacizumab.

DETAILED DESCRIPTION OF THE INVENTION

The present invention relates to antibodies that bind to Lrg1. The invention also relates to uses for such antibodies, such as therapeutic uses. The antibodies preferably specifically bind to Lrg1, that is they bind to Lrg1 but they do not bind, or bind at a lower affinity, to other molecules. The term Lrg1 as used herein refers to human Lrg1. The sequence of human Lrg1 is set out in SEQ ID NO: 31. An antibody of the present invention may have some binding affinity for Lrg1 from other mammals, for example primate or murine e.g. mouse or rat Lrg1. The binding affinity of the antibodies of the invention for Lrg1 from other species becomes progressively weaker as the binding epitope becomes less conserved with phylogenetic distance.

Antibodies of the invention block the function of Lrg1. Blocking of Lrg1 encompasses any reduction in its activity or function that results in reduced vasculoproliferative effects, including endothelial cell proliferation, pericyte drop-out, endothelial cell death, vascular remodelling, angiogenesis, telangiectasia and vascular leakage.

For example, blocking of Lrg1 may be via blocking its interaction with ALK1, TGFβRII and/or TGFβ. Blocking of Lrg1 may also result in reduced bioavailability of TGFβ.

Blocking encompasses both total and partial reduction of Lrg1 activity or function, for example total or partial prevention of the ALK1-Lrg1, TGFβRII-Lrg1 and/or TGFβ-Lrg1 interactions. For example, a blocking antibody of the invention may reduce the activity of Lrg1 by from 10 to 50%, at least 50% or at least 70%, 80%, 90%, 95% or 99%.

Blocking of Lrg1 activity or function can be measured by any suitable means. For example, blocking of the ALK1-Lrg1, TGFβRII-Lrg1 and/or TGFβ-Lrg1 interaction can be determined by measuring the effect on Smad5 phosphorylation, on the basis that Smad5 phosphorylation is characteristic of the ALK1 activated pathway rather than the ALK5-activated one.

Blocking of Lrg1 can also be measured via assays that measure angiogenesis, for example in vitro assays such as vessel growth in Matrigel, vessel growth from aortic rings and in vivo assays such as those that measure retinal angiogenesis (eg laser induced choroidal neovascularisation, oxygen-induced retinopathy).

Blocking may take place via any suitable mechanism, e.g. any direct ALK1-Lrg1, TGFβRII-Lrg1 and/or TGFβ-Lrg1 interaction.

The terms "binding activity" and "binding affinity" are intended to refer to the tendency of an antibody molecule to bind or not to bind to a target. Binding affinity may be quantified by determining the dissociation constant (Kd) for an antibody and its target. Similarly, the specificity of binding of an antibody to its target may be defined in terms of the comparative dissociation constants (Kd) of the antibody for its target as compared to the dissociation constant with respect to the antibody and another, non-target molecule.

Typically, the Kd for the antibody with respect to the target will be 2-fold, preferably 5-fold, more preferably 10-fold less than Kd with respect to the other, non-target molecule such as unrelated material or accompanying material in the environment. More preferably, the Kd will be 50-fold less, even more preferably 100-fold less, and yet more preferably 200-fold less.

The value of this dissociation constant can be determined directly by well-known methods, and can be computed even for complex mixtures by methods such as those, for example, set forth in Caceci et al. (Byte 9:340-362, 1984). For example, the Kd may be established using a double-filter nitrocellulose filter binding assay such as that disclosed by Wong & Lohman (Proc. Natl. Acad. Sci. USA 90, 5428-5432, 1993).

One method for the evaluation of binding affinity for Lrg1 is by ELISA. Other standard assays to evaluate the binding ability of ligands such as antibodies towards targets are known in the art, including for example, Western blots, RIAs, and flow cytometry analysis. The binding kinetics (e.g., binding affinity) of the antibody also can be assessed by standard assays known in the art, such as surface plasmon resonance, for example by Biacore™ system analysis.

The binding affinity of an antibody of the invention to its target can be measured by methods known to the person skilled in the art, for example by surface plasmon resonance. A type of surface plasmon resonance is Biacore. Preferably the antibody of the invention has a binding affinity for Lrg1 of 1 nM or less. Preferably the antibody of the invention has a binding affinity for Lrg1 of 0.5 nM or less, 0.1 nM or less, 50 pM or less, 10 pM or less, 5 pM or less or 2 pM or less.

A competitive binding assay can be conducted in which the binding of the antibody to the target is compared to the binding of the target by another, known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

An antibody of the invention specifically binds to Lrg1. "Specifically binding" means that an antibody binds to Lrg1 with greater affinity than to another target. An antibody of the invention is preferably capable of binding to its target with an affinity that is at least two-fold, 10-fold, 50-fold, 100-fold or greater than its affinity for binding to another non-target molecule.

An antibody of the invention typically binds to the same epitope as the antibody having the heavy and light chain variable region sequences of SEQ ID NOs 1 and 2. In one embodiment an antibody of the invention binds to the epitope GNKLQVLGKDLLLPQ (SEQ ID NO: 30) of Lrg1 or an epitope comprising GNKLQVLGKDLLLPQ (SEQ ID NO: 30) of Lrg1. As used herein, the term "epitope" generally refers to the site on a target antigen which is recognised by an immune receptor such as an antibody. Preferably it is a short peptide derived from or as part of a protein. Epitopes can be identified from knowledge of the amino acid and corresponding DNA sequences of the peptide, as well as from the nature of particular amino acids (e.g., size, charge, etc.) and the codon dictionary, without undue experimentation. See, e.g., Ivan Roitt, Essential Immunology, 1988; Janis Kuby, Immunology, 1992 e.g., pp. 79-81.

The location of an epitope may be identified by routine methods. For example, the general location of an epitope may be determined by assessing the ability of an antibody to bind to different fragments or variant Lrg1 polypeptides. The specific amino acids within Lrg1 that make contact with an antibody may also be determined using routine methods, such as that described in the Examples. For example, the antibody and target molecule may be combined and the antibody/target complex may be crystallised. The crystal structure of the complex may be determined and used to identify specific sites of interaction between the antibody and its target. An epitope can be continuous sequence of amino acids or a discontinuous sequence of amino acids.

An antibody of the invention may bind to the same epitope or region as another antibody of the invention. For example, where an antibody of the invention is known, other antibodies of the invention may be identified by comparing their binding to Lrg1 with that of the known antibody.

An antibody of the invention may be an antibody that binds to the same epitope in Lrg1 as the antibodies described herein having the sequences of SEQ ID NOs 1 and 2. The antibody of the invention may comprise a heavy chain and/or a light chain.

An antibody of the invention may have the ability to cross-compete with another antibody of the invention for binding to Lrg1 as described herein. For example, an antibody of the invention may cross-compete with one or more of the antibodies described herein, for example an antibody having the sequences of SEQ ID NOs 1 and 2, for binding to Lrg1 or to a suitable fragment or variant of Lrg1 that is bound by the antibodies. Preferably, an antibody of the invention may cross-compete with antibody 15C4. Such cross-competing antibodies can be identified based on their ability to cross-compete with a known antibody of the invention in standard binding assays. For example, BIAcore analysis, ELISA assays or flow cytometry may be used to demonstrate cross-competition. Such cross-competition may suggest that the two antibodies bind to the same or similar epitopes.

An antibody of the invention may therefore be identified by a method that comprises a binding assay which assesses whether or not a test antibody is able to cross-compete with a known antibody of the invention for a binding site on the target molecule. Methods for carrying out competitive binding assays are well known in the art. For example they may involve contacting together a known antibody of the invention and a target molecule under conditions under which the antibody can bind to the target molecule. The antibody/target complex may then be contacted with a test antibody and the extent to which the test antibody is able to displace the antibody of the invention from antibody/target complexes may be assessed. An alternative method may involve contacting a test antibody with a target molecule under conditions that allow for antibody binding, then adding an antibody of the invention that is capable of binding that target molecule and assessing the extent to which the antibody of the invention is able to displace the test antibody from antibody/target complexes.

The ability of a test antibody to inhibit the binding of an antibody of the invention to the target demonstrates that the test compound can compete with an antibody of the invention for binding to the target and thus that the test antibody binds to the same epitope or region on the Lrg1 protein as the known antibody of the invention. A test antibody that is identified as cross-competing with a known antibody of the invention in such a method is also a potential antibody according to the present invention. The fact that the test antibody can bind Lrg1 in the same region as a known antibody of the invention and cross-compete with the known antibody of the invention suggests that the test antibody may act as a ligand at the same binding site as the known antibody and that the test antibody may therefore mimic the action of the known antibody.

The known antibody of the invention may be an antibody as described herein, such as one of the Lrg1 antibodies as described herein or any variant or fragment thereof as described herein that retains the ability to bind to Lrg1. An antibody of the invention may bind to the same epitope as one or more of the antibodies as described herein or any variant or fragment thereof as described herein that retains the ability to bind to Lrg1.

Specific binding may be assessed with reference to binding of the antibody to a molecule that is not the target. This comparison may be made by comparing the ability of an antibody to bind to the target and to another molecule. This comparison may be made as described above in an assessment of Kd or Ki. The other molecule used in such a comparison may be any molecule that is not the target molecule. Preferably the other molecule is not identical to the target molecule. Preferably the target molecule is not a fragment of the target molecule.

The term "antibody" as referred to herein includes whole antibodies and any antigen binding fragment (i.e., "antigen-binding portion") or single chains thereof. An antibody refers to a glycoprotein comprising at least two heavy (H) chains and two light (kappa)(L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody. In one embodiment, an antibody of the invention is a monoclonal antibody. Polyclonal antibodies are antibodies that are derived from different B cell lines. A polyclonal antibody may comprise a mixture of different immunoglobulin molecules that are directed against a specific antigen. The polyclonal antibody may comprise a mixture of different immunoglobulin molecules that bind to one or more different epitopes within an antigen molecule. Polyclonal antibodies may be produced by routine methods such as immunisation with the antigen of interest. For example a mouse capable of expressing human antibody sequences may be immunised with human Lrg1. Blood may be subsequently removed and the Ig fraction purified.

Monoclonal antibodies are immunoglobulin molecules that are identical to each other and have a single binding specificity and affinity for a particular epitope. Monoclonal antibodies (mAbs) of the present invention can be produced by a variety of techniques, including conventional monoclonal antibody methodology, for example those disclosed in "Monoclonal Antibodies; A manual of techniques", H Zola (CRC Press, 1988) and in "Monoclonal Hybridoma Antibodies: Techniques and Application", SGR Hurrell (CRC Press, 1982).

The term "antigen-binding portion" of an antibody refers to one or more fragments of an antibody that retain the ability to specifically bind to an antigen, such as Lrg1. It has been shown that the antigen-binding function of an antibody can be performed by fragments of a full-length antibody. Examples of binding fragments encompassed within the term "antigen-binding portion" of an antibody include a Fab fragment, a F(ab')2 fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

The antibodies or antibody fragments of the invention preferably comprise an Fc region which is an IgG1, IgG2, IgG3 or IgG4 region. The antibodies or antibody fragments of the invention preferably comprise an Fc region which is an IgG1 region. The antibodies or antibody fragments of the invention preferably comprise an Fc region which is an IgG2 region. The antibodies or antibody fragments of the invention preferably comprise an Fc region which is an IgG3 region. The antibodies or antibody fragments of the invention preferably comprise an Fc region which is an IgG4 region.

Antibodies of the invention can be tested for binding to the target protein by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example by flow cytometry.

The specificity of an antibody of the invention for target protein may be further studied by determining whether or not the antibody binds to other proteins. For example, where it is desired to produce an antibody that specifically binds Lrg1 or a particular part, e.g. epitope, of Lrg1, the specificity of the antibody may be assessed by determining whether or not the antibody also binds to other molecules or modified forms of Lrg1 that lack the part of interest.

Once a suitable antibody has been identified and selected, the amino acid sequence of the antibody may be identified by methods known in the art. The genes encoding the antibody can be cloned using degenerate primers. The antibody may be recombinantly produced by routine methods.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

The present inventors have identified antibodies as described in the examples. The present invention encompasses these antibodies and variants and fragments thereof which retain one or more activities of these antibodies. The activities of these antibodies include the ability to bind to Lrg1.

A suitable fragment or variant of this antibody will retain the ability to bind to Lrg1. It will preferably retain the ability to specifically bind to Lrg1. It will preferably retain the ability to specifically bind to the same epitope or region of the Lrg1 molecule as the antibody, for example an antibody having the sequence of SEQ ID NOs: 1 and 2, from which it is derived.

Polypeptide or antibody "fragments" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody of the invention may be, or may comprise, a fragment of the antibodies or a variant thereof. The antibody of the invention may be or may comprise an antigen binding portion of these antibodies or a variant thereof as discussed further above. For example, the antibody of the invention may be a Fab fragment of one of these antibodies or a variant thereof or may be a single chain antibody derived from one of these antibodies or a variant thereof.

The amino acid sequences of the variable regions of the heavy and light chain chains of a particular antibody of the invention are given in SEQ ID NOs: 1 and 2. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 1 and 15. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 1 and 17. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 1 and 19. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 5 and 2. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 5 and 15. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 5 and 17. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 5 and 19. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 7 and 2. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 7 and 15. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 7 and 17. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 7 and 19. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 9 and 2. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 9 and 15. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 9 and 17. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 9 and 19. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 11 and 2. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 11 and 15. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 11 and 17. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 11 and 19. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 13 and 2. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 13 and 15. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 13 and 17. The CDRs for the VH chain are shown in SEQ ID NOs: 21, 22 and 23. The CDRs for the VL chain are shown in SEQ ID NOs: 24, 25 and 26.

The amino acid sequences of the variable regions of the heavy and light chain chains of another antibody of the invention are given in SEQ ID NOs: 13 and 19. The CDRs for the VH chain are shown in SEQ ID NOs: 21, 22 and 23. The CDRs for the VL chain are shown in SEQ ID NOs: 24, 25 and 26.

An antibody of the invention may comprise the VH amino acid sequence of SEQ ID NOs: 1, 5, 7, 9, 11 or 13, or a fragment or variant of any thereof. An antibody of the invention may comprise the VL amino acid sequence of SEQ ID NOs: 2, 15, 17 or 19 or a fragment or variant of any thereof.

An antibody of the invention may comprise both (a) the VH amino acid sequence of SEQ ID NO: 1, or a fragment or variant thereof and (b) the VL amino acid sequence of SEQ ID NO: 2, or a fragment or variant thereof. Alternatively an antibody of the invention may comprise both (a) the VH amino acid sequence of SEQ ID NO: 1, or a fragment or variant thereof and (b) the VL amino acid sequence of SEQ ID NO: 15, or a fragment or variant thereof.

Alternatively an antibody of the invention may comprise both (a) the VH amino acid sequence of SEQ ID NO: 1, or a fragment or variant thereof and (b) the VL amino acid sequence of SEQ ID NO: 17, or a fragment or variant thereof.

Alternatively an antibody of the invention may comprise both (a) the VH amino acid sequence of SEQ ID NO: 1, or a fragment or variant thereof and (b) the VL amino acid sequence of SEQ ID NO: 19, or a fragment or variant thereof.

Alternatively an antibody of the invention may comprise both (a) the VH amino acid sequence of SEQ ID NO: 5, or a fragment or variant thereof and (b) the VL amino acid sequence of SEQ ID NO: 2, or a fragment or variant thereof.

Alternatively an antibody of the invention may comprise both (a) the VH amino acid sequence of SEQ ID NO: 5, or a fragment or variant thereof and (b) the VL amino acid sequence of SEQ ID NO: 15, or a fragment or variant thereof.

Alternatively an antibody of the invention may comprise both (a) the VH amino acid sequence of SEQ ID NO: 5, or a fragment or variant thereof and (b) the VL amino acid sequence of SEQ ID NO: 17, or a fragment or variant thereof.

Alternatively an antibody of the invention may comprise both (a) the VH amino acid sequence of SEQ ID NO: 5, or a fragment or variant thereof and (b) the VL amino acid sequence of SEQ ID NO: 19, or a fragment or variant thereof.

Alternatively an antibody of the invention may comprise both (a) the VH amino acid sequence of SEQ ID NO: 7, or a fragment or variant thereof and (b) the VL amino acid sequence of SEQ ID NO: 2, or a fragment or variant thereof.

Alternatively an antibody of the invention may comprise both (a) the VH amino acid sequence of SEQ ID NO: 7, or a fragment or variant thereof and (b) the VL amino acid sequence of SEQ ID NO: 15, or a fragment or variant thereof.

Alternatively an antibody of the invention may comprise both (a) the VH amino acid sequence of SEQ ID NO: 7, or a fragment or variant thereof and (b) the VL amino acid sequence of SEQ ID NO: 17, or a fragment or variant thereof.

Alternatively an antibody of the invention may comprise both (a) the VH amino acid sequence of SEQ ID NO: 7, or a fragment or variant thereof and (b) the VL amino acid sequence of SEQ ID NO: 19, or a fragment or variant thereof.

Alternatively an antibody of the invention may comprise both (a) the VH amino acid sequence of SEQ ID NO: 9, or a fragment or variant thereof and (b) the VL amino acid sequence of SEQ ID NO: 2, or a fragment or variant thereof.

Alternatively an antibody of the invention may comprise both (a) the VH amino acid sequence of SEQ ID NO: 9, or a fragment or variant thereof and (b) the VL amino acid sequence of SEQ ID NO: 15, or a fragment or variant thereof.

Alternatively an antibody of the invention may comprise both (a) the VH amino acid sequence of SEQ ID NO: 9, or a fragment or variant thereof and (b) the VL amino acid sequence of SEQ ID NO: 17, or a fragment or variant thereof.

Alternatively an antibody of the invention may comprise both (a) the VH amino acid sequence of SEQ ID NO: 9, or a fragment or variant thereof and (b) the VL amino acid sequence of SEQ ID NO: 19, or a fragment or variant thereof.

Alternatively an antibody of the invention may comprise both (a) the VH amino acid sequence of SEQ ID NO: 11, or a fragment or variant thereof and (b) the VL amino acid sequence of SEQ ID NO: 2, or a fragment or variant thereof.

Alternatively an antibody of the invention may comprise both (a) the VH amino acid sequence of SEQ ID NO: 11, or a fragment or variant thereof and (b) the VL amino acid sequence of SEQ ID NO: 15, or a fragment or variant thereof.

Alternatively an antibody of the invention may comprise both (a) the VH amino acid sequence of SEQ ID NO: 11, or a fragment or variant thereof and (b) the VL amino acid sequence of SEQ ID NO: 17, or a fragment or variant thereof.

Alternatively an antibody of the invention may comprise both (a) the VH amino acid sequence of SEQ ID NO: 11, or a fragment or variant thereof and (b) the VL amino acid sequence of SEQ ID NO: 19, or a fragment or variant thereof.

Alternatively an antibody of the invention may comprise both (a) the VH amino acid sequence of SEQ ID NO: 13, or a fragment or variant thereof and (b) the VL amino acid sequence of SEQ ID NO: 2, or a fragment or variant thereof.

Alternatively an antibody of the invention may comprise both (a) the VH amino acid sequence of SEQ ID NO: 13, or a fragment or variant thereof and (b) the VL amino acid sequence of SEQ ID NO: 15, or a fragment or variant thereof.

Alternatively an antibody of the invention may comprise both (a) the VH amino acid sequence of SEQ ID NO: 13, or a fragment or variant thereof and (b) the VL amino acid sequence of SEQ ID NO: 17, or a fragment or variant thereof.

Alternatively an antibody of the invention may comprise both (a) the VH amino acid sequence of SEQ ID NO: 13, or a fragment or variant thereof and (b) the VL amino acid sequence of SEQ ID NO: 19, or a fragment or variant thereof.

An antibody of the invention may comprise a fragment of one of the VL or VH amino acid sequences shown above.

For example, an antibody of the invention may comprise a fragment of at least 7, at least 8, at least 9, at least 10, at least 12, at least 15, at least 18, at least 20 or at least 25 consecutive amino acids from said VL or VH amino acid sequence. Such a fragment will preferably retain one or more of the functions discussed above, such as the ability to bind to Lrg1.

An antibody of the invention may comprise one, two, three, four, five or six CDR sequences from any one of the specific antibodies identified herein.

In one embodiment, an antibody of the invention is one that specifically binds to Lrg1, and comprises the CDRs of SEQ ID NOs: 1, 5, 7, 9, 11 or 13 and/or the CDRs of SEQ ID NOs: 2, 15, 17 or 19.

An antibody of the invention may comprise one or more of the CDR sequences of any one of the specific antibodies as described above. An antibody of the invention may comprise one or more heavy chain CDR sequences and alternatively or additionally one or more light chain CDR sequences of said specific antibody. An antibody of the invention may comprise one, two or all three of the heavy chain CDR sequences of a specific antibody as described above and alternatively or additionally one, two or all three of the light chain CDR sequences of said specific antibody. An antibody of the invention may comprises all six CDR sequences of a specific antibody as described above. By way of example, an antibody of the invention may comprise one or more of SEQ ID NOs: 21, 22, 23, 24, 25 and 26. An antibody of the invention may comprise one, two or all three of SEQ ID NOs: 21, 22 and 23 and/or one, two or all three of SEQ ID NOs: 24, 25 and 26. An antibody of the invention may comprise all six of SEQ ID NOs: 21, 22, 23, 24, 25 and 26.

An antibody of the invention may alternatively comprise a variant of one of these heavy or light chain variable regions or CDR sequences. For example, a variant may be a substitution, deletion or addition variant of any of the above amino acid sequences.

A variant antibody may comprise 1, 2, 3, 4, 5, up to 10, up to 20, up to 30 or more amino acid substitutions and/or deletions from the specific sequences and fragments discussed above, whilst maintaining the activity of the antibodies described herein. "Deletion" variants may comprise the deletion of, for example, 1, 2, 3, 4 or 5 individual amino acids or of one or more small groups of amino acids such as 2, 3, 4 or 5 amino acids. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

Preferred "derivatives" or "variants" include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably variant antibodies according to the invention have an amino acid sequence which has more than 60%, or more than 70%, e.g. 75 or 80%, preferably more than 85%, e.g. more than 90, 95%, 96%, 97%, 98% or 99% amino acid identity to the VL and/or VH domain, or a fragment thereof, of an antibody disclosed herein. This level of amino acid identity may be seen across the full length of the relevant SEQ ID NO sequence or over a part of the sequence, such as across 20, 30, 50, 75, 100, 150, 200 or more amino acids, depending on the size of the full length polypeptide.

Preferably the variant antibodies comprise one or more of the CDR sequences as described herein.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: G, P, S, N, D, Q, E, K, R. Sequence identity at a particular residue is intended to include identical residues which have simply been derivatized.

The present invention thus provides antibodies having specific VH and VL amino acid sequences and variants and fragments thereof which maintain the function or activity of these VH and VL domains.

Accordingly, an antibody of the invention may comprise:

(a) a heavy chain variable region amino acid sequence of SEQ ID NO: 1, 5, 7, 9, 11 or 13;

(b) a fragment of at least 7 amino acids of (a), wherein the antibody or fragment retains the ability to specifically bind to Lrg1; or (c) a variant of (a) having at least 70% amino acid sequence identity to a sequence of (a), wherein the antibody or fragment retains the ability to specifically bind to Lrg1.

An antibody of the invention may comprise:

(a) a light chain variable region amino acid sequence of SEQ ID NO: 2, 15, 17 or 19;

(b) a fragment of at least 7 amino acids of (a), wherein the antibody or fragment retains the ability to specifically bind to Lrg1; or (c) a variant of (a) having at least 70% identity amino acid identity to a sequence of (a), wherein the antibody or fragment retains the ability to specifically bind to Lrg1.

As explained above, an antibody of the invention may bind to the same epitope or region as another antibody of the invention. Thus it will be seen that such an antibody may bind to the same epitope or region of Lrg1 as any of the specific antibodies, fragments and variants described herein.

The antibody of the invention can be used in the treatment of cancer. It is preferred that a high proportion of the antibody or fragment of the invention will be retained within a tumour microenvironment in vivo for an extended period of time following local administration of said antibody or fragment to a tumour site. That is, it is preferred that the antibody or fragment exhibit reduced leakage from the tumour site into vascular or lymphatic circulation. Preferably at least 30% of an antibody dose administered to a tumour site is retained in the tumour site at four hours after administration, more preferably at least 40% of the dose is retained at four hours after administration and most preferably at least 50% of the dose is retained at four hours after administration. Antibody retention in a tumour microenvironment can be studied by injecting the antibody into tumours in murine models and measuring the serum levels of the antibody over time after administration. Alternatively the distribution of the antibody can be measured using radiolabeled antibodies injected into tumours in murine models.

The pH in a tumour microenvironment in vivo is significantly more acidic than that of healthy tissues. Ranges for tumours are reported as around pH 6.5 to 7.2 or 6.6 to 7.0, as compared to 7.2 to 7.4 for healthy tissues. This acidity is primarily due to anaerobic glycolysis in tumour regions subjected to short-term or long-term hypoxia as a result of poorly organized vasculature with diminished chaotic blood flow, and aerobic glycolysis (the Warburg effect), a common cancer phenotypic property in which the glycolytic metabolic pathways are used even in the presence of oxygen. Given this acidity, it is preferred that the antibody of the invention has a high isoelectric point because this will lead to improved retention in the tumour microenvironment relative to a similar antibody with a lower isoelectric point.

Isoelectric point of an antibody may be determined by any suitable method. It may be determined in vitro, for example by electrophoretic methods. Alternatively, isoelectric point may be calculated from basic principles. In this case the resulting isoelectric point is typically referred to as a theoretical isoelectric point. Numerous software programs exist for the in silico calculation of theoretical isoelectric point, for example GP-MAW (version 9.2, from Lighthouse Data). An antibody of the invention preferably has a theoretical isoelectric point (pI) of 9.0 or above, preferably 9.1 or above, more preferably 9.2 or above, most preferably 9.25 or above.

The invention also relates to polynucleotides that encode antibodies of the invention. Thus, a polynucleotide of the invention may encode any antibody or fragment as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises a sequence which encodes a VH or VL amino acid sequence as described above. The polynucleotide may encode the VH or VL sequence of a specific antibody as disclosed herein. For example, a polynucleotide of the invention may encode a polypeptide comprising the sequence of SEQ ID NO: 1, 5, 7, 9, 11 or 13; or may encode a polypeptide comprising the sequence of SEQ ID NO: 2, 15, 17 or 19; or a variant or fragment of any thereof as described above.

Such a polynucleotide may consist of or comprise a nucleic acid sequence of any one of SEQ ID NOs: 3, 6, 8, 10, 12 or 14; or SEQ ID NOs: 4, 16, 18 or 20.

A polynucleotide of the invention may comprise or consist of both the sequences of SEQ ID NOs: 3 and 4; SEQ ID NOs: 3 and 16; SEQ ID NOs: 3 and 18; SEQ ID NOs: 3 and 20; SEQ ID NOs: 6 and 4; SEQ ID NOs: 6 and 16; SEQ ID NOs: 6 and 18; SEQ ID NOs: 6 and 20; SEQ ID NOs: 8 and 4; SEQ ID NOs: 8 and 16; SEQ ID NOs: 8 and 18; SEQ ID NOs: 8 and 20; SEQ ID NOs: 10 and 4; SEQ ID NOs: 10 and 16; SEQ ID NOs: 10 and 18; SEQ ID NOs: 10 and 20; SEQ ID NOs: 12 and 4; SEQ ID NOs: 12 and 16; SEQ ID NOs: 12 and 18; SEQ ID NOs: 12 and 20; SEQ ID NOs: 14 and 4; SEQ ID NOs: 14 and 16; SEQ ID NOs: 14 and 18; or SEQ ID NOs: 14 and 20.

A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of nucleic acid sequences disclosed herein, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more amino acids may be removed from the 3' and/or 5' end of the polynucleotide in this way. Fragments may also be generated by one or more internal deletions. Such fragments may be derived from a sequence as described herein or may be derived from a variant polynucleotide as described herein. Preferably such fragments are between 30 and 300 residues in length, e.g. 30 to 300, 30 to 200, 30 to 100, 100 to 200 or 200 to 300 residues. Alternatively, fragments of the invention may be longer sequences, for example comprising at least 50%, at least 60%, at least 70%, at least 80% or at least 90% of a full length polynucleotide of the invention.

An antibody of the invention may thus be produced from or delivered in the form of a polynucleotide which encodes, and is capable of expressing, it. Where the antibody comprises two or more chains, a polynucleotide of the invention may encode one or more antibody chains. For example, a polynucleotide of the invention may encode an antibody light chain, an antibody heavy chain or both. Two polynucleotides may be provided, one of which encodes an antibody light chain and the other of which encodes the corresponding antibody heavy chain. Such a polynucleotide or pair of polynucleotides may be expressed together such that an antibody of the invention is generated.

Polynucleotides of the invention can be synthesised according to methods well known in the art, as described by way of example in Sambrook et al (1989, Molecular Cloning—a laboratory manual; Cold Spring Harbor Press).

The nucleic acid molecules of the present invention may be provided in the form of an expression cassette which includes control sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express an antibody of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for an antibody of the invention include mammalian HEK293T, CHO, HeLa, NS0 and COS cells. Preferably the cell line selected will be one which is not only stable, but also allows for mature glycosylation.

Such cell lines of the invention may be cultured using routine methods to produce an antibody of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

In another aspect, the present invention provides compositions and formulations comprising molecules of the invention, such as the antibodies, polynucleotides, vectors and cells described herein. For example, the invention provides a pharmaceutical composition comprising one or more molecules of the invention, such as one or more antibodies of the invention, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intraocular, intramuscular or subcutaneous administration (e.g., by injection or infusion).

Direct retinal, subretinal or intravitreal delivery of the antibody of the invention, typically by injection, may be preferred. Delivery to the retinal, subretinal space or intravitreal space may be preferred.

Depending on the route of administration, the antibody may be coated in a material to protect the antibody from the action of acids and other natural conditions that may inactivate or denature the antibody.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A pharmaceutical composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Pharmaceutical compositions of the invention may comprise additional active ingredients as well as an antibody of the invention. As mentioned above, compositions of the invention may comprise one or more antibodies of the invention. They may also comprise additional therapeutic or prophylactic agents.

Also within the scope of the present invention are kits comprising antibodies or other compositions of the invention and instructions for use. The kit may further contain one ore more additional reagents, such as an additional therapeutic or prophylactic agent as discussed above.

The antibodies in accordance with the present invention may be used in therapy. In therapeutic applications, antibodies or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". Effective amounts for a given purpose will depend on the severity of the disease or injury as well as the weight and general state of the subject. As used herein, the term "subject" includes any human.

Any condition in which Lrg-1-mediated vasculoproliferation occurs may, in principle, be treated, prevented or ameliorated according to the present invention. "Vasculoproliferation", "vasculoproliferative", "vasculoproliferative conditions" and similar terms as used herein encompass any and all pathologies related to the aberrant or unwanted development of blood vessels or vascular tissue or cells. For example, both pathogenic angiogenesis (the formation of new blood vessels, for example via new capillary growth from existing blood vessels) and vascular malformation (e.g. telangiectasia, the formation of dilated, tortuous and incompetent vessels, microaneurysms) can be prevented or reduced, as can neovascularisation and vascular endothelial cell proliferation. Also, as is known in the art, neoplastic growth requires the formation of new blood vessels to provide a blood supply to the growing tumour. Tumours in which Lrg1-mediated vasculoproliferation occurs are therefore also conditions which may be treated, prevented or ameliorated according to the present invention.

Preferably, there is no, or minimal effect on normal, e.g. developmental vascularisation, especially developmental vascularisation in the retina. Treatment of ocular vasculoproliferative conditions is a preferred embodiment. Among conditions that can be treated are: diabetic retinopathy, retinal vein occlusion, retinopathy of prematurity, macular telangiectasia, age-related macular degeneration or choroidal neovascularisation. Accordingly, in one embodiment, the invention provides an antibody of the invention, or fragment thereof, for use in the treatment of vasculoproliferative conditions. The invention also provides a method of treating a vasculoproliferative condition comprising to an individual an antibody of the invention, or a fragment thereof. The invention also provides an antibody of the invention, or fragment thereof, for use in the manufacture of a medicament for the treatment of a vasculoproliferative condition.

Treatment of tumours, typically solid tumours, can also be effected. Accordingly, in one embodiment, the invention provides an antibody of the invention, or fragment thereof, for use in the treatment of cancer. The invention also provides a method of treating cancer comprising administering to an individual an antibody of the invention, or a fragment thereof. The invention also provides an antibody of the invention, or fragment thereof, for use in the manufacture of a medicament for the treatment of cancer.

The cancer may be a cancer that exhibits solid tumours. The cancer may be brain, breast, kidney, colorectal, lung, prostate, head and neck, stomach, pancreatic, skin, cervical, bone, ovarian, testicular or liver cancer.

In particular embodiments, the antibody of the invention may be linked (directly or indirectly) to another moiety. The other moiety may be a therapeutic agent such as a cytotoxic moiety or a drug. The other moiety may be a detectable label. The other moiety may be a binding moiety, such as a tumour-specific antibody or a polypeptide binding domain specific for a therapeutic target, preferably a therapeutic target associated with cancer, which target is not human Lrg1. The resulting bispecific molecule may be for use in the treatment of cancer.

Thus, as an example, the antibody of the invention, or an antigen binding fragment thereof, may be linked (directly or indirectly) to a polypeptide binding domain specific for human VEGF.

The antibody of the invention may be a bispecific antibody. The antibody of the invention may be a bispecific antibody that binds human Lrg1 and human VEGF. The antibody of the invention may be a bispecific antibody that binds human Lrg1 and human PDGF. The antibody of the invention may be a bispecific antibody that binds human Lrg1 and human Anti-Complement Factor D Fab. The antibody of the invention may be a bispecific antibody that binds human Lrg1 and human PDGFR. The antibody of the invention may be a bispecific antibody that binds human Lrg1 and human Tie2 tyrosine kinase inhibitor.

The therapeutic agent or a detectable label may be directly attached, for example by chemical conjugation, to an antibody of the invention. Methods of conjugating agents or labels to an antibody are known in the art. For example, carbodiimide conjugation (Bauminger & Wilchek (1980) Methods Enzymol. 70, 151-159) may be used to conjugate a variety of agents, including doxorubicin, to antibodies or peptides. The water-soluble carbodiimide, 1-ethyl-3-(3-dimethylaminopropyl) carbodiimide (EDC) is particularly useful for conjugating a functional moiety to a binding moiety.

Other methods for conjugating a moiety to antibodies can also be used. For example, sodium periodate oxidation followed by reductive alkylation of appropriate reactants can be used, as can glutaraldehyde cross-linking. However, it is recognised that, regardless of which method of producing a conjugate of the invention is selected, a determination must be made that the antibody maintains its targeting ability and that the functional moiety maintains its relevant function.

A cytotoxic moiety may be directly and/or indirectly cytotoxic. By "directly cytotoxic" it is meant that the moiety is one which on its own is cytotoxic. By "indirectly cytotoxic" it is meant that the moiety is one which, although is not itself cytotoxic, can induce cytotoxicity, for example by its action on a further molecule or by further action on it. The cytotoxic moiety may be cytotoxic only when intracellular and is preferably not cytotoxic when extracellular.

Preferably, the invention provides an antibody or antigen-binding fragment, or a variant, fusion or derivative thereof, wherein the cytotoxic moiety is a directly cytotoxic chemotherapeutic agent. Optionally, the cytotoxic moiety is a directly cytotoxic polypeptide. Cytotoxic chemotherapeutic agents are well known in the art.

The cytotoxic agent may also be administered separately to the antibody of the invention.

Cytotoxic chemotherapeutic agents, such as anticancer agents, include: alkylating agents including nitrogen mustards such as mechlorethamine (HN2), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; and hormone agonists/antagonists such as flutamide and tamoxifen.

In one embodiment of the invention, the cytotoxic moiety is a cytotoxic peptide or polypeptide moiety which leads to cell death. Cytotoxic peptide and polypeptide moieties are well known in the art and include, for example, ricin, abrin, *Pseudomonas* exotoxin, tissue factor and the like. Methods for linking them to targeting moieties such as antibodies are also known in the art. Other ribosome inactivating proteins are described as cytotoxic agents in WO 96/06641. *Pseudomonas* exotoxin may also be used as the cytotoxic polypeptide. Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the agents of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the antibody, antigen-binding fragment, variant, fusion or derivative thereof in known ways. For example, EDTA or another chelating agent may be attached to the binding moiety and used to attach 111In or 90Y. Tyrosine residues may be directly labelled with 125I or 131I.

The cytotoxic moiety may be a suitable indirectly-cytotoxic polypeptide. In a particularly preferred embodiment, the indirectly cytotoxic polypeptide is a polypeptide which has enzymatic activity and can convert a non-toxic and/or relatively non-toxic prodrug into a cytotoxic drug. With antibodies, this type of system is often referred to as ADEPT (Antibody-Directed Enzyme Prodrug Therapy). The system requires that the antibody locates the enzymatic portion to the desired site in the body of the patient and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues. In a preferred embodiment, the cytotoxic moiety is capable of converting a non-cytotoxic prodrug into a cytotoxic drug.

The enzyme and prodrug of the system using a targeted enzyme as described herein may be any of those previously proposed. The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include those listed in Table 2, below.

TABLE 2

| Enzyme | Prodrug |
| --- | --- |
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate Mitomycin phosphate |
| Beta-glucuronidase | p-Hydroxyaniline mustard-glucuronide Epirubicin-glucuronide |
| Penicillin-V-amidase | Adriamycin-N phenoxyacetyl |
| Penicillin-G-amidase | N-(4'-hydroxyphenyl acetyl) palytoxin Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-gluco-pyranosiduronic acid |
| Nitroreductase | 5-(Azaridin-1-yl-)-2,4-dinitrobenzamide |
| Cytosine deaminase | 5-Fluorocytosine |
| Carboxypeptidase A | Methotrexate-alanine |

Suitable enzymes for forming part of an enzymatic portion include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as e.g. thrombolysin (for thrombin prodrugs); hydrolases, such as phosphatases (e.g. alkaline phosphatase) or sulphatases (e.g. aryl sulphatases) (for phosphylated or sulphated prodrugs); amidases, such as penicillin amidases and arylacyl amidase; lactamases, such as β-lactamases; glycosidases, such as β-glucuronidase (for β-glucuronomide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

Preferably, the prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the agent of the invention but it is necessary only for it to be active when (a) it is in combination with the rest of the agent of the invention and (b) the agent of the invention is attached to, adjacent to or internalised in target cells.

When each moiety is a polypeptide, the two portions may be linked together by any of the conventional ways of cross-linking polypeptides. For example, the antibody, antigen-binding fragment, variant, fusion or derivative thereof, may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, the antibody, antigen-binding fragment, variant, fusion or derivative thereof, may be produced as a fusion compound by recombinant DNA techniques whereby a length of DNA comprises respective regions encoding the two moieties of the agent of the invention either adjacent one another or separated by a region encoding a linker peptide which does not destroy the desired properties of the agent. Conceivably, the two portions of the agent may overlap wholly or partly.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole. Also, delivery of genes into cells can radiosensitise them, for example delivery of the p53 gene or cyclin D. The further moiety may be one which becomes cytotoxic, or releases a cytotoxic moiety, upon irradiation. For example, the boron-10 isotope, when appropriately irradiated, releases a particles which are cytotoxic. Similarly, the cytotoxic moiety may be one which is useful in photodynamic therapy such as photofrin.

The cytotoxic agent may be a cytoskeletal drug such as Paclitaxel.

The further moiety may comprise a nucleic acid molecule which is directly or indirectly cytotoxic. For example, the nucleic acid molecule may be an antisense oligonucleotide which, upon localisation at the target site is able to enter cells and lead to their death. The oligonucleotide, therefore, may be one which prevents expression of an essential gene, or one which leads to a change in gene expression which causes apoptosis. Alternatively, the cytotoxic moiety is a nucleic acid molecule encoding a directly and/or indirectly cytotoxic polypeptide. Examples of suitable oligonucleotides include those directed at bcl-2, DNA polymerase a and topoisomerase IIα. Peptide nucleic acids may be useful in place of conventional nucleic acids.

The antibody, antigen-binding fragment, variant, fusion or derivative thereof may be comprised in a delivery vehicle for delivering nucleic acid to the target. The delivery vehicle may be any suitable delivery vehicle. It may, for example, be a liposome containing nucleic acid, or it may be a virus or virus-like particle which is able to deliver nucleic acid. In these cases, the molecule to be delivered is typically present on the surface of the delivery vehicle. For example, an antibody or fragment may be present in the outer surface of a liposome and the nucleic acid to be delivered may be present in the interior of the liposome. As another example, a viral vector, such as a retroviral or adenoviral vector, is engineered so that the binding moiety is attached to or located in the surface of the viral particle thus enabling the viral particle to be targeted to the desired site. Immunoliposomes (antibody-directed liposomes) may be used. In one method for the preparation of immunoliposomes, MPB-PE (N-[4-(p-maleimidophenyl)-butyryl]-phosphatidylethanolamine) is synthesised according to the method of Martin & Papahadjopoulos (1982) J. Biol. Chem. 257, 286-288. MPB-PE is incorporated into the liposomal bilayers to allow a covalent coupling of the antibody, or fragment thereof, to the liposomal surface. The liposome is conveniently loaded with the DNA or other genetic construct for delivery to the target cells, for example, by forming the said liposomes in a solution of the DNA or other genetic construct, followed by sequential extrusion through polycarbonate membrane filters with 0.6 µm and 0.2 µm pore size under nitrogen pressures up to 0.8 MPa. After extrusion, entrapped DNA construct is separated from free DNA construct by ultracentrifugation at 80 000× g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000× g for 45 min. Immunoliposomes may be injected intraperitoneally or directly into the tumour.

The nucleic acid delivered to the target site may be any suitable DNA which leads, directly or indirectly, to cytotoxicity. For example, the nucleic acid may encode a ribozyme which is cytotoxic to the cell, or it may encode an enzyme which is able to convert a substantially non-toxic prodrug into a cytotoxic drug (this latter system is sometime called GDEPT: Gene Directed Enzyme Prodrug Therapy). Suitable ribozymes include polymerases, dephosphorylases, and restriction endonucleases. Suitable targets for ribozymes include transcription factors such as c-fos and c-myc, and bcl-2. Similar considerations concerning the choice of enzyme and prodrug apply to the GDEPT system as to the ADEPT system described above. The nucleic acid delivered to the target site may encode a directly cytotoxic polypeptide.

The therapeutic agent linked to the antibody may comprise a polypeptide or a polynucleotide encoding a polypeptide which is not either directly or indirectly cytotoxic but is of therapeutic benefit. Examples of such polypeptides include anti-proliferative or anti-inflammatory cytokines, and anti-proliferative, immunomodulatory or factors influencing blood clotting which may be of benefit in medicine, for example in the treatment of cancer. The agent may usefully be an inhibitor of angiogenesis such as the peptides angiostatin or endostatin. The agent may also usefully be an enzyme which converts a precursor polypeptide to angiostatin or endostatin. Human matrix metallo-proteases such as macrophage elastase, gelatinase and stromolysin convert plasminogen to angiostatin. Plasminogen is a precursor of angiostatin.

The antibody may be linked to a detectable label. By "detectable label" it is meant that the antibody is linked to a moiety which, when located at the target site following administration of the antibody into a patient, may be detected, typically non-invasively from outside the body and the site of the target located. Thus, the antibody may be useful in imaging and diagnosis.

Typically, the label is or comprises a radioactive atom which is useful in imaging. Suitable radioactive atoms include 99mTc and 123I for scintigraphic studies. Other labels include, for example, spin labels for magnetic resonance imaging (MRI) such as 123I again, 131I, 111In, 19F, 13C, 15N, 17O, gadolinium, manganese or iron. Clearly, the sufficient amount of the appropriate atomic isotopes must be linked to the antibody in order for the molecule to be readily detectable.

The radio- or other labels may be incorporated in known ways. For example, the antibody, or fragment thereof, may be biosynthesised or may be synthesised by chemical amino acid synthesis using suitable amino acid precursors involving, for example, fluorine-19 in place of hydrogen. Labels such as 99mTc, 123I, 186Rh, 188Rh and 111In can, for example, be attached via cysteine residues in polypeptides. Yttrium-90 can be attached via a lysine residue. Preferably, the detectable label comprises a radioactive atom, such as, for example technetium-99m or iodine-123.

Alternatively, the detectable label may be selected from the group comprising: iodine-123; iodine-131; indium-111; fluorine-19; carbon-13; nitrogen-15; oxygen-17; gadolinium; manganese; iron.

In one embodiment, an antibody of the invention is able to bind selectively to a directly or indirectly cytotoxic moiety or to a detectable label. Thus, in this embodiment, the antibody is linked to a moiety which selectively binds to a further compound or component which is cytotoxic or readily detectable.

An antibody or fragment of the present invention, or a composition comprising said antibody or fragment, may be administered via one or more routes of administration using one or more of a variety of methods known in the art. As will be appreciated by the skilled artisan, the route and/or mode of administration will vary depending upon the desired results. Preferred routes of administration for antibodies or compositions of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection. Alternatively, an antibody or composition of the invention can be administered via a non-parenteral route, such as a topical, epidermal or mucosal route of administration. Local administration is also preferred, including peritumoral, juxtatumoral, intratumoral, intralesional, perilesional, intra cavity infusion, intravesicle administration, and inhalation.

In one preferred embodiment the antibody is administered by direct retinal, subretinal or intravitreal delivery. Typically, this administration is by injection.

A suitable dosage of an antibody of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody of the invention may be, for example, in the range of from about 0.1 µg/kg to about 100 mg/kg body weight of the patient to be treated. For example, a suitable dosage may be from about 1 µg/kg to about 10 mg/kg body weight per week, from about 100 µg/kg to about 10 mg/kg body weight per week or from about 10 µg/kg to about 5 mg/kg body weight per week.

A suitable dosage may be from about 1 µg/kg to about 10 mg/kg body weight per day, from about 100 µg/kg to about 10 mg/kg body weight per day or from about 10 µg/kg to about 5 mg/kg body weight per day.

For injections into the eye, a suitable dose may be about 100 µg to 10 mg per injection, or about 1 mg to 10 mg per injection, or about 1 mg to 5 mg per injection.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Antibodies may be administered in a single dose or in multiple doses. The multiple doses may be administered via the same or different routes and to the same or different locations. Alternatively, antibodies can be administered as a sustained release formulation, in which case less frequent administration is required. Dosage and frequency may vary depending on the half-life of the antibody in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Combined administration of two or more agents may be achieved in a number of different ways. In one embodiment, the antibody and the other agent may be administered together in a single composition. In another embodiment, the antibody and the other agent may be administered in separate compositions as part of a combined therapy. For example, the antibody may be administered before, after or concurrently with the other agent. The antibody of the invention may be administered in combination with or sequentially to cytotoxic agents, anti-cancer agents, tumour targeting antibodies, target therapy, pathway inhibitors or other immunomodulatory antibodies targeting eg. PD-1, PD-L1, CD137, GITR, OX40, CTLA-4, CD27, HVEM, LtBR, LAG3, PDGF, Anti-Complement Factor D Fab, PDGFR and Tie2 tyrosine kinase inhibitor. Further the antibody of the invention may also be combined with local radiation.

The antibody of the invention can be administered in combination with an antagonist of VEGF. The antibody of the invention can be administered in combination with an anti-VEGF antibody or a soluble receptor of VEGF, such as Aflibercept (Eylea), or an anti-VEGF antibody such as Bevacizumab (Avastin) or Ranibizumab (Lucentis).

The antibody of the invention can be administered in combination with anti-cancer agents that stimulate the immune system. The antibody of the invention can be administered in combination with anti-cancer agents that stimulate the immune system such as cytokines. The antibody of the invention can be administered in combination with dendritic cells that have been stimulated to initiate a cytotoxic response against cells expressing tumour antigens. The antibody of the invention can be administered in combination with T cells, or tumour-infiltrating lymphocytes, that have been primed to attack cancerous cells. The antibody of the invention can be administered in combination with T cells that have been genetically engineered to recognise tumour antigens. The antibody of the invention can be administered in combination with autologous immune enhancement therapy.

The present inventors have found that knocking out expression of Lrg1 in solid tumours causes a decrease in the number of small vessels in the tumours. This decrease is associated with a decrease in tumour size, a decrease in the number of proliferating cells in the tumours and an increase in pericyte coverage on the remaining vessels. Taken together, the results indicate that knocking out Lrg1 expression acts to normalise tumour vasculature.

Furthermore, the present inventors have also found that Lrg1 antagonists reduce tumour growth and normalise the vasculature of the remaining tumour. These data, would suggest that antagonists of Lrg1 could be used to reduce metastatic spread. Antagonists of Lrg1 could be used to improve the delivery and efficacy of anti-cancer and cytotoxic drugs and cells to a tumour.

Lrg1 drives chaotic vasculature in tumours. Lrg1 drives chaotic VEGF angiogenesis, where vessels are non-physiological. However, Lrg1 is not upregulated in developmental angiogenesis. Any tumour with abnormal vasculature can be treated with an antagonist of Lrg1 to normalise the vasculature of the tumour, in combination with any other anti-cancer drug, examples of which are described herein. For example, an antagonist of Lrg1 can be used in combination with a VEGF antagonist to treat a tumour. Any tumour can be co-treated with an antagonist of Lrg1.

Lrg1 antagonists include antibodies that bind to Lrg1, peptides and peptidomimetics that block Lrg1 function by binding to Lrg1, small molecule inhibitors that bind to Lrg1, double-stranded RNAs that inhibit Lrg1 expression, aptamers and ribozymes that target Lrg1. Preferred antagonists include peptide fragments of Lrg1, double-stranded RNAs that inhibit Lrg1 expression, aptamers that inhibit Lrg1 expression and antibodies that bind Lrg1.

In an embodiment of the invention an antagonist of Lrg1 can be used in the prevention of cancer metastasis.

In an embodiment of the invention an antagonist of Lrg1 can be used in combination with anti-cancer agents that stimulate the immune system. The Lrg1 antagonist of the invention can be administered in combination with anti-cancer agents that stimulate the immune system such as cytokines. The Lrg1 antagonist of the invention can be administered in combination with dendritic cells that have been stimulated to initiate a cytotoxic response against cells expressing tumour antigens. The Lrg1 antagonist of the invention can be administered in combination with T cells, or tumour-infiltrating lymphocytes, that have been primed to attack cancerous cells. The Lrg1 antagonist of the invention can be administered in combination with T cells that have been genetically engineered to recognise tumour antigens. The Lrg1 antagonist of the invention can be administered in combination with autologous immune enhancement therapy.

In an embodiment of the invention an antibody of the invention as described herein Lrg1 can be used in the prevention of metastasis.

In an embodiment of the invention an antagonist of Lrg1 in combination with a VEGF inhibitor for use in the treatment of a VEGF inhibitor-resistant tumour or eye condition.

In an embodiment of the invention an antibody or fragment thereof according to the invention can be used in combination with an antiangiogenic compound.

In an embodiment of the invention an antibody or fragment thereof according to the invention can be used in combination with an anti-cancer agent.

In a further embodiment of the invention the antiangiogenic compound is an antagonist of vascular endothelial growth factor (VEGF).

In a further embodiment of the antagonist of VEGF is an anti-VEGF antibody.

In a further embodiment of the antagonist of VEGF is Aflibercept (Eylea).

In a further embodiment of the antagonist of VEGF is Bevacizumab (Avastin) or Ranibizumab (Lucentis).

The present inventors have shown that blocking Lrg1 improves the physiological status of blood vessels in a tissue, reducing the presence of chaotic vessels. Blocking Lrg1 activity would be advantageous for revascularisation in general, in conjunction with pro-angiogenic drugs. Normalisation of vasculature by Lrg1 antagonists would also allow for treatment of diseases where it would be useful to increase vascularisation. Treatment with a Lrg1 antagonist would reduce chaotic and immature vessel formation. Subsequent treatment with a pro-angiogenic agent would improve functional mature vascularisation. Such treatment would be useful for the treatment of any disease where tissues are affected by hypoxia or diseases where there are malformed blood vessels. Such diseases include, ischemia, ischemic heart disease, diabetes, ischemic stroke, vascular dementia, transient ischemic attack, mitral valve disease, chronic atrial fibrillation, cardiomyopathies, acute limb ischemia, peripheral limb ischemia, thrombosis, blood vessel occlusion, thoracic outlet syndrome, atherosclerosis, hypoglycaemia, tachycardia, hypotension, sickle cell disease, frostbite, arteriovenous malformations, blood vessel rupture and anemia.

Pro-angiogenic agents which could be used in conjunction with Lrg1 antagonists include, VEGF, bFGF (Fibroblast Growth Factor), PLGF (Placental Growth Factor) and angiopoietin 2.

The invention provides an antagonist of Lrg1 for use in a method of revascularisation of a tissue in which the vasculature is malformed. The invention provides an antagonist of Lrg1 in conjunction with a pro-angiogenic agent for use in a method of revascularisation of a tissue in which the vasculature is malformed. The invention provides a method of revascularisation of a tissue in which the vasculature is malformed comprising administering to an individual an antagonist of Lrg1. The invention provides a method of revascularisation comprising administering to an individual an antagonist of Lrg1 in conjunction with a pro-angiogenic agent. The invention provides an antagonist of Lrg1 in conjunction with a pro-angiogenic agent for use in the manufacture of a medicament for a method of revascularisation of a tissue in which the vasculature is malformed.

In an embodiment of the invention, the method of revascularisation is a disease where tissues are affected by hypoxia, as described above.

The present invention is further illustrated by the following examples which should not be construed as further limiting. The contents of all figures and all references, patents and published patent applications cited throughout this application are expressly incorporated herein by reference.

EXAMPLES 102 candidate mAbs against human Lrg1 were generated and all were subjected to the following tests: species cross-reactivity using whole serum, the Matrigel assay (using Human umbilical vein endothelial cells (HUVEC)), a HUVEC co-culture assay, affinity determination using Biacore for recombinant forms of both human and mouse Lrg1, and the mouse metatarsal angiogenesis assay. A subset of the most promising mAbs were then examined in the following tests: laser-induced choroidal neovascularisation in both mouse and rat, species cross-reactivity analysis using fractionated whole serum, affinity determination by ELISA, specificity for target by western blotting, ability to block Lrg1-mediated activation of Smad5 by TGFβ.

Example 1—Species Cross-Reactivity Using Whole Serum

Species cross-reactivity was carried out by ELISA in a protocol in which multiwall plates were coated with rhLrg1, and liver extracts from mouse, rat, rabbit, monkey, dog and cat. Plates were then probed with each mAb at 100 nM followed by an alk-phos conjugated secondary antibody and colour reaction. mAb 4H2 was observed to have cross-reactivity against both mouse and rat (though with superior reactivity against rat Lrg1), and also cat, dog, cynomolgus monkey and rabbit. None of antibodies 4H2, 3A11 or 15C4 exhibited strong cross-reactivity with rodent Lrg1.

Example 2—Affinity Measurements Using Biacore

Biacore was used to measure the binding affinity, association and dissociation constants of the antibodies to human Lrg1. Human Lrg1 was immobilized on the Biacore chip, and mAbs passed across at concentrations ranging from 20-100 nM. A cut off binding affinity value of 2 nM was used to isolate possible candidate antibodies for further investigation. Three antibodies, 15C4, 4H2 and 3A11, bound with especially high affinity.

Figure 1:
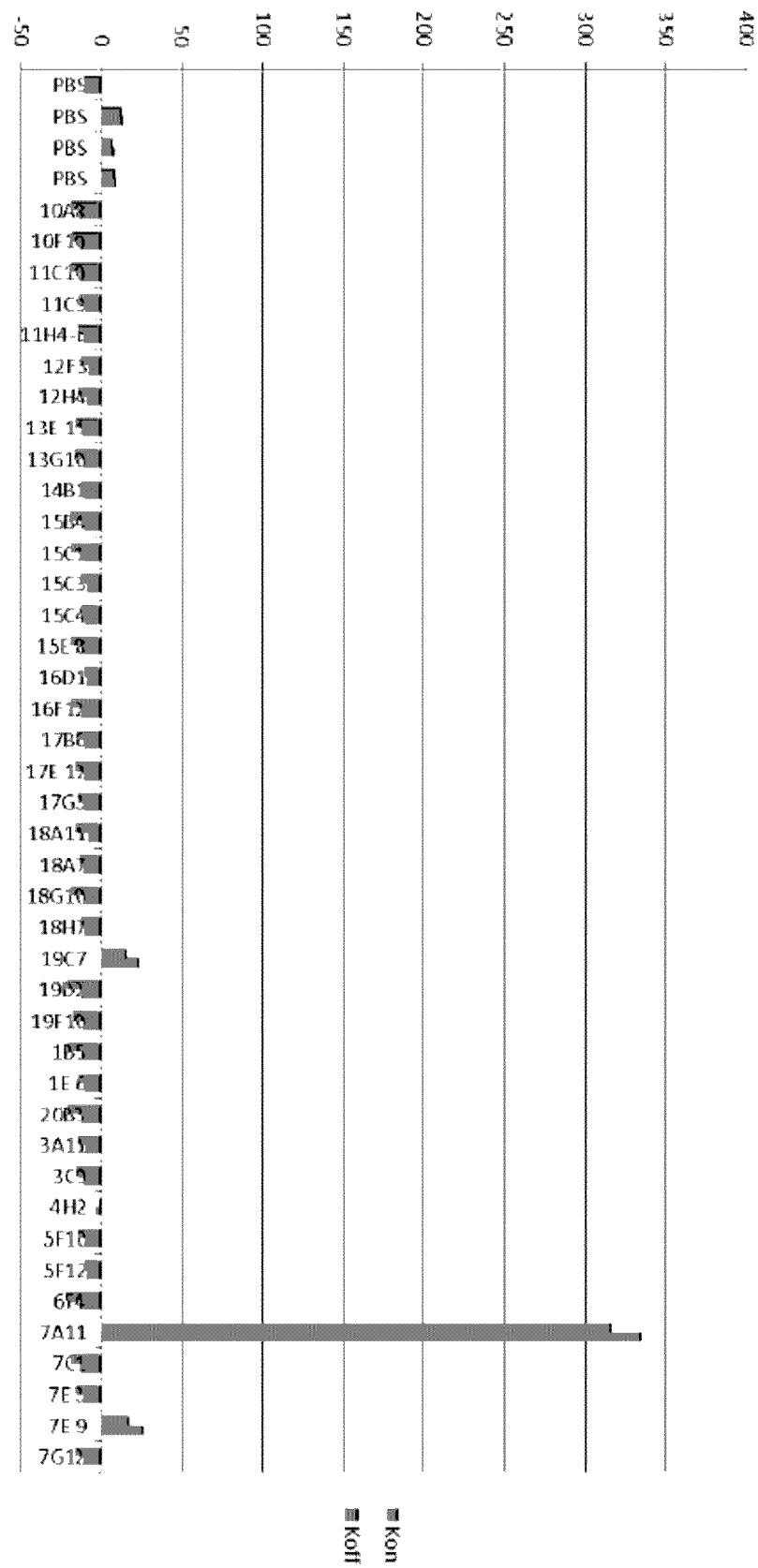
FIG. 1: Histogram of antibody binding to recombinant mouse Lrg1. The data show that cross-reactivity with mouse Lrg1 is unusual among mAbs raised against human Lrg1. In this experiment mAbs were evaluated at 100 nM and the majority failed to generate Response Units (vertical axis) above background.

Biacore was also used to examine the affinity of all mAbs for recombinant mouse Lrg1. In these experiments mouse Lrg1 was immobilized on the Biacore chip and the mAbs were passed over at 100 nM, as was done for the human Lrg1 analysis. FIG. 1 shows that only 3 mAbs elicited measurable response units when tested at that concentration.

The data show that cross-reactivity with mouse Lrg1 is unusual among the antibodies raised against human Lrg1.

Based on binding affinities and species cross-reactivity a large number of the initial 102 mAbs were eliminated at an early stage, which meant that it was possible to perform subsequent functional investigations using individual mAbs rather than pools. An iterative process of elimination led to detailed examination of four promising candidates, 3A11, 15C4, 4H2 and 5F12.

Example 3—Matrigel Assay

Figure 2:
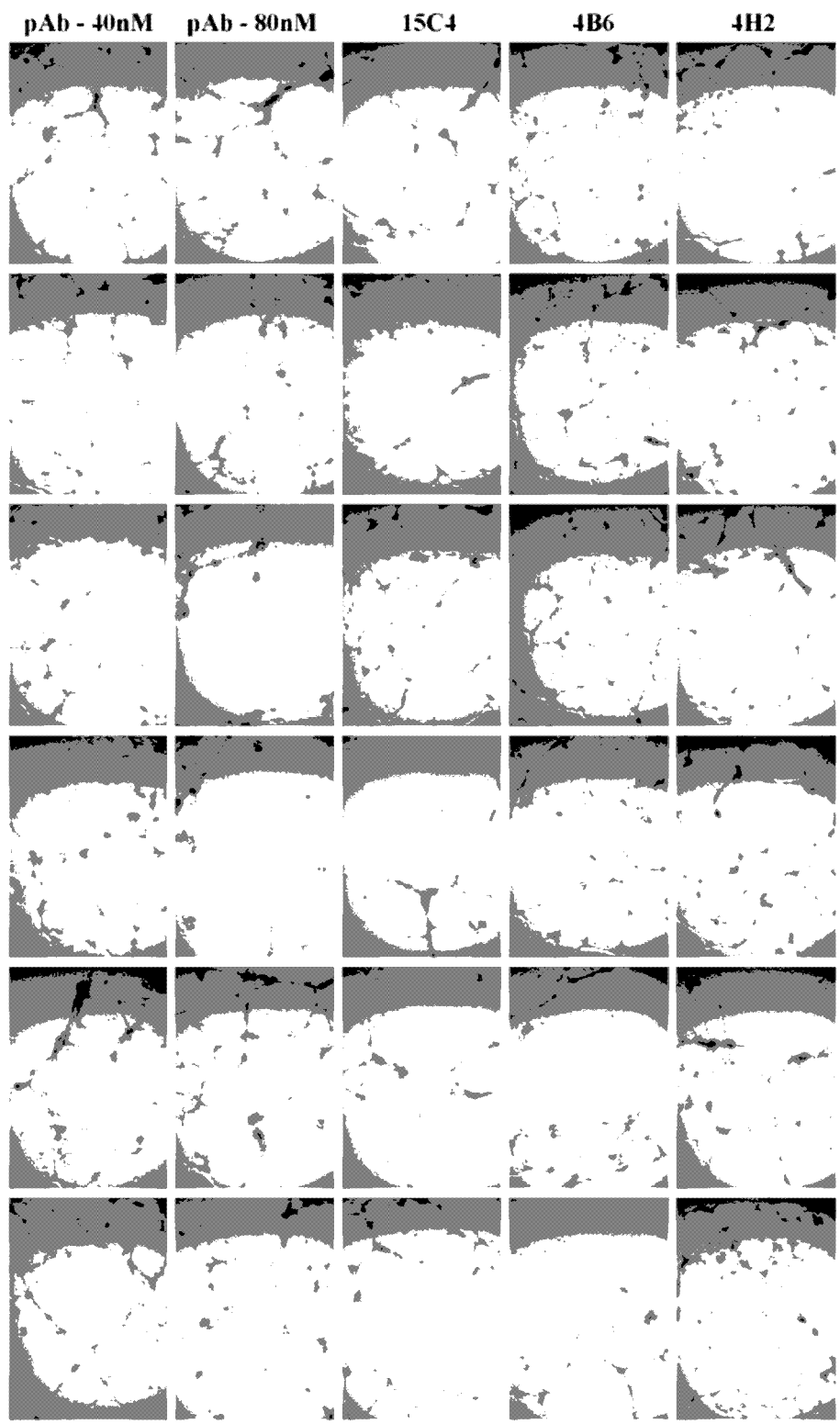
FIG. 2: Inhibition of tube formation in the Matrigel assay. HUVEC were plated on Matrigel and cultured overnight in the presence of 100 nM mAbs. The blocking rabbit polyclonal antibody (pAb) was also evaluated at 40 nM and 80 nM. 40% blocking was observed with 4H2 and 60% with 15C4.

The antibodies were tested for their ability to inhibit tube formation in a Matrigel assay. Human umbilical vein endothelial cells (HUVEC) were plated on Matrigel and cultured overnight in the presence of 100 nM mAbs. The blocking rabbit polyclonal Lrg1 antibody was also evaluated. 40% blocking of tube formation was observed with mAb 4H2 and 60% with mAb 15C4 (FIG. 2). Variability between batches of HUVEC in this assay were observed, with inhibition by 3A11 and 15C4>80% in some instances, comparable to the ~80% inhibition observed with the rabbit polyclonal antibody when used at 100 nM. Blocking with 4H2 never exceeded ~50%.

Example 4—Functional Testing in Ex Vivo Assays-Mouse Metatarsal Angiogenesis Assay In this assay the function-blocking activity of the mAbs was tested, using explanted E16.5 mouse metatarsals. Vessels grow spontaneously from the embryonic bones to form a 2D-network that can be readily quantified with regard to, for example, vessel length, calibre and branch points. In the mouse metatarsal assay mAbs were added at 100 nM to the culture medium during 12 days of culture, with replenishment of media and mAbs every two days. At the end of the experiment samples were fixed and immunostained for Platelet endothelial cell adhesion molecule (PECAM), and vascular networks were quantified using Imaris software, with normalization to a phosphate buffered saline (PBS) control.

Figure 3:
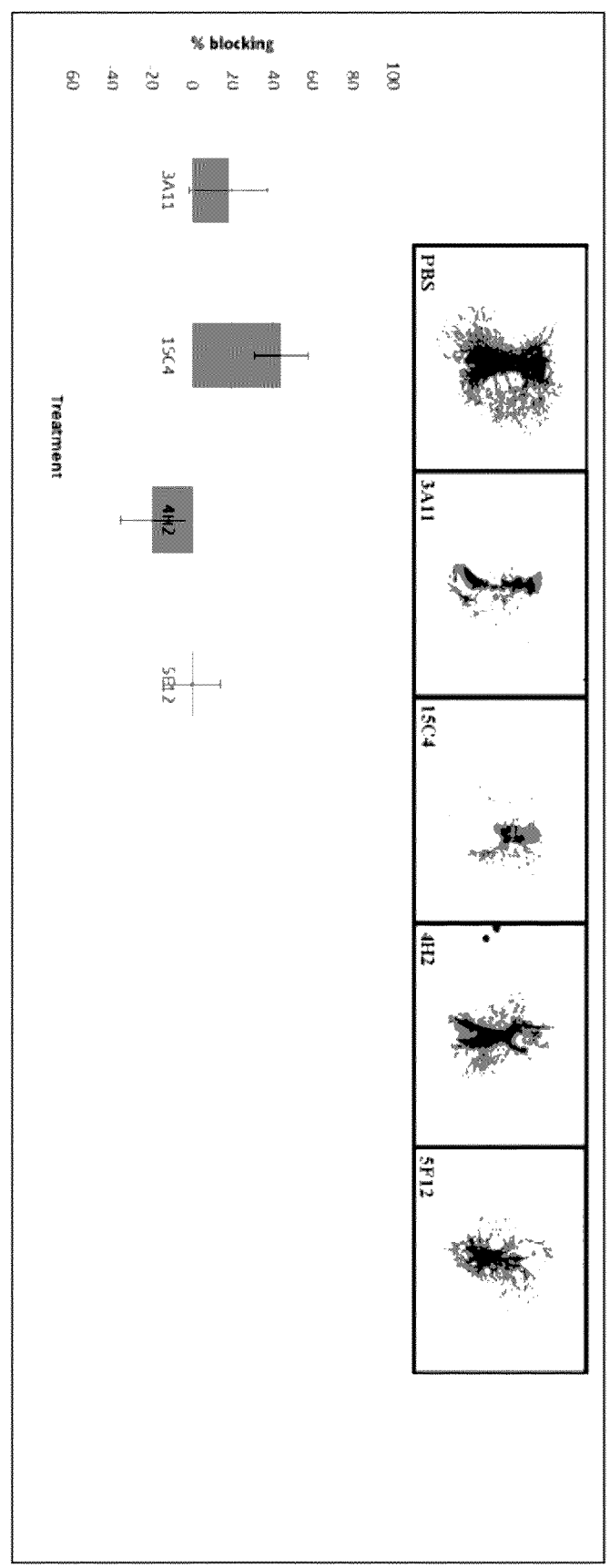
FIG. 3: Antibody blockade of angiogenesis in the mouse metatarsal assay. Bar chart shows quantification of blocking by mAbs 3A11 and 15C4. Representative images are shown, including image of PBS normalisation control.

FIG. 3 shows that 15C4 and 3A11 inhibited angiogenesis in this assay, to a maximum value of ~40% for 15C4. 4H2 and 5F12 had no effect, but note that 5F12 does not recognize mouse Lrg1 and 4H2 does so very weakly. The Inventors have previously shown that only ~25% suppression of angiogenesis is observed in metatarsals from the Lrg1-/- mouse (Wang et al., 2013). Thus the effects of 15C4 and 3A11 probably reflect the theoretical maximum effect.

Example 5—Specificity for Human Lrg1

To evaluate the specificity of the lead mAbs for human Lrg1 western blot analysis of each was performed against conditioned medium from the MDA-MB human tumour cell line, samples of human vitreous humour, and samples of whole human serum. FIG. 4 shows that 3A11 and 15C4 strongly recognise a single band of Lrg1 at 50 kD in the conditioned medium and vitreous. 4H2 works less well on blotting, but also shows specificity for Lrg1. The identification of a single band in the vitreous samples suggests suitability for therapeutic administration of these mAbs.

Example 6—Binding Kinetics

The four lead mAbs were examined using Biacore, in experiments in which human Lrg1 was immobilized on the chip, and mAbs passed across at concentrations ranging from 20-100 nM. The Table below summarises the kinetic data.

| Treatment | Kinetics | | |
|---|---|---|---|
| | KD (nM) | Ka | Kd |
| 3A11 | 0.001732 | 1.17E+05 | 2.02E−07 |
| 15C4 | 0.001271 | 1.10E+05 | 1.40E−07 |
| 4H2 | 0.9285 | 4.12E+04 | 3.83E−05 |
| 5F12 | 0.05937 | 1.15E+05 | 6.80E−06 |

The binding affinities for human Lrg1 of the 4 candidate antibodies are: 3A11 1.7 pM, 15C4 1.2 pM, 4H2 930 pM and 5F12 59 pM. 3A11 and in particular 15C4 show very high affinity for human Lrg1.

Example 7—Functional Testing in Rat Laser-Induced Choroidal Neovascularisation (CNV)

Figure 5:
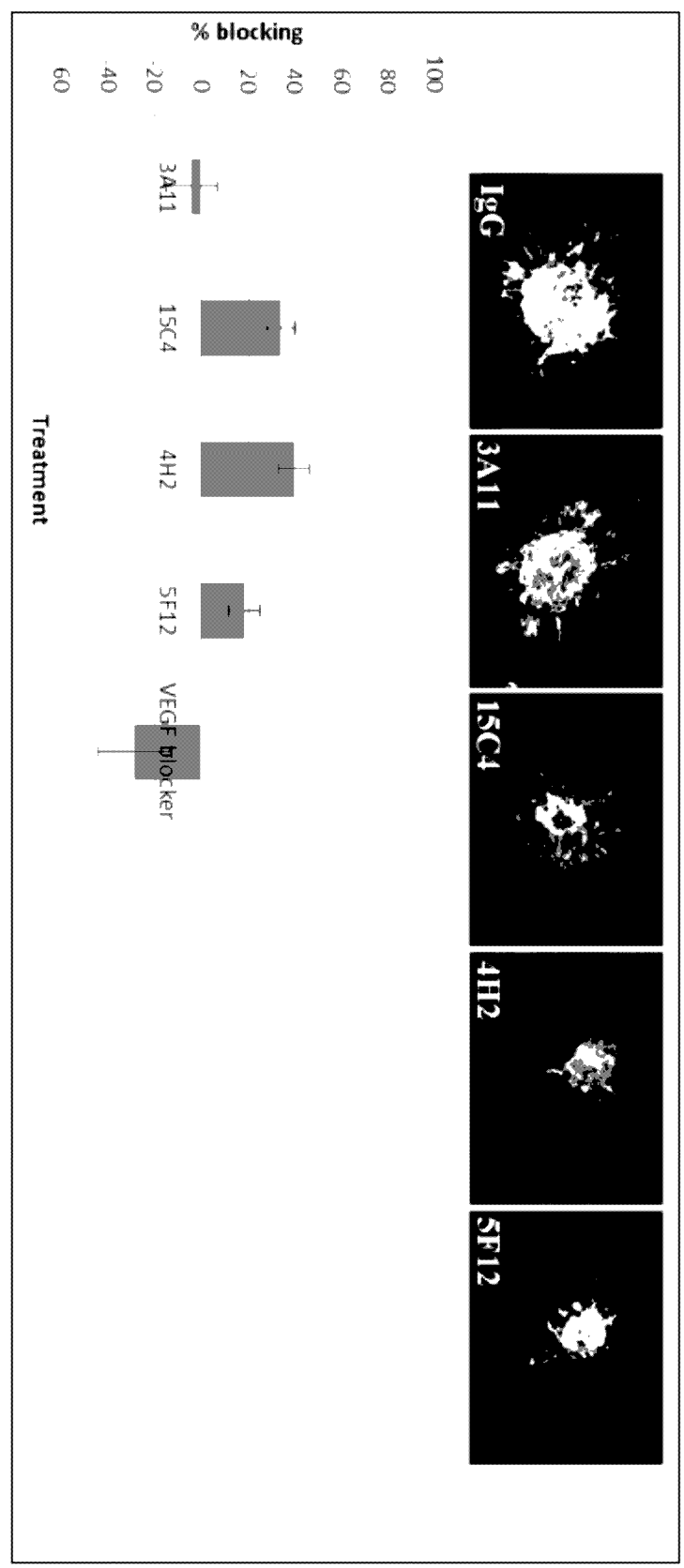
FIG. 5: Antibody blockade of angiogenesis in the rat model of laser-induced CNV. Bar chart shows quantification of blocking by mAbs 15C4, 4H2 and 5F12. Representative images are shown.

Several antibodies were tested for their ability to block CNV in the rat. In these experiments mAbs were injected intravitreally at the time of lasering, with eyes being retrieved for analysis 7 days later (FIG. 5). Long Evans rats, aged 6-8 weeks, each received 5 retinal laser burns at the same time as intravitreal delivery of 4 mg mAb or control IgG into both eyes. Four rats were used for each mAb, so a total of 40 lesions were analysed by staining for collagen IV and the neovascular areas quantified. The results show that a functional blockade of angiogenesis for 15C4, 4H2 and 5F12, but not for 3A11, is observed. The lack of effect for 3A11 should be considered in light of its weak cross-reactivity with rodent Lrg1. A Vascular endothelial growth factor (VEGF)-blocking antibody was also tested and found to have no functional effect in the assay. Avastin was also tested in the rat laser model (data not shown) and observed to have no effect, consistent with Avastin having low affinity for rat VEGF.

The top four mAbs exhibit functional activity in the metatarsal and CNV models. These mAbs, and 15C4 in particular, have therapeutically and clinically relevant properties. It has been established that Lrg1 gene knockout leads to only a ~25% reduction in angiogenesis in the metatarsal assay, suggesting that 25% inhibition should be the maximum achievable through antibody blockade. However 15C4 surpasses this value, and 3A11 comes close. In the CNV model 4 µg of 15C4 or 4H2 yields effective blockade following intraocular injection, whilst an anti-rat VEGF-blocking mAb does not.

A dose of 4 µg would be anticipated to generate an immediate intraocular concentration of ~1.0 µM assuming a vitreous volume of 25 µl and mAb molecular weight of 150 kD. However, the intraocular concentration of injected mAbs is known to rapidly decline, so the effective concentration of mAb once CNV starts to develop (after a few days) is inevitably much lower. Moreover, Lucentis is injected into patients with neovascular AMD to give a vitreal concentration of ~2.6 µM. The strategy was therefore based on clinically relevant therapeutic dosing.

Example 8—HUVEC Co-Culture Model of Angiogenesis

Figure 6:
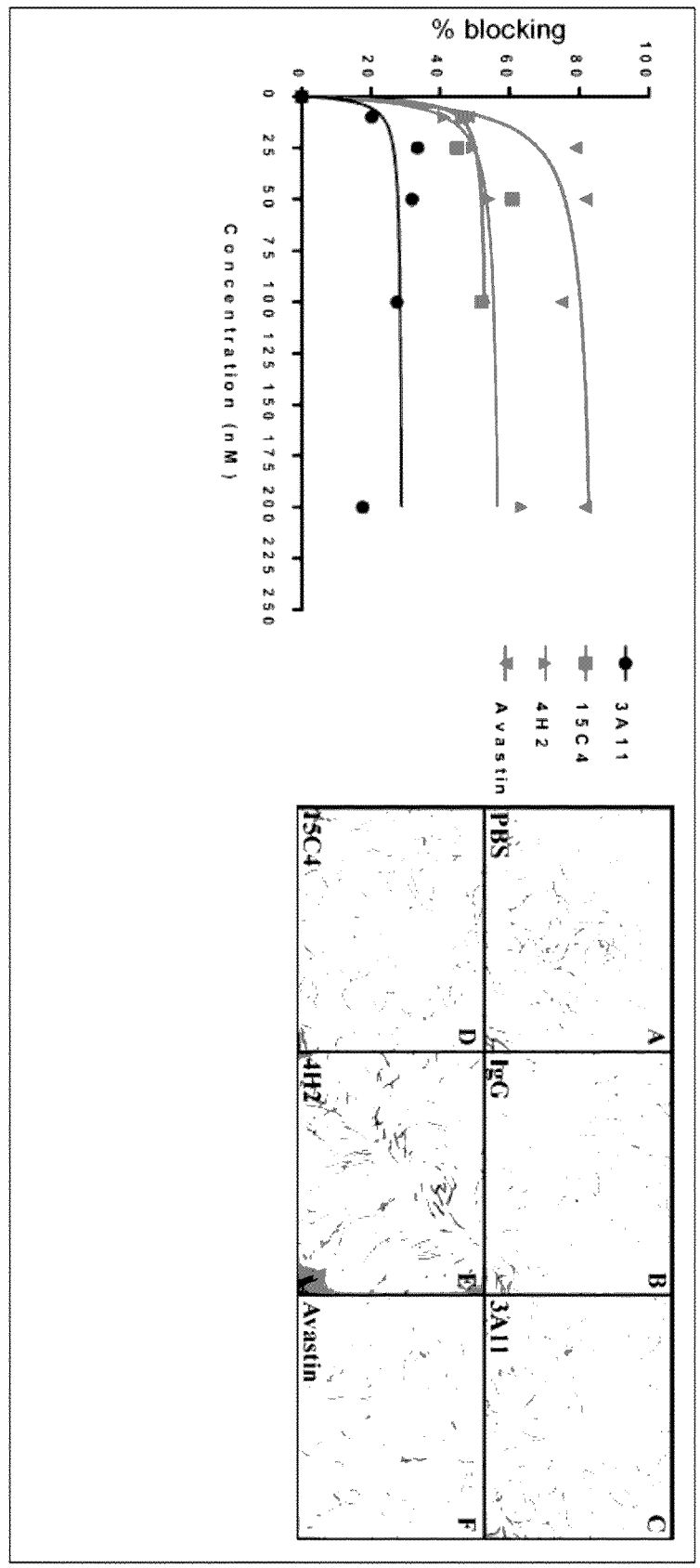
FIG. 6: Antibody blockade of vessel growth in the co-culture model of angiogenesis. HUVEC were co-cultured with human fibroblasts for 14 days, and then fixed and immunostained with an antibody against PECAM. Avastin was included as a positive control, and all four mAbs were tested at 10, 25, 50, 100 and 200 nM. Data were collected for n-8 individual wells in 24-well culture plates. Representative images from the 25 nM wells are shown.

Antibodies 4H2, 15C4 and 3A11 were tested to see if they elicited an inhibition of vessel growth in the co-culture model of angiogenesis. HUVEC were co-cultured with human fibroblasts for 14 days, and then fixed and immunostained with an antibody against PECAM. Avastin was included as a positive control, and all four mAbs were tested at 10, 25, 50, 100 and 200 nM. The results are shown in FIG. 6. There were two important observations from this experiment. The first is that 3A11 was relatively ineffective in this assay, and the second is that 15C4 and 4H2 were equally effective.

4H2 and 15C4 were found to be promising therapeutics and therefore suitable for humanization. 4H2 has the lower affinity for human Lrg1 (though it still binds with high affinity) but shows better cross-reactivity with rodent Lrg1, making future toxicology testing more straightforward. On the other hand 15C4 has a much higher affinity for human Lrg1, but is less efficacious than 4H2 in the in vivo rodent models of angiogenesis.

Example 9: Epitope Mapping of Candidate Antibodies

Epitope mapping for the 4H2, 15C4 and 3A11 antibodies was carried out. Antibody-antigen interactions are a key event in immunology. Therefore, the identification of epitopes or immunodominant regions in antigens represents an important step in the characterization of potential antibody development. One of the most efficient ways to identify such epitopes is by the incubation of a collection of antigen-derived peptides displayed on peptide microarrays with purified polyclonal or monoclonal antibodies, or complex biological mixtures (i.e. sera/plasma) of interest.

The determination of peptide-antibody binding was performed by incubation of serum or antibody samples with a ProArray Ultra® peptide microarray, followed by incubation with a fluorescent-labelled secondary antibody.

All peptides were synthesized separately, and then bound to the ProArray Ultra® slide surface using ProImmune's proprietary technology. This optimised process ensured that peptides were presented on the array in such a manner as to closely mimic the properties of the corresponding protein region, circumventing the inherent physiochemical variation of the free peptides themselves and making a compatible, combined peptide and protein array platform. The test analytes (peptides or proteins) were dispensed onto the ProArray Ultra® slide in discrete spots and appropriate gal-files enabled exact alignment of the resulting array features back to the analyte deposited.

ProArray Ultra® slides were blocked using a validated blocking buffer to reduce non-specific binding of the sera. They were then incubated with test samples, followed by incubation with a specific fluorescent-labelled secondary antibody. After several washing steps, the ProArray Ultra® arrays were dried and scanned using a high-resolution fluorescence microarray scanning system.

Overlapping peptides representing LRG1 were synthesized and printed onto ProArray Ultra® microarray slides, alongside selected murine IgG controls. Slides were incubated with murine monoclonal antibody samples 4H2, 15C4 and 3A11 to identify putative epitopes. An overlapping peptide library representing Lrg1 was synthesized from the sequence provided by the sponsor. 15-mer synthetic peptides, overlapping by 10 amino acids, were generated.

ProArray Ultra® slides containing the immobilised peptides were incubated with the antibody samples. All incubation slides resulted in detectable signals above the positive threshold level of 3× background (defined as Average Signal Intensity above 3× Average Signal Intensity of the corresponding negative control features). The murine IgG positive controls were detected in all samples. No significant interaction was observed between any peptides and the secondary detection antibody on the control incubations. Therefore, no epitopes were discarded due to non-specific binding to the secondary detection antibody.

Full length Lrg1 was identified as a binder at all dilutions of the 4H2, 15C4 and 3A11 antibodies.

One peptide was identified as a hit for three of the 4H2, 15C4 and 3A11 antibodies, GNKLQVLGKDLLLPQ (SEQ ID NO: 30), amino acids 221-235 of Lrg1.

Example 10—Humanization of Antibody 15C4

Variable region genes from the 15C4 hybridoma were cloned and sequenced, resulting in the identification of a single unique sequence each for VH and Vκ Identified Variable region genes were cloned into vectors to generate a chimeric antibody comprising the murine Variable regions combined with the human IgG4 (S241P) heavy chain constant region and Kappa light chain constant regions. Additionally, a series of five humanised VH regions and three humanised Vκ regions were designed using Composite Human Antibody™ technology.

The chimeric antibody was expressed transiently in HEK EBNA cells and stably in NS0 mouse myeloma cells, purified and tested for binding to human Lrg1 in a competition ELISA assay. A Nunc Immuno MaxiSorp 96 well flat bottom microtitre plate (Fisher, cat. no. DIS-971-030J) was pre-coated with 0.2 µg/ml hLrg1 (supplied by UCL) overnight in 0.1 N Sodium Carbonate buffer (NaHCO$_3$) at +4° C. The following day the plate was washed 1× with PBST and blocked with 3% BSA/PBS for 1 hour at room temperature. After washing 3× with PBST, a three-fold dilution series of chimeric, mouse or control antibodies from 100 µg/ml to 0.13 µg/ml was premixed with a constant concentration of biotinylated mouse 15C4 (0.4 µg/ml, final concentration), added to the plates and incubated for 1.5 hours at room temperature. Following 3×PBST washes, the binding of the biotinylated mAb was detected with streptavidin-HRP (Sigma, cat. no. 55512) and TMB substrate (Invitrogen, cat. no. 00-2023). The reaction was stopped with 3 M HCl, absorbance read at 450 nm on a Dynex Technologies MRX TC II plate reader and the binding curves plotted.

Figure 7A:
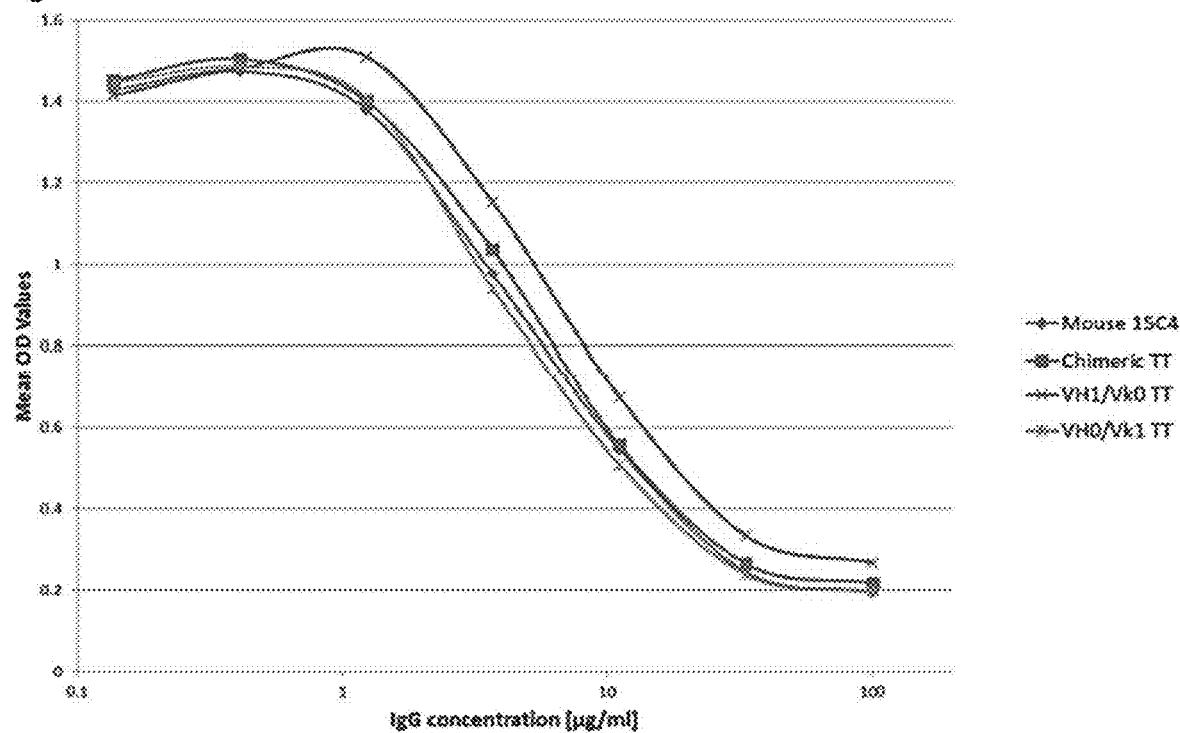
FIG. 7A—Mouse 15C4 antibody, transiently expressed (TT) chimeric and control antibodies (VH1/Vk0; VH1—SEQ ID NO: 5, Vk0—SEQ ID NO: 2, and VH0/Vk1; VH0-SEQ ID NO: 1, Vk1—SEQ ID NO: 15).
Figure 7B:
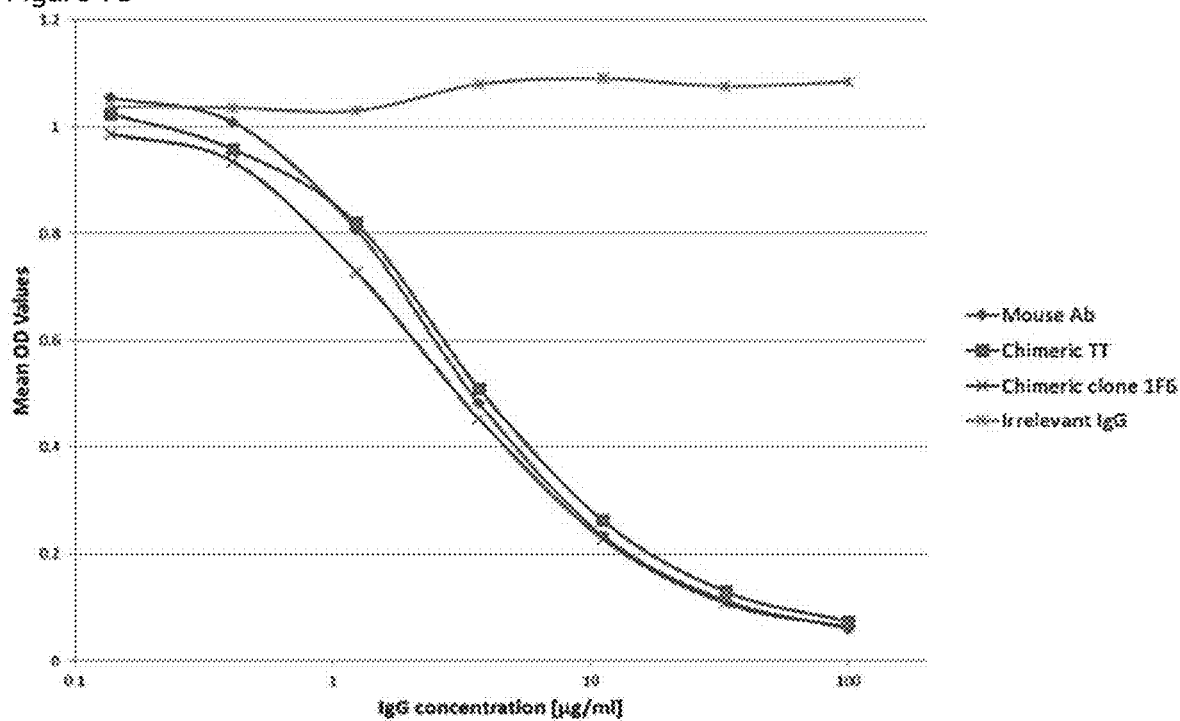
FIG. 7B—Mouse 15C4 antibody, stable (NS0 clone 1F6) and transiently expressed (TT) chimeric antibody and an irrelevant IgG4 antibody, negative control.
Figure 8A:
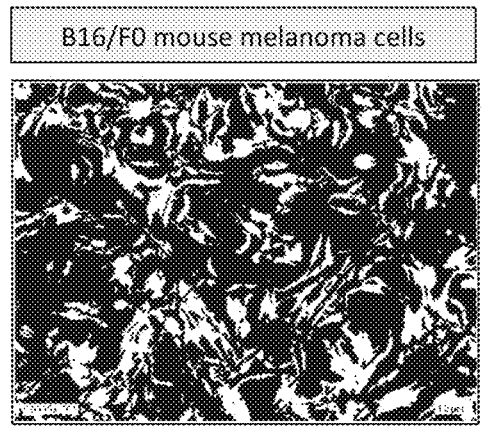
FIG. 8A—image of B16/F0 mouse melanoma cells, FIG. 8B—images of co-stained CD31(blood vessel) and DAPI (cell nuclei) sections of B16/F0 tumour in wildtype and Lrg1 knockout mice.
Figure 8B:
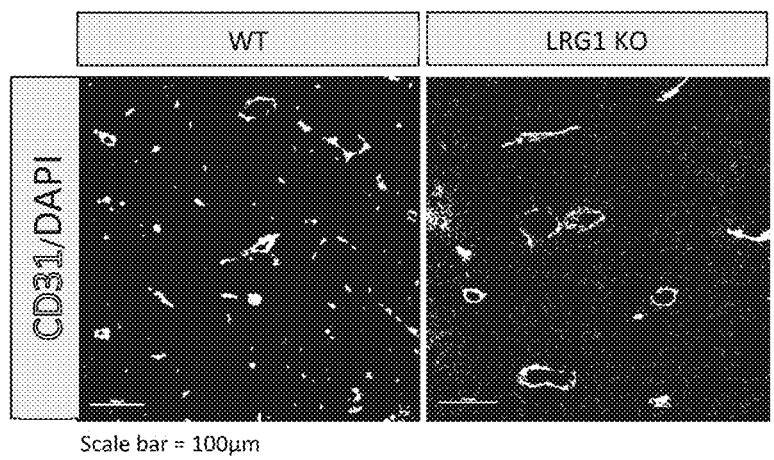
FIG. 8: Lrg1 and angiogenesis in B16/F0 and LL/2 tumours.
FIG. 8C—bar chart of number of blood vessels in B16/F0 tumour in wildtype and Lrg1 knockout mice.
FIG. 8D—image of LL/2 mouse lung carcinoma cells, FIG. 8E—images of co-stained CD31(blood vessel) and DAPI (cell nuclei) sections of LL/2 tumour in wildtype and Lrg1 knockout mice.
FIG. 8F—bar chart of number of blood vessels in LL/2 tumour in wildtype and Lrg1 knockout mice.
Figure 8C:
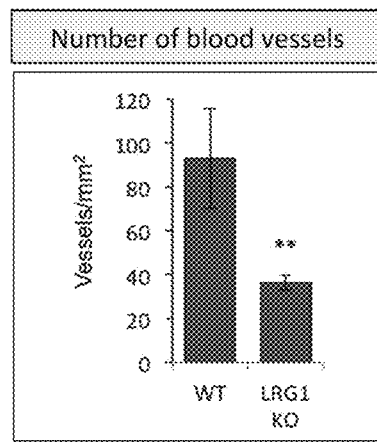
Figure 8D:
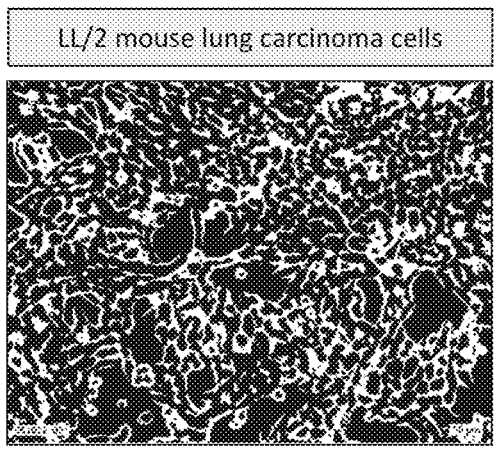
Figure 8E:
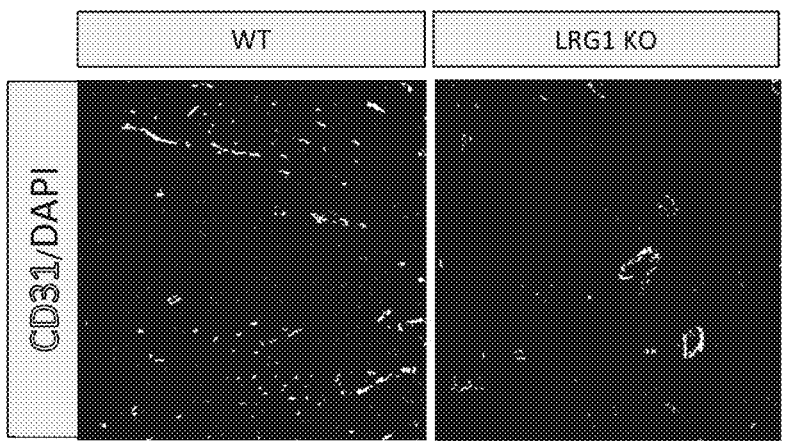
Figure 8F:
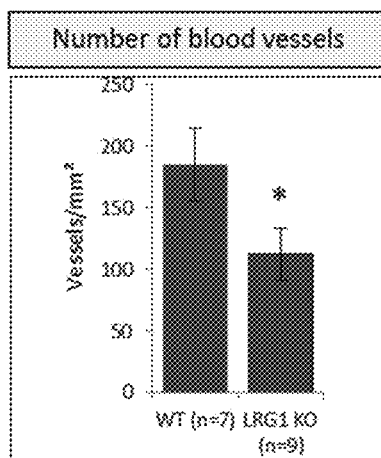

A comparison of the chimeric and mouse antibodies (FIG. 7) showed that chimeric and control antibodies have a very similar binding profile to mouse 15C4 and the IC$_{50}$ values are within 2-fold. This indicated that the correct variable region sequences had been identified and cloned. An irrelevant human IgG4 antibody did not compete for binding to human Lrg1.

Example 11—Summary of Sequence Information

For each antibody described below, CDRs are bold and underlined in the amino acid sequences.

```
Antibody 15C4
Variable heavy chain (V_H) amino acid sequence
                                                              SEQ ID NO: 1
QVQLQQSGDEVVRPGSSVKISCKASGYTFSGYWMNWVKQRPGQGLQWIGQIYPGDGDTNYNGKFKGKATLTAD
```

KSSSTAYMQLSTLTSEDSAIYFCARSITTVVLDYWGQGTTLTVSS

Variable light chain (V<sub>L</sub>) amino acid sequence
SEQ ID NO: 2
DIVLTQSPVSLAVSLGQRATISCRASQSVSTSGYSFMHWYQQKPGQPPKFLIKYASNLESGVPARFSGSGT
DFTLNIHPVEEEDTATYYCQHSWEMPLTFGAGTKLELK Variable heavy chain (V<sub>H</sub>) nucleotide sequence
SEQ ID NO: 3
CAGGTTCAACTGCAGCAGTCTGGGGATGAGGTGGTGAGGCCTGGGTCCTCAGTGAAGATTTCCTGTAAGGCTT
CTGGCTATACATTCAGTGGCTACTGGATGAACTGGGTGAAACAGAGGCCTGGACAGGGTCTTCAGTGGATTGG
ACAGATTTATCCTGGAGATGGTGATACTAACTACAATGGAAAATTCAAGGGTAAAGCCACACTGACTGCAGAC
AAATCCTCCAGCACAGCCTACATGCAGCTCAGCACCCTAACATCTGAGGACTCTGCGATCTATTTCTGTGCAA
GATCGATTACTACGGTAGTCCTTGACTACTGGGGCCAAGGCACCACTCTCACAGTCTCCTCA Variable light chain (V<sub>L</sub>) nucleotide sequence
SEQ ID NO: 4
GACATTGTGCTGACACAGTCTCCTGTTTCCTTAGCTGTATCTCTGGGTCAGAGGGCCACCATCTCATGCAGGG
CCAGCCAAAGTGTCAGTACATCTGGCTATAGTTTTATGCACTGGTACCAACAGAAACCAGGACAGCCACCCAA
ATTCCTCATCAAGTATGCATCCAACCTAGAATCTGGGGTCCCTGCCAGGTTCAGTGGCAGTGGGTCTGGGACA
GACTTCACCCTCAACATCCATCCTGTGGAGGAGGAGGATACTGCAACATATTACTGTCAGCACAGTTGGGAGA
TGCCTCTCACGTTCGGTGCTGGGACCAAGCTGGAGCTGAAA CDR amino acid sequences
V<sub>H</sub> CDRs:
CDR1:
(SEQ ID NO: 21)
GYWMN

CDR2:
(SEQ ID NO: 22)
QIYPGDGDTNYNGKFKG

CDR3:
(SEQ ID NO: 23)
SITTVVLDY

V<sub>L</sub> CDRs:
CDR1:
(SEQ ID NO: 24)
RASQSVSTSGYSFMH

CDR2:
(SEQ ID NO: 25)
YASNLES

CDR3:
(SEQ ID NO: 26)
QHSWEMPLT

Humanised 15C4 Antibodies
Variable heavy chain (V<sub>H</sub>) amino acid sequence VH1
SEQ ID NO: 5
QVQLVQSGDEVKKPGSSVKVSCKASGYTFSGYWMNWVKQAPGQGLQWIGQIYPGDGDTNYNGKFKGRATITAD
KSTSTAYMQLSTLTSEDSAIYFCARSITTVVLDYWGQGTTVTVSS Variable heavy chain (V<sub>H</sub>) nucleotide sequence VH1
SEQ ID NO: 6
GTTGCTACGCGTGTCCACTCCCAGGTTCAACTGGTGCAGTCTGGGGATGAGGTGAAGAAGCCTGGGTCCTCAG
TGAAGGTGTCCTGTAAGGCTTCTGGCTATACATTCAGTGGCTACTGGATGAACTGGGTGAAACAGGCCCCTGG
ACAGGGTCTTCAGTGGATTGGACAGATTTATCCTGGAGATGGTGATACTAACTACAATGGAAAATTCAAGGGT
CGGGCCACAATCACTGCCGACAAATCCACCAGCACAGCCTACATGCAGCTCAGCACCCTAACATCTGAGGACT
CTGCGATCTATTTCTGTGCAAGATCGATTACTACGGTAGTCCTTGACTACTGGGGCCAAGGCACCACCGTCAC
GGTCTCCTCAGGTAAGCTTTCTGGG

```
CDR amino acid sequences
V_H CDRs:
CDR1:
                                                         (SEQ ID NO: 21)
GYWMN CDR2:
                                                         (SEQ ID NO: 22)
QIYPGDGDTNYNGKFKG CDR3:
                                                         (SEQ ID NO: 23)
SITTVVLDY Variable heavy chain (V_H) amino acid sequence VH2
                                                         SEQ ID NO: 7
QVQLVQSGDEVKKPGSSVKVSCKASGYTFSGYWMNWVKQAPGQGLQWIGQIYPGDGDTNYNGKFKGRATITAD

KSTSTAYMELSSLTSEDTAIYFCARSITTVVLDYWGQGTTVTVSS

Variable heavy chain (V_H) nucleotide sequence VH2
                                                         SEQ ID NO: 8
GTTGCTACGCGTGTCCACTCCCAGGTTCAACTGGTGCAGTCTGGGGATGAGGTGAAGAAGCCTGGGTCCTCAG

TGAAGGTGTCCTGTAAGGCTTCTGGCTATACATTCAGTGGCTACTGGATGAACTGGGTGAAACAGGCCCCTGG

ACAGGGTCTTCAGTGGATTGGACAGATTTATCCTGGAGATGGTGATACTAACTACAATGGAAAATTCAAGGGT

CGGGCCACAATCACTGCCGACAAATCCACCAGCACAGCCTACATGGAGCTCAGCTCCCTAACATCTGAGGACA

CCGCGATCTATTTCTGTGCAAGATCGATTACTACGGTAGTCCTTGACTACTGGGGCCAAGGCACCACCGTCAC

GGTCTCCTCAGGTAAGCTTTCTGGG

CDR amino acid sequences
V_H CDRs:
CDR1:
                                                         (SEQ ID NO: 21)
GYWMN CDR2:
                                                         (SEQ ID NO: 22)
QIYPGDGDTNYNGKFKG CDR3:
                                                         (SEQ ID NO: 23)
SITTVVLDY Variable heavy chain (V_H) amino acid sequence VH3
                                                         SEQ ID NO: 9
QVQLVQSGAEVKKPGSSVKVSCKASGYTFSGYWMNWVRQAPGQGLQWIGQIYPGDGDTNYNGKFKGRVTITAD

KSTSTAYMELSSLTSEDTAIYFCARSITTVVLDYWGQGTTVTVSS

Variable heavy chain (V_H) nucleotide sequence VH3
                                                         SEQ ID NO: 10
GTTGCTACGCGTGTCCACTCCCAGGTTCAACTGGTGCAGTCTGGGGCTGAGGTGAAGAAGCCTGGGTCCTCAG

TGAAGGTGTCCTGTAAGGCTTCTGGCTATACATTCAGTGGCTACTGGATGAACTGGGTGCGGCAGGCCCCTGG

ACAGGGTCTTCAGTGGATTGGACAGATTTATCCTGGAGATGGTGATACTAACTACAATGGAAAATTCAAGGGT

AGAGTGACAATCACTGCCGACAAATCCACCAGCACAGCCTACATGGAGCTCAGCTCCCTAACATCTGAGGACA

CCGCGATCTATTTCTGTGCAAGATCGATTACTACGGTAGTCCTTGACTACTGGGGCCAAGGCACCACGGTCAC

CGTCTCCTCAGGTAAGCTTTCTGGG

CDR amino acid sequences
V_H CDRs:
CDR1:
                                                         (SEQ ID NO: 21)
GYWMN CDR2:
                                                         (SEQ ID NO: 22)
QIYPGDGDTNYNGKFKG CDR3:
                                                         (SEQ ID NO: 23)
SITTVVLDY
```

Variable heavy chain (V_H) amino acid sequence VH4
SEQ ID NO: 11
QVQLVQSGAEVKKPGSSVKVSCKASGYTFSGYWMNWVRQAPGQGLEWIGQIYPGDGDTNYNGKFKGRVTITAD

KSTSTAYMELSSLTSEDTAIYYCARSITTVVLDYWGQGTTVTVSS

Variable heavy chain (V_H) nucleotide sequence VH4
SEQ ID NO: 12
GTTGCTACGCGTGTCCACTCCCAGGTTCAACTGGTGCAGTCTGGGGCTGAGGTGAAGAAGCCTGGGTCCTCAG

TGAAGGTGTCCTGTAAGGCTTCTGGCTATACATTCAGTGGCTACTGGATGAACTGGGTGCGGCAGGCCCCTGG

ACAGGGTCTTGAGTGGATTGGACAGATTTATCCTGGAGATGGTGATACTAACTACAATGGAAAATTCAAGGGT

AGAGTGACAATCACTGCCGACAAATCCACCAGCACAGCCTACATGGAGCTCAGCTCCCTAACATCTGAGGACA

CCGCGATCTATTACTGTGCAAGATCGATTACTACGGTAGTCCTTGACTACTGGGGCCAAGGCACCACGGTCAC

CGTCTCCTCAGGTAAGCTTTCTGGG

CDR amino acid sequences
V_H CDRs:
CDR1:
(SEQ ID NO: 21)
GYWMN

CDR2:
(SEQ ID NO: 22)
QIYPGDGDTNYNGKFKG

CDR3:
(SEQ ID NO: 23)
SITTVVLDY

Variable heavy chain (V_H) amino acid sequence VH5
SEQ ID NO: 13
QVQLVQSGAEVKKPGSSVKVSCKASGYTFSGYWMNWVRQAPGQGLEWIGQIYPGDGDTNYNGKFKGRVTITAD

KSTSTAYMELSSLRSEDTAVYYCARSITTVVLDYWGQGTTVTVSS

Variable heavy chain (V_H) nucleotide sequence VH5
SEQ ID NO: 14
GTTGCTACGCGTGTCCACTCCCAGGTTCAACTGGTGCAGTCTGGGGCTGAGGTGAAGAAGCCTGGGTCCTCAG

TGAAGGTGTCCTGTAAGGCTTCTGGCTATACATTCAGTGGCTACTGGATGAACTGGGTGCGGCAGGCCCCTGG

ACAGGGTCTTGAGTGGATTGGACAGATTTATCCTGGAGATGGTGATACTAACTACAATGGAAAATTCAAGGGT

AGAGTGACAATCACTGCCGACAAATCCACCAGCACAGCCTACATGGAGCTCAGCTCCCTACGGTCTGAGGACA

CCGCGGTGTATTACTGTGCAAGATCGATTACTACGGTAGTCCTTGACTACTGGGGCCAAGGCACCACGGTCAC

CGTCTCCTCAGGTAAGCTTTCTGGG

CDR amino acid sequences
V_H CDRs:
CDR1:
(SEQ ID NO: 21)
GYWMN

CDR2:
(SEQ ID NO: 22)
QIYPGDGDTNYNGKFKG

CDR3:
(SEQ ID NO: 23)
SITTVVLDY

Variable light chain (V_L) amino acid sequence VK1
SEQ ID NO: 15
DIVLTQSPDSLAVSLGERATISCRASQSVSTSGYSFMHWYQQKPGQPPKFLIKYASNLESGVPARFSGSGSGT

DFTLTISSLQEEDFATYYCQHSWEMPLTFGQGTKLEIK

Variable light chain (V_L) nucleotide sequence VK1
SEQ ID NO: 16
CTCCCAGGCGCGCGATGTGACATTGTGCTGACACAGTCTCCTGACTCCTTAGCTGTATCTCTGGGTGAGAGGG

CCACCATCTCATGCAGGGCCAGCCAAAGTGTCAGTACATCTGGCTATAGTTTTATGCACTGGTACCAACAGAA

-continued
```
ACCAGGACAGCCACCCAAATTCCTCATCAAGTATGCATCCAACCTAGAATCTGGGGTCCCTGCCAGGTTCAGT

GGCAGTGGGTCTGGGACAGACTTCACCCTCACCATCTCTTCTCTGCAGGAGGAGGATTTCGCAACATATTACT

GTCAGCACAGTTGGGAGATGCCTCTCACGTTCGGCCAGGGGACCAAGCTGGAGATCAAACGTGAGTAGAATTT

AAACTTTGCTTCCTCAGTTGGATCCCGC
```

CDR amino acid sequences
V$_L$ CDRs:
CDR1:
(SEQ ID NO: 24)
RASQSVSTSGYSFMH

CDR2:
(SEQ ID NO: 25)
YASNLES

CDR3:
(SEQ ID NO: 26)
QHSWEMPLT

Variable light chain (V$_L$) amino acid sequence VK2
SEQ ID NO: 17
DIVLTQSPDSLAVSLGERATISCRASQSVSTSGYSFMHWYQQKPGQPPKFLIKYASNLESGVPARFSGSGSGT
DFTLTISSLQPEDFATYYCQHSWEMPLTFGQGTKLEIK Variable light chain (V$_L$) nucleotide sequence VK2
SEQ ID NO: 18
```
CTCCCAGGCGCGCGATGTGACATTGTGCTGACACAGTCTCCTGACTCCTTAGCTGTATCTCTGGGTGAGAGGG

CCACCATCTCATGCAGGGCCAGCCAAAGTGTCAGTACATCTGGCTATAGTTTTATGCACTGGTACCAACAGAA

ACCAGGACAGCCACCCAAATTCCTCATCAAGTATGCATCCAACCTAGAATCTGGGGTCCCTGCCAGGTTCAGT

GGCAGTGGGTCTGGGACAGACTTCACCCTCACCATCTCTTCTCTGCAGCCCGAGGATTTCGCAACATATTACT

GTCAGCACAGTTGGGAGATGCCTCTCACGTTCGGCCAGGGGACCAAGCTGGAGATCAAACGTGAGTAGAATTT

AAACTTTGCTTCCTCAGTTGGATCCCGC
```

CDR amino acid sequences
V$_L$ CDRs:
CDR1:
(SEQ ID NO: 24)
RASQSVSTSGYSFMH

CDR2:
(SEQ ID NO: 25)
YASNLES

CDR3:
(SEQ ID NO: 26)
QHSWEMPLT

Variable light chain (V$_L$) amino acid sequence VK3
SEQ ID NO: 19
DIVLTQSPDSLAVSLGERATISCRASQSVSTSGYSFMHWYQQKPGQPPKLLIKYASNLESGVPARFSGSGSGT
DFTLTISSLQPEDFATYYCQHSWEMPLTFGQGTKLEIK Variable light chain (V$_L$) nucleotide sequence VK3
SEQ ID NO: 20
```
CTCCCAGGCGCGCGATGTGACATTGTGCTGACACAGTCTCCTGACTCCTTAGCTGTATCTCTGGGTGAGAGGG

CCACCATCTCATGCAGGGCCAGCCAAAGTGTCAGTACATCTGGCTATAGTTTTATGCACTGGTACCAACAGAA

ACCAGGACAGCCACCCAAACTGCTCATCAAGTATGCATCCAACCTAGAATCTGGGGTCCCTGCCAGGTTCAGT

GGCAGTGGGTCTGGGACAGACTTCACCCTCACCATCTCTTCTCTGCAGCCCGAGGATTTCGCAACATATTACT

GTCAGCACAGTTGGGAGATGCCTCTCACGTTCGGCCAGGGGACCAAGCTGGAGATCAAACGTGAGTAGAATTT

AAACTTTGCTTCCTCAGTTGGATCCCGC
```

CDR amino acid sequences
V$_L$ CDRs:
CDR1:
(SEQ ID NO: 24)
RASQSVSTSGYSFMH

-continued

CDR2:
(SEQ ID NO: 25)
YASNLES

CDR3:
(SEQ ID NO: 26)
QHSWEMPLT

Exemplary constant regions of antibodies of the invention

Constant heavy chain (C$_H$) amino acid sequence (Igγ 2-4_HUMAN)
SEQ ID NO: 27
Published in Mueller J. P. et al. Molecular Immunology vol. 34 no. 6
pp 441-452, 1997
ASTKGPSVFPLAPCSRSTSESTAALGCLVKDYFPEPVTVSWNSGALTSGVHTFPAVLQSSGLYSLSSVVTVPS

SNFGTQTYTCNVDHKPSNTKVDKTVERKCCVECPPCPAPPVAGPSVFLFPPKPKDTLMISRTPEVTCVVVDVS

QEDPEVQFNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYSRLTVD

KSRWQEGNVFSCSVMHEALHNHYTQKSLSLSLGK

Constant heavy chain (C$_H$) amino acid sequence (Igγ-1_Uniprot accession
number: P01857_HUMAN)
SEQ ID NO: 28
ASTKGPSVFPLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPGK

Constant light chain (C$_L$) amino acid sequence (Igκ chain C region Genbank
accessison number: AAA58989.1_HUMAN)
SEQ ID NO: 29
TVAAPSVFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC

Amino acid sequence of human Lrg1, NCBI ref: NP_443204.1
SEQ ID NO: 31
Epitope of Lrg1 identified in Example 9 in bold and underlined.
MSSWSRQRPKSPGGIQPHVSRTLFLLLLLAASAWGVTLSPKDCQVFRSDHGSSISCQPPAEIPGYLPADTVHL

AVEFFNLTHLPANLLQGASKLQELHLSSNGLESLSPEFLRPVPQLRVLDLTRNALTGLPPGLFQASATLDTLV

LKENQLEVLEVSWLHGLKALGHLDLSGNRLRKLPPGLLANFTLLRTLDLGENQLETLPPDLLRGPLQLERLHL

EGNKLQVLGKDLLLPQPDLRYLFLNGNKLARVAAGAFQGLRQLDMLDLSNNSLASVPEGLWASLGQPNWDMRD

GFDISGNPWICDQNLSDLYRWLQAQKDKMFSQNDTRCAGPEAVKGQTLLAVAKSQ

The humanised 15C4 antibody comprising heavy chain variable regions VH5 and kappa light chain variable regions VK3 is called Magacizumab.

Example 12—Normalisation of Tumour Vascularisation in Lrg1 Knockout Mice and in Presence of Lrg1 Antagonist B16/F0 and LL/2 human tumour cell lines were grafted into wild type and Lrg1 knockout mice.

The resulting B16/F0 and LL/2 tumours showed a decrease in the number of blood vessels in the Lrg1 knockout when compared with the wild-type mouse (FIG. 8) CD31 (cluster of differentiation 31) is a marker for blood vessels, DAPI is a marker for cell nuclei. A visual inspection of the tumours suggested that there were fewer small vessels.

Figure 9A:
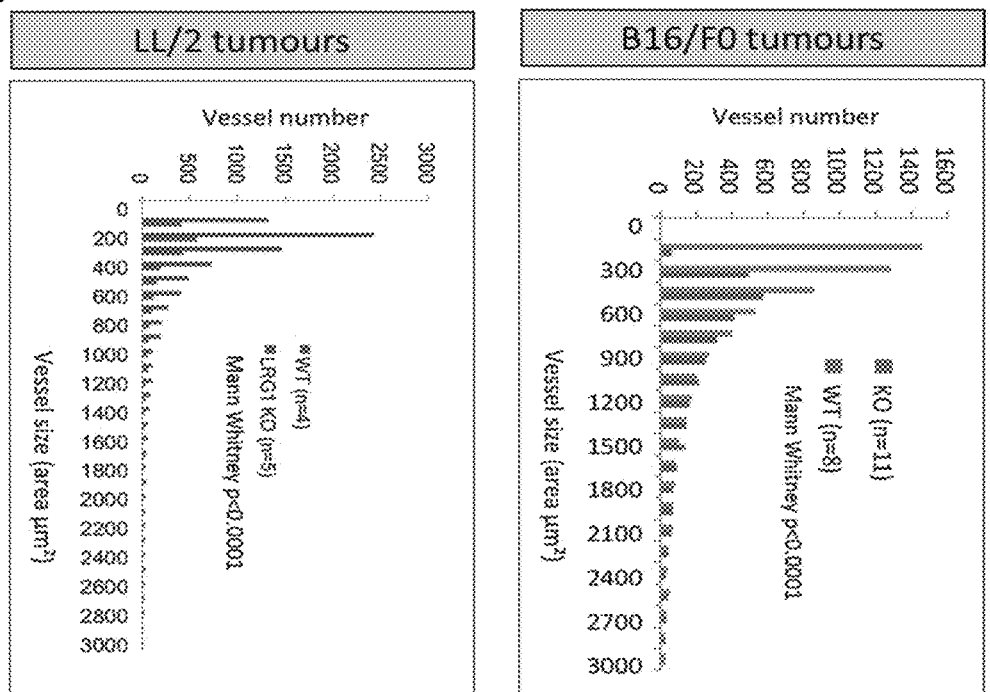
FIG. 9A—bar chart of vessel size vs vessel number in Lrg1 knockout (left bar per vessel size) and wildtype (right bar per vessel size).
Figure 9B:
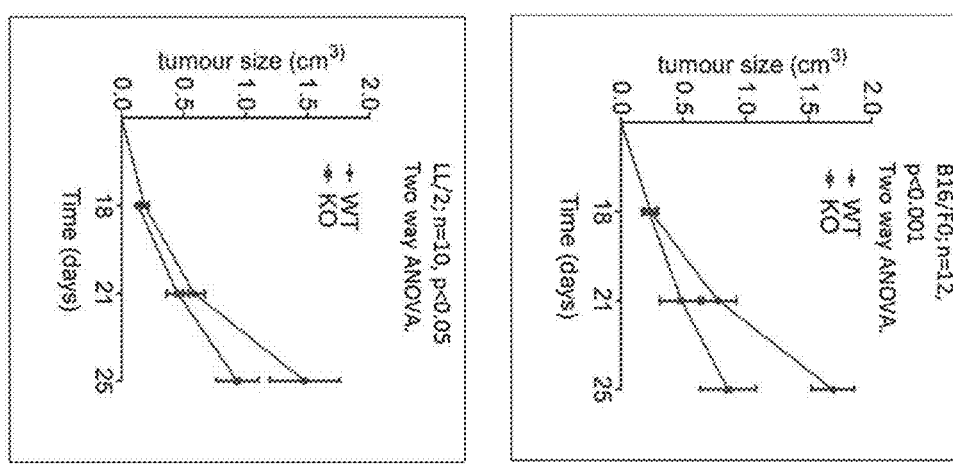
FIG. 9B—plot of tumour size over time, wildtype, top line, Lrg1 knockout, bottom line.
Figure 9C:
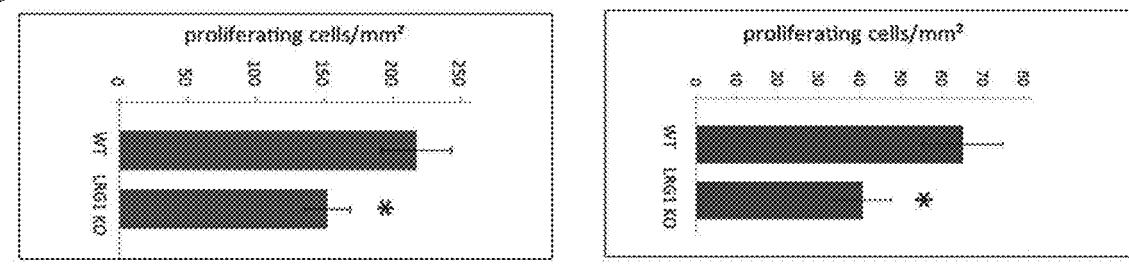
FIG. 9C, bar chart of proliferating cells per square mm, identified by the presence of phosphohistone H3, in wildtype and Lrg1 knockout.

When the vessel number and size was quantified it was shown that there was a disproportionate decrease in the number of smaller vessels in the Lrg1 knockout when compared with the wild type mouse, a massive loss of the smaller vessels (FIG. 9). Tumour size was significantly reduced and significantly fewer dividing cells, as measured by presence of phospho-histone H3, were found per tumour (FIG. 9).

These results were mimicked in B16/F0 and LL/2 tumours of wild type mice in the presence of antibody 15C4, used at a concentration of 50 mg per kg.

The adherent cell line B16/F0 was harvested and single-cell suspensions of $1 \times 10^6$ cells in 100 µl PBS was injected subcutaneously into the lower back of C57B1/6 mice. Tumours were measured every other day with a caliper and volume was calculated using the formula: $V=(4/3) \times \pi \times (L/2) \times (W/2) \times (H/2)$. The mice were sacrificed at defined time intervals or after the tumors reached 2000 mm$^3$. Treatment with 15C4 or IgG was started after three days at 50 mg/kg by intraperitoneal injections, and repeated every 3 days.

Figure 11:
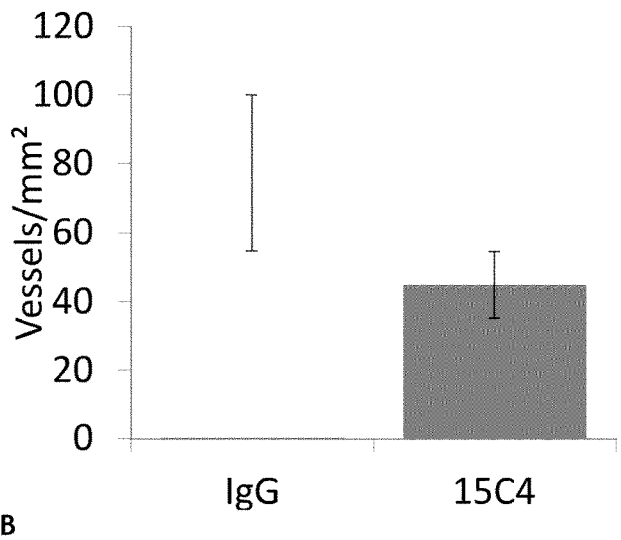
FIG. 11: 15C4 recapitulates the Lrg1 null phenotype.
Figure 11:
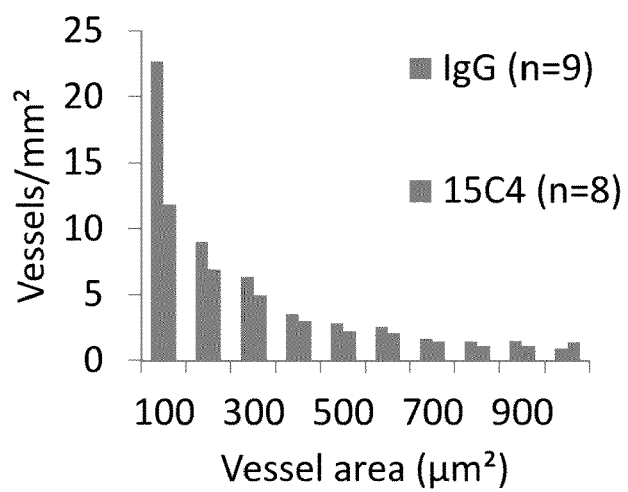
Figure 11:
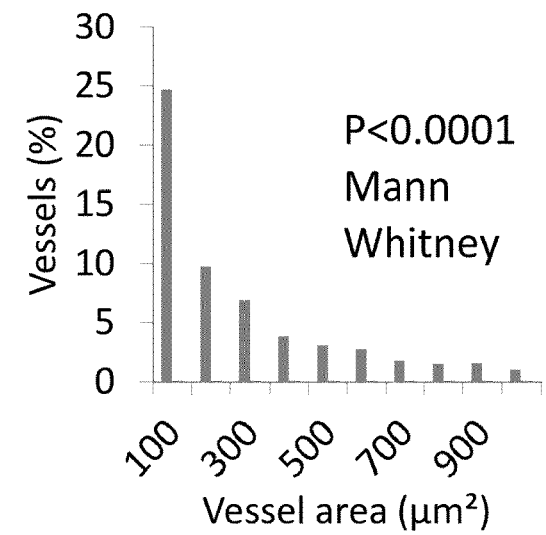

Vessels were identified by CD31 immunohistochemistry on tumour sections (FIG. 11). Fewer small vessels were observed in 15C4 treated tumours, as such a significant difference in the distribution of vessel sizes was observed compared to IgG controls (Two-Way ANOVA, P<0.0001).

Figure 10A:
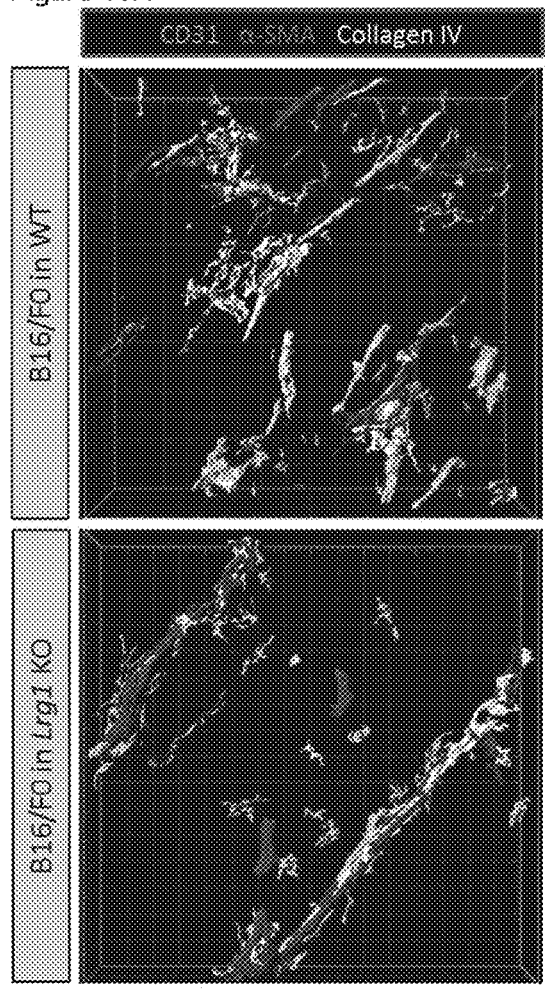
FIG. 10A, reconstruction of blood vessel architecture in B16/F0 tumours taken from wildtype and Lrg1 knockout mice. α-SMA is a marker for pericytes, CD31 is a marker for endothelial cells, Collagen IV is a marker for blood vessels. It is clear from the Lrg1 image that there is increased coverage of pericyte on the blood vessels of the Lrg1 knockout tumour.
Figure 10B:
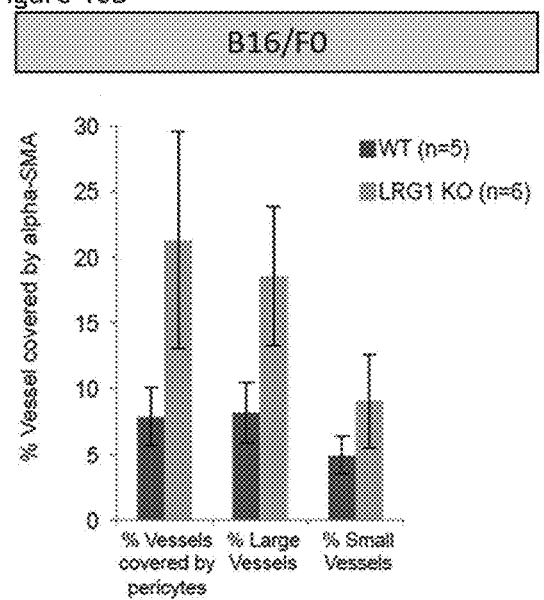
FIG. 10B and FIG. 10C bar charts—quantification of pericyte coverage in the B16/F0 (FIG. 10B) and LL/2 tumours (FIG. 10C).
Figure 10C:
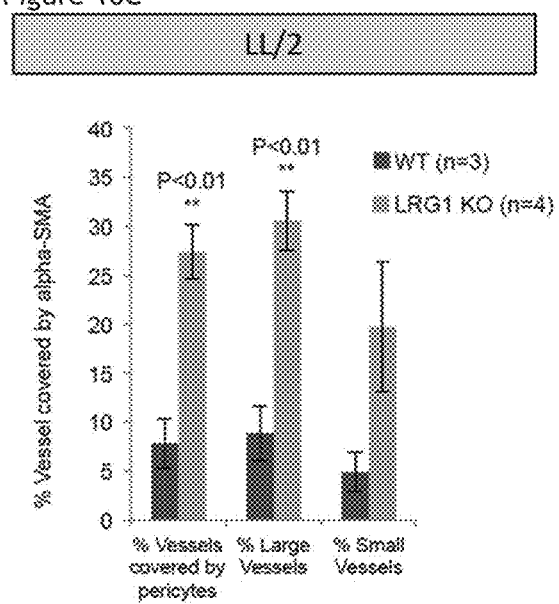

Interestingly, it was also found that loss of Lrg1 resulted in increased pericyte coverage on both large and small vessels, a sign of vessel maturation, in the Lrg1 knockout when compared with the wild type mouse (FIG. 10). α-SMA (smooth muscle actin) is a marker for pericytes. The images show that there are fewer blood vessels not covered by pericytes in the Lrg1 knockout.

Figure 12:
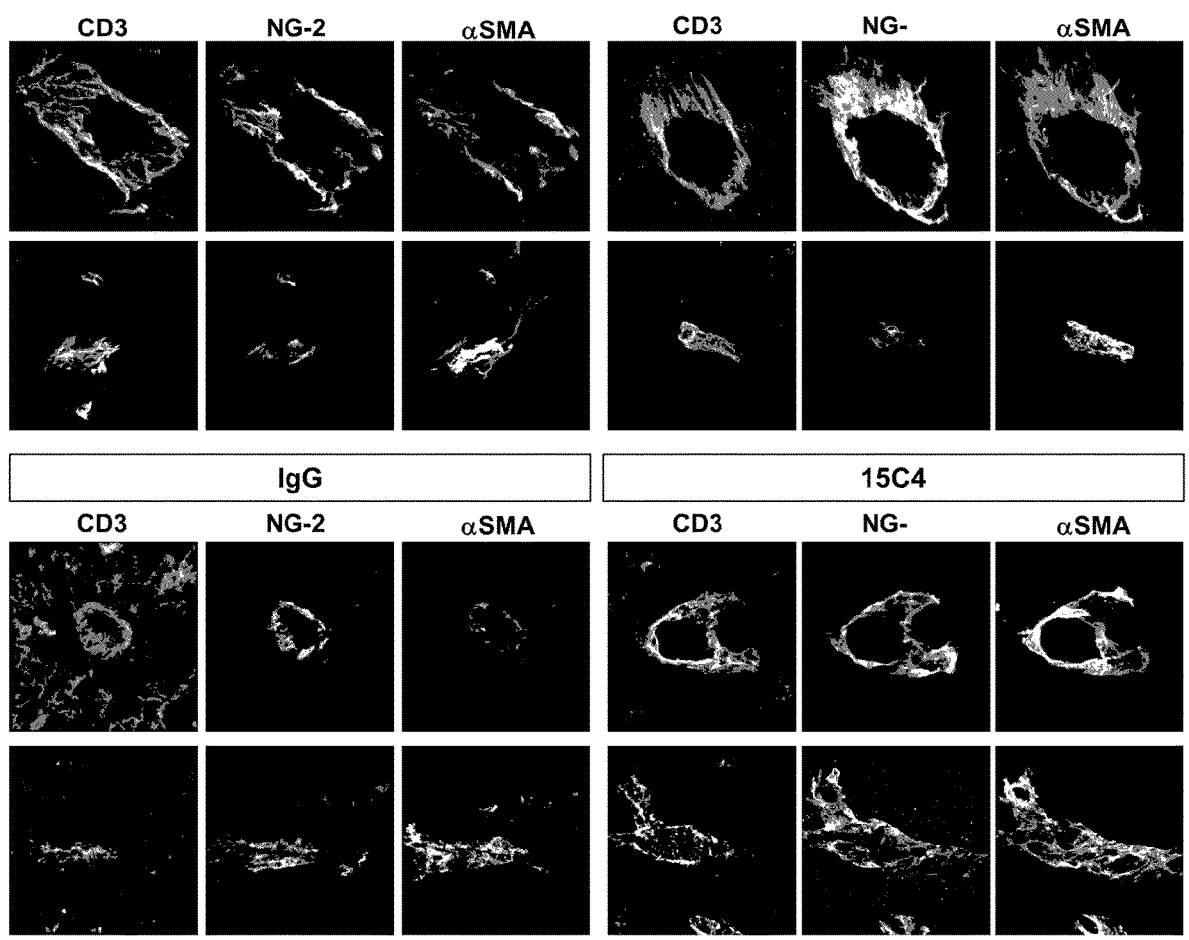
FIG. 12: 15C4 drives normalisation of tumour vessels, and thus replicates the Lrg1 KO phenotype. Immunostaining of blood vessels from cryosections of B16F0 tumours raised in wild-type (WT), Lrg1 knockout (KO), or wild-type mice treated with IgG or 15C4. Sections were labelled with antibodies to endothelial marker CD31, or pericyte markers αSMA or NG-2. Maximum intensity projections of representative images are shown, with the 3 channels split horizontally. Images were taken with a 40× objective on a Zeiss 710 confocal microscope.
Figure 13:
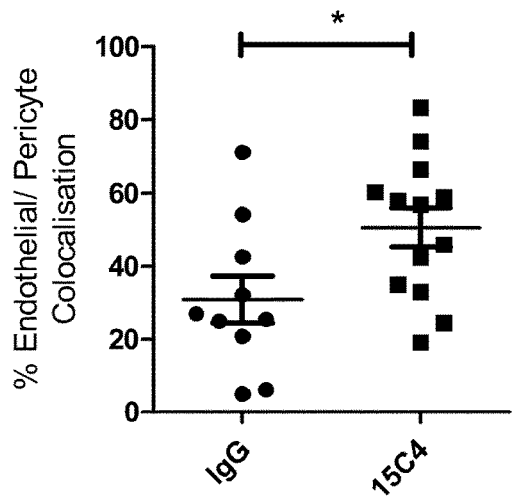
FIG. 13: Quantification of co-localisation of endothelial and pericyte markers. Treatment of B16F0 tumours in C57BL6 mice with anti-LRG1 blocking antibody 15C4 increases endothelial and pericyte co-localisation. The endothelium was identified by CD31 expression; pericytes were identified by either αSMA or NG2 expression. Data are expressed as the percentage of total endothelium that co-localised with one or more pericyte markers. (A) Total pericyte co-localisation, p=0.04, Mann-Whitney Test; (B) αSMA co-localisation, p=0.02, Mann-Whitney test; (C) NG2 co-localisation. IgG N=10, 15C4 N=13.
Figure 13:
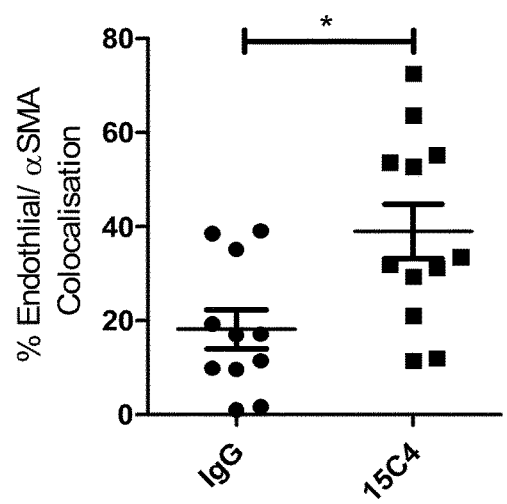
Figure 13:
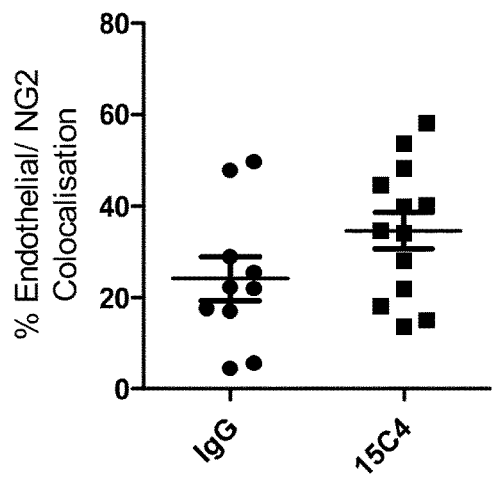

These results were also mimicked in B16/F0 tumours in the presence of antibody 15C4. Treatment of B16F0 tumours in C57BL6 mice with anti-LRG1 blocking antibody 15C4 increases endothelial and pericyte co-localisation. The endothelium was identified by CD31 expression; pericytes were identified by either αSMA or NG2 expression (shown in stained images in FIG. 12 and quantified in FIG. 13).

These results indicate that in tumours of the Lrg1 knockout mouse and in tumours of wild type mice in the presence of antibody 15C4, blood vessels are more functional and mature.

Example 13—15C4 Potentiates the Cytotoxic Activity of Cisplatin

The adherent cell line B16-F0 was harvested and a single-cell suspension of $1\times10^6$ cells in 100 μl PBS was injected subcutaneously into the lower back of C57Bl/6 male mice. Treatment with 15C4 or IgG was started after three days at 50 mg/kg by intraperitoneal injections, and repeated every 3 days. Suboptimal doses of Cisplatin (2.5 mg/kg) were administered to mice bearing tumours with an average size of 0.5 cm$^3$ every other day by intraperitoneal injections. Tumours were measured with callipers every other day and volume was calculated using the formula: $V=(4/3)\times\pi\times(L/2)\times(W/2)\times(H/2)$.

Figure 14:
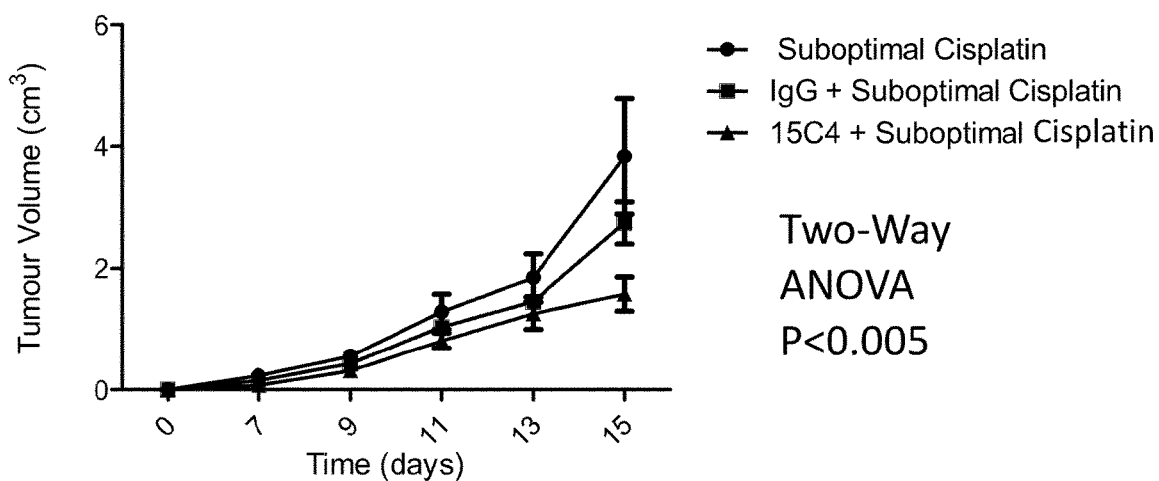
Figure 14:
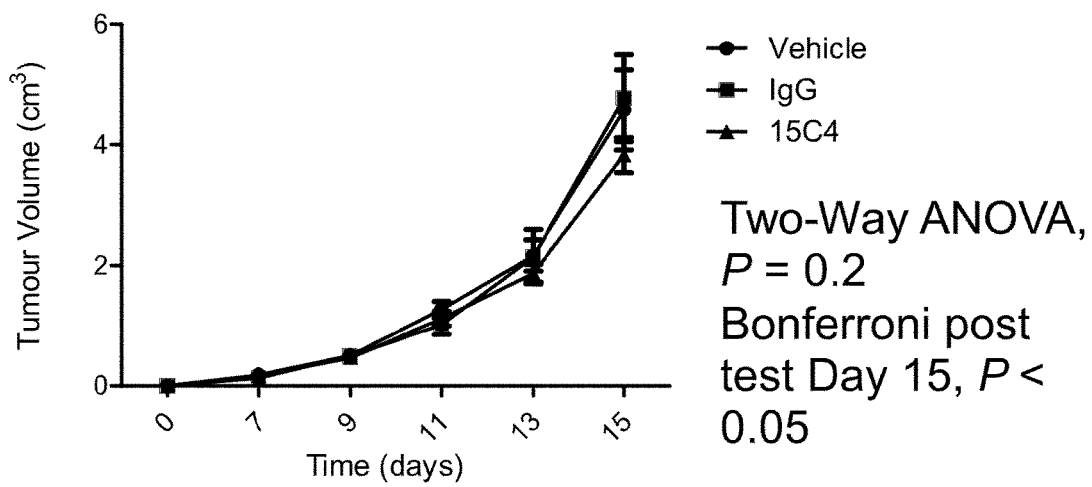

Tumours treated with 15C4 in combination with cisplatin exhibited a significant reduction in tumor growth compared with IgG and cisplatin controls (Two-Way ANOVA, P<0.005) (FIG. 14A). Tumours treated with 15C4 exhibited a similar rate of growth compared with IgG and vehicle controls (FIG. 14B).

Figure 15B:
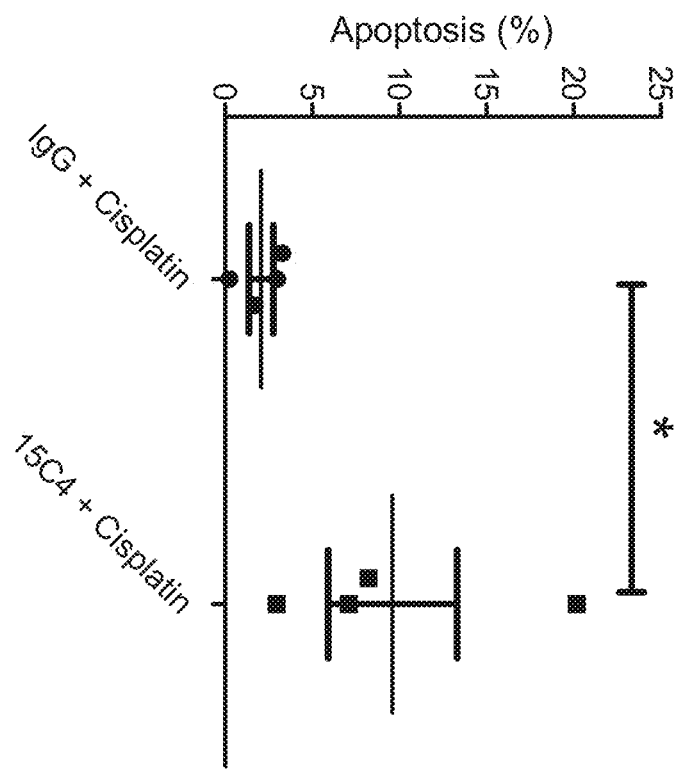

Cisplatin and IgG or 15C4 treated tumours were immersion fixed in 4% PFA overnight at 4° C. and then immersed in 30% sucrose overnight at 4° C. Tumour tissue was then OCT embedded and frozen for sectioning (40 μm). TUNEL assay was performed using an ApopTag in situ apoptosis detection kit according to manufacturers protocol (Merk Millipore, USA). Significantly more apoptosis was observed in tumours treated with 15C4 in combination with cisplatin than in the IgG and cisplatin controls (one-tailed Student's T-test, P<0.05) (FIG. 15).

The DNA double strand break marker γ-H2AX was stained for in tumour sections, indicating cisplatin-induced DNA damage. Significantly more nuclei with γ-H2AX foci were observed in tumours treated with 15C4 in combination with cisplatin than in the IgG and cisplatin controls (one-tailed Student's T-test, P<0.05) (FIG. 16).

Example 14—Mouse Model of Laser-Induced CNV

Dose-Response Analysis of 15C4 and Comparison with Eylea.

Experiments were conducted into the effects of 15C4 on lesion formation in the mouse model of laser-induced choroidal neovascularisation. It was found that 15C4 inhibited lesion formation in the mouse model of laser-induced choroidal neovascularisation (FIG. 17).

The images on the left of FIG. 17A show a typical wild-type mouse retina under normal illumination (Fundus), and under fluorescence illumination, 7 days after three laser burns were administered to the retinal pigment epithelium. Fluorescence images were captured ~60 seconds after systemic dosing with fluorescein (Early Phase FFA) and again after ~7 minutes (Late Phase FFA). At the time of lasering, animals received intraocular injections of either control IgG (top panels) or 15C4 (lower panels). The Early Phase FFA images show the size of the lesions, and the Late Phase images show leakage of fluorescein into the retina. Lesion sizes were quantified for 15C4 at 2.5, 5 and 10 μg doses, and also Eylea at 2 and 4 μg, and the % blocking is a measure of average lesion size relative to that observed in the controls. On the far right a similar analysis was undertaken using Eylea and Magacizumab (both at 2.1 μg) alone and in combination. These experiments show that in this model, 15C4 and the humanised antibody Magacizumab, both inhibit lesion formation with similar efficacy to the VEGF blocker Eylea.

Dose-Dependent Inhibition of Lesion Formation by Magacizumab in Laser-Induced CNV.

Wild type C57B6 mice were anaesthetized and received intravitreal injections of various doses of either Magacizumab, Eylea, or both in combination, immediately following laser photocoagulation of the retinal pigment epithelium. After 7 days (to allow the vascular lesions to form) the mice were again anaesthetized and examined by fluorescein angiography (FFA). Early phase FFA images (taken after 90 s) show the degree of vascularization at the lesion site. Measurement of the lesion area in the early phase images permits quantification in which percentage lesion size is normalized against the IgG4 control (FIG. 18).

Treatment with Magaciznab resulted in a significant reduction in lesion size, both alone and in combination with Eylea (FIG. 18), in comparison with control.

15C4 Reduces Lesion Formation in the JR5558 Mouse.

FIG. 19 also shows a reduction in the number of lesions in the JR5558 mouse when treated with 15C4. 15C4 or IgG at 50 mg/kg was administered IP every 3 days from D14. Eyes were harvested on D25 and RPE/Choroid stained with Collagen IV. The number of lesions was counted and data quantified for the two groups. In the presence of 15C4 there were significantly fewer lesions than in control mice.

Example 15—Biochemical Properties of Magacizumab

The properties of Magacizumab were investigated. Analytical size exclusion chromatography was conducted showing a single peak and no aggregates (FIG. 20A). An anti-hLrg1 competition ELISA was carried out. A dilution series of each purified antibody was competed against a fixed concentration of biotinylated mouse 15C4 for binding to recombinant hLrg1. Bound biotinylated mouse 15C4 was detected using streptavidin-peroxidase and TMB substrate. This was an analytical step in which several humanised variants were tested against the chimeric 15C4, in order to identify those that retained the best binding characteristics. The VH5/Vk3_3B6 clone (later named Magacizumab) exhibited a similar binding profile as the chimeric 15C4 and was therefore selected as the lead antibody (FIG. 20).

FIGS. 21A-21C indicate that Magacizumab produced protein bands on SDS-PAGE consistent with those expected for an antibody under non-reducing and reducing conditions.

FIG. 21D shows the results of a T cell proliferative assay to detect if Magacizumab is de-immunised. The results show that Magacizumab (the Humanised antibody) failed to elicit a proliferative response in any of the 20 donor T cell samples, consistent with the antibody being successfully de-immunised.

REFERENCES

Haupt H., et al. *Physiol Chem.* 358, 639-46 (1977).
Takahashi N., et al.; *Proc Natl Acad Sci USA.* 82, 1906-10 (1985).
Sun D., et al. *Cancer Lett.* 89, 73-9 (1995).
Li X., et al, Neurosci. Lett. 413, 141-144 (2007).
Wang, X., et al. *Nature* 499, 306-311 (2013).
Carmeliet P. and Jain R. K. *Nat. Rev. Drug Discov.* 10, 417-427 (2011)
Maes H., et al. *Cancer Cell* 26, 190-206 (2014).
Caceci et al. Byte 9, 340-362, (1984).
Wong & Lohman *Proc. Natl. Acad. Sci. USA* 90, 5428-5432, (1993).
Ivan Roitt, Essential Immunology, 1988;
Janis Kuby, Immunology, 1992 e.g., pp. 79-81.
Thompson et al. Nucleic Acids Res. 25, 4876-4882 (1994).
Devereux, J. et al. *Nucl. Acids Res.* 12, 387-395 (1984).
Altschul S. F. *Mol. Evol.* 36, 290-300 (1993).
Altschul, S. F. et al., *J. Mol. Biol.,* 215, 403-410 (1990).
Henikoff, S. and Henikoff, J. G., *Proc. Natl. Acad. Sci. USA* 89, 10915-10919 (1992).
Karlin, S. and Altschul, S. F., *Proc. Natl. Acad. Sci. USA* 90: 5873-5787 (1993).

The invention claimed is:

1. An antibody or fragment thereof that specifically binds to human Lrg1 and which comprises CDRs of SEQ ID NOs: 21, 22, 23, 24, 25, and 26.

2. The antibody or fragment thereof according to claim 1, wherein the antibody or fragment thereof comprises:
   (a) a heavy chain variable region amino acid sequence of SEQ ID NO: 1, 5, 7, 9, 11, or 13; or
   (b) a variant of (a) having at least 70% amino acid sequence identity to a sequence of (a), wherein the antibody or fragment comprises CDRs of SEQ ID Nos: 21, 22, and 23, and retains the ability to specifically bind to Lrg1.

3. The antibody or fragment thereof according to claim 1, wherein the antibody comprises:
   (a) a light chain variable region amino acid sequence of SEQ ID NO: 2, 15, 17, or 19; or
   (b) a variant of (a) having at least 70% identity amino acid identity to a sequence of (a), wherein the antibody or fragment comprises CDRs of SEQ ID Nos: 24, 25, and 26, and retains the ability to specifically bind to Lrg1.

4. The antibody or fragment thereof according to claim 1, wherein the antibody comprises:
   (a) the heavy chain variable region of SEQ ID NO: 1 and the light chain variable region of SEQ ID NO: 2; or
   (b) the heavy chain variable region of SEQ ID NO: 1 and the light chain variable region of SEQ ID NO: 15; or
   (c) the heavy chain variable region of SEQ ID NO: 1 and the light chain variable region of SEQ ID NO: 17; or
   (d) the heavy chain variable region of SEQ ID NO: 1 and the light chain variable region of SEQ ID NO: 19; or
   (e) the heavy chain variable region of SEQ ID NO: 5 and the light chain variable region of SEQ ID NO: 2; or
   (f) the heavy chain variable region of SEQ ID NO: 5 and the light chain variable region of SEQ ID NO: 15; or
   (g) the heavy chain variable region of SEQ ID NO: 5 and the light chain variable region of SEQ ID NO: 17; or
   (h) the heavy chain variable region of SEQ ID NO: 5 and the light chain variable region of SEQ ID NO: 19; or
   (i) the heavy chain variable region of SEQ ID NO: 7 and the light chain variable region of SEQ ID NO: 2; or
   (j) the heavy chain variable region of SEQ ID NO: 7 and the light chain variable region of SEQ ID NO: 15; or
   (k) the heavy chain variable region of SEQ ID NO: 7 and the light chain variable region of SEQ ID NO: 17; or
   (l) the heavy chain variable region of SEQ ID NO: 7 and the light chain variable region of SEQ ID NO: 19; or (m) the heavy chain variable region of SEQ ID NO: 9 and the light chain variable region of SEQ ID NO: 2; or
(n) the heavy chain variable region of SEQ ID NO: 9 and the light chain variable region of SEQ ID NO: 15; or
(o) the heavy chain variable region of SEQ ID NO: 9 and the light chain variable region of SEQ ID NO: 17; or
(p) the heavy chain variable region of SEQ ID NO: 9 and the light chain variable region of SEQ ID NO: 19; or
(q) the heavy chain variable region of SEQ ID NO: 11 and the light chain variable region of SEQ ID NO: 2; or
(r) the heavy chain variable region of SEQ ID NO: 11 and the light chain variable region of SEQ ID NO: 15; or
(s) the heavy chain variable region of SEQ ID NO: 11 and the light chain variable region of SEQ ID NO: 17; or
(t) the heavy chain variable region of SEQ ID NO: 11 and the light chain variable region of SEQ ID NO: 19; or
(u) the heavy chain variable region of SEQ ID NO: 13 and the light chain variable region of SEQ ID NO: 2; or
(v) the heavy chain variable region of SEQ ID NO: 13 and the light chain variable region of SEQ ID NO: 15; or
(w) the heavy chain variable region of SEQ ID NO: 13 and the light chain variable region of SEQ ID NO: 17; or
(x) the heavy chain variable region of SEQ ID NO: 13 and the light chain variable region of SEQ ID NO: 19.

5. The antibody or fragment according to claim 1, which binds to Lrg1 with an affinity of 1 nM or less.

6. The antibody or fragment according to claim 1, which comprises an Fc region which is an IgG1, IgG2, IgG3 or IgG4 region.

7. The antibody or fragment thereof according to claim 1 conjugated to an additional moiety.

8. A composition comprising an antibody or fragment thereof according to claim 1 and at least one pharmaceutically acceptable diluent or carrier.

9. A method of treating a disease or condition comprising administering to an individual an antibody or fragment thereof according to claim 1, wherein the disease or condition is a solid tumor with Lrg-1 mediated vasculoproliferation or a vasculoproliferative condition mediated by Lrg-1.

10. The method according to claim 9, wherein the solid tumor is selected from a brain, breast, kidney, colorectal, lung, prostate, head and neck, stomach, pancreatic, skin, cervical, bone, ovarian, testicular, and liver tumor.

11. The method according to claim 9, wherein the vasculoproliferative condition comprises neovascularisation, vascular endothelial cell proliferation, angiogenesis, telangiectasia, or microaneurysms.

12. The method according to claim 9, wherein the vasculoproliferative condition is a vasculoproliferative condition of the eye.

13. The method according to claim 9, wherein the treatment further comprises the administration of an antiangiogenic compound.

14. The method according to claim 9, wherein the treatment of cancer further comprises the administration of a cytotoxic compound or immunotherapeutic agent.

15. The antibody or fragment thereof according to claim 1, wherein the antibody or fragment comprises a Fab fragment, a F(ab')$_2$ fragment, a Fab' fragment, a Fv fragment or a scfv.

* * * * *